United States Patent
Pinsky et al.

(10) Patent No.: US 7,477,053 B2
(45) Date of Patent: *Jan. 13, 2009

(54) DETECTION OF ELECTROMAGNETIC FIELDS

(76) Inventors: Carl Pinsky, Apt. 206, 663 Jefferson Avenue, Winnipeg, Manitoba (CA) R2V 0P5; Frank S. LaBella, Box 4059 RR1, Oakbank, Manitoba (CA) R0E 1J3

(*) Notice: Subject to any disclaimer, the term of this patent is extended or adjusted under 35 U.S.C. 154(b) by 0 days.

This patent is subject to a terminal disclaimer.

(21) Appl. No.: 10/724,367

(22) Filed: Dec. 1, 2003

(65) Prior Publication Data

US 2004/0222789 A1   Nov. 11, 2004

Related U.S. Application Data

(63) Continuation of application No. 09/493,686, filed on Jan. 28, 2000, now abandoned, and a continuation-in-part of application No. 08/696,880, filed as application No. PCT/CA95/00082 on Feb. 20, 1995, now Pat. No. 6,150,812.

(30) Foreign Application Priority Data

Feb. 21, 1994  (GB)  .................................. 9403245.5

(51) Int. Cl.
*G01N 27/72* (2006.01)
*G01N 33/48* (2006.01)
*G01R 33/07* (2006.01)

(52) U.S. Cl. .................... 324/261; 600/409; 204/400

(58) Field of Classification Search ................ 324/204, 324/228, 251, 260–261, 300, 309; 204/400; 600/407, 409

See application file for complete search history.

(56) References Cited

U.S. PATENT DOCUMENTS

| 3,028,596 | A |   | 4/1962  | McGillem et al. |
| 3,129,330 | A |   | 4/1964  | Seling |
| 3,906,231 | A |   | 9/1975  | Fletcher et al. |
| 4,106,340 | A |   | 8/1978  | Hamid |
| 4,121,288 | A |   | 10/1978 | Hickam |
| 4,385,516 | A |   | 5/1983  | Uffelman |
| 4,551,679 | A | * | 11/1985 | Bossaert ..................... 324/309 |

(Continued)

FOREIGN PATENT DOCUMENTS

JP   2001580   1/1990

(Continued)

OTHER PUBLICATIONS

Chemistry Daily, "Electromagnetic Radiation," 3 pages.*

(Continued)

*Primary Examiner*—Bot LeDynh
(74) *Attorney, Agent, or Firm*—Michael I. Stewart

(57) ABSTRACT

Method and apparatus for detecting or analyzing chemical reactions, such as an enzyme reaction, and other events in which electron translation is accompanied by photon emission utilizing a magnetometer probe to detect a change in electromagnetic field strength as a characterization of the event or of a substance. The event may be of unknown cause and a recorded time course of the change in electromagnetic field strength may be compared with known time course of known events to determine the cause of the unknown cause event. Similarly, a chemical substance may be detected and its identity determined.

5 Claims, 54 Drawing Sheets

INSTRUMENTATION, BLOCK DIAGRAM

U.S. PATENT DOCUMENTS

| | | | |
|---|---|---|---|
| 4,620,099 A | 10/1986 | Schoenig, Jr. et al. | |
| 4,620,100 A | 10/1986 | Schoenig, Jr. et al. | |
| 4,724,390 A | 2/1988 | Rauscher et al. | |
| 4,769,601 A | 9/1988 | Herrick | |
| 4,833,392 A * | 5/1989 | Hahn et al. | 324/313 |
| 4,863,876 A * | 9/1989 | Hevey | 436/537 |
| 5,201,311 A | 4/1993 | Bottomley et al. | |
| 5,291,135 A * | 3/1994 | Hotta et al. | 324/248 |
| 5,325,854 A * | 7/1994 | Ehnholm | 600/420 |
| 5,338,687 A * | 8/1994 | Lee et al. | 436/173 |
| 5,378,895 A | 1/1995 | Cole et al. | |
| 5,410,252 A | 4/1995 | Potter et al. | |
| 5,436,718 A * | 7/1995 | Fernandes et al. | 356/73 |
| 5,818,231 A * | 10/1998 | Smith | 324/309 |
| 5,850,285 A | 12/1998 | Hill, Jr. et al. | |
| 6,150,812 A | 11/2000 | Pinsky et al. | |

FOREIGN PATENT DOCUMENTS

JP    4238281    8/1992

OTHER PUBLICATIONS

Carroll, Robert Todd, "Electromagnetic Field," The Skeptic's Dictionary, 8 pages.*

Kikipedia, "Electromagnetic Radiation," 9 pages.*

Hoenig, H.E. et al., Biomagnetic multichannel system with integrated SQUIDs and first order gradiometers operating in a shielded room. (1989) vol. 29, pp. 809-813. XP00037540.

Misra, Mira et al., NDE Applications of squid magnetomety to electrochemical systems. vol. 27, No. 2., (1991) pp. 3245-3247.

Bellignham et al., Squid Technology applied to the study of Electrochemicla corrosion, vol. Mag. 23, No. 2, pp. 477-479 (1987).

* cited by examiner

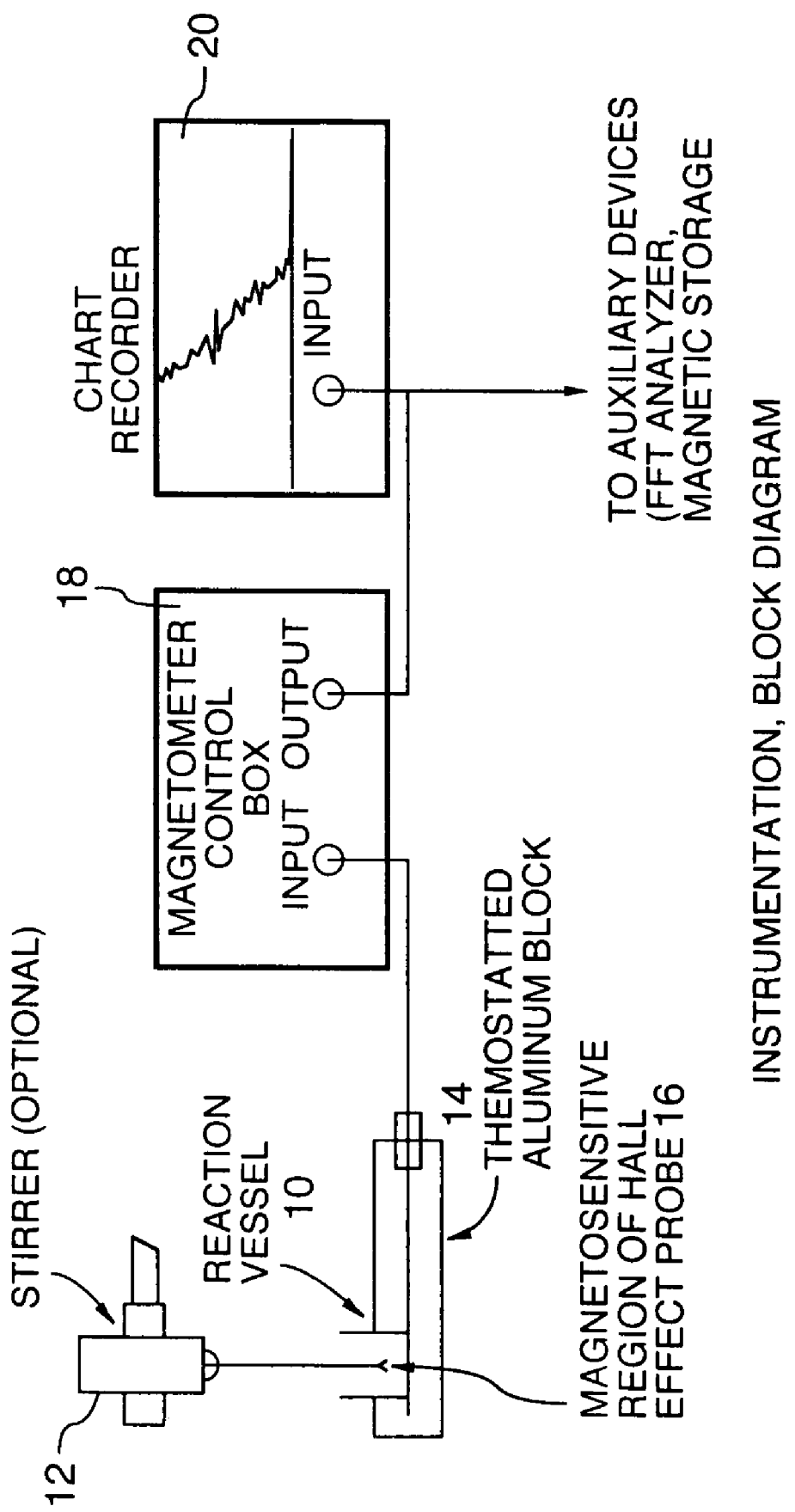

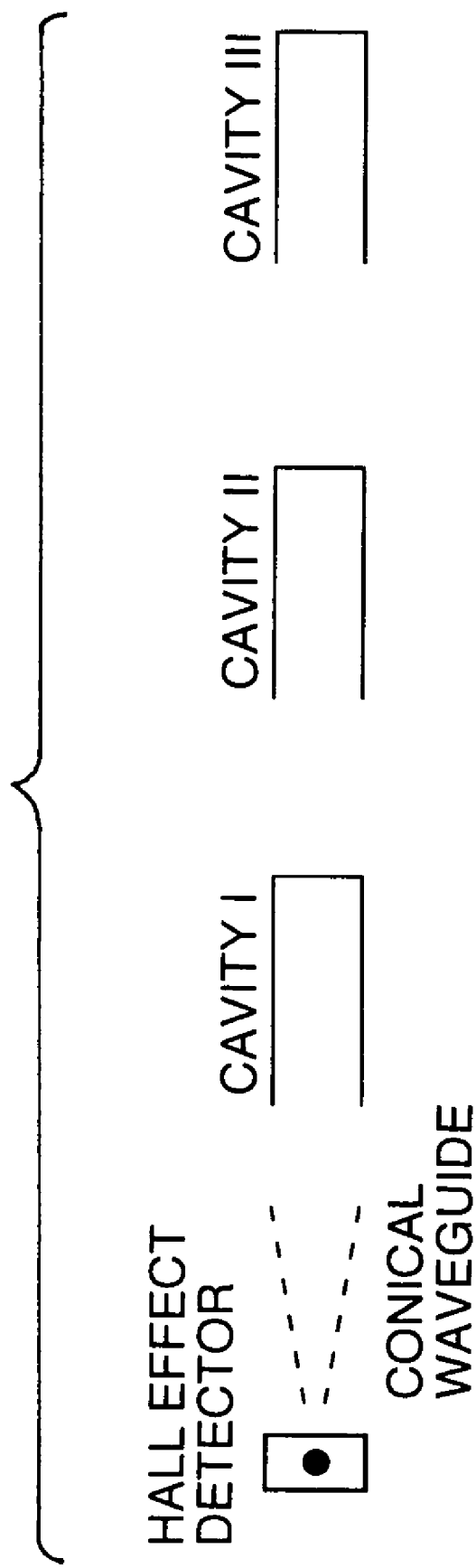

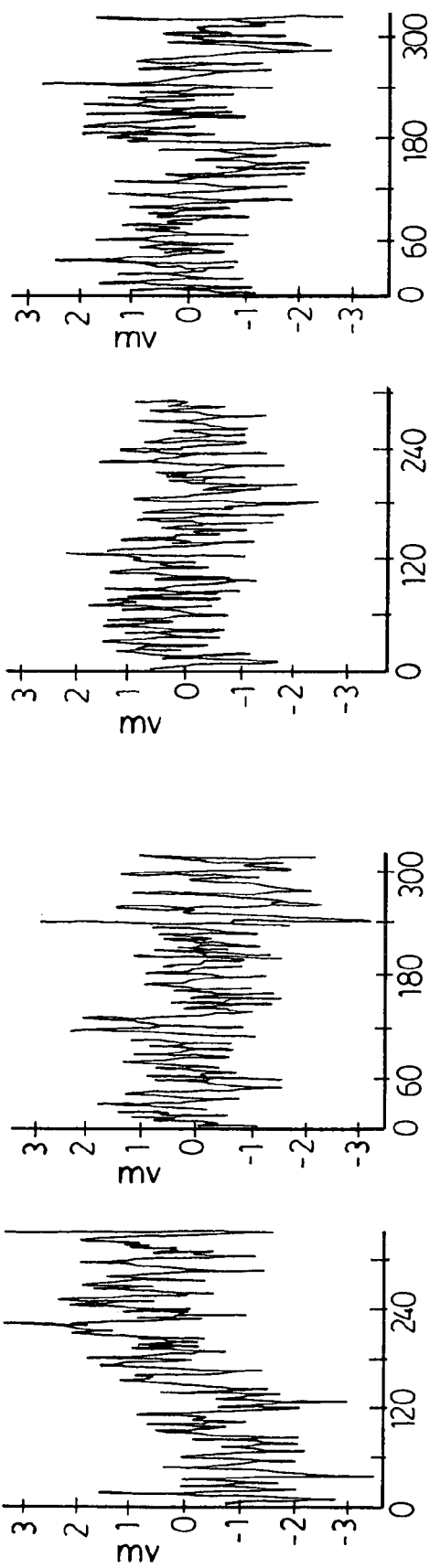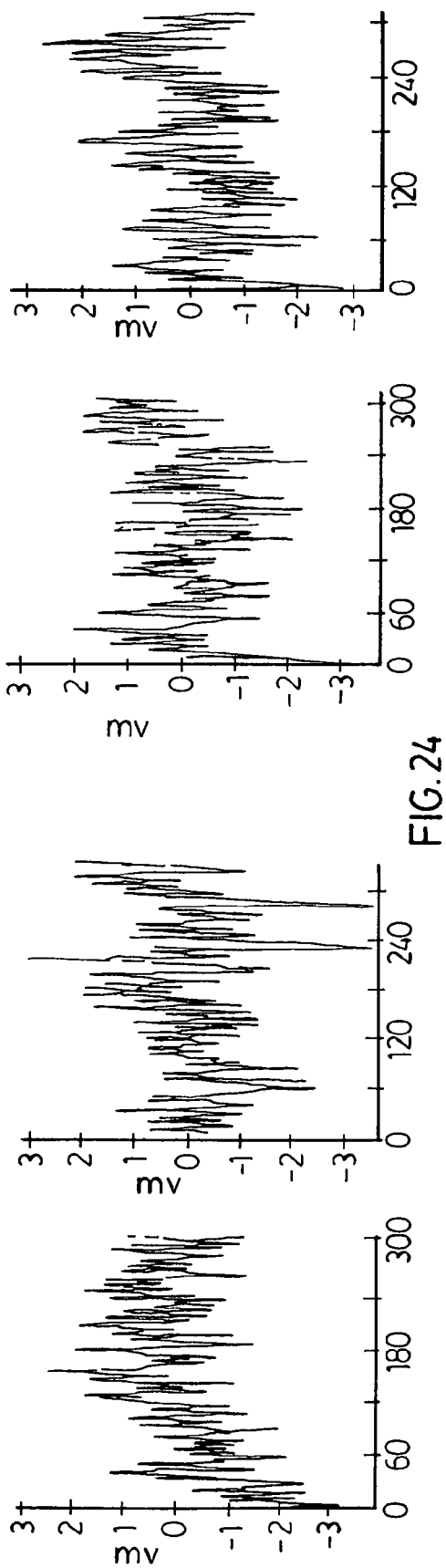
FIG. 24

Fig.29 A
COMPUTER-GENERATED
FACSIMILE OF CHART
RECORDING
Fig.29 B
ELIMINATION OF DENSITIES
BELOW AN ARBITRARY
THRESHOLD. SHOWN ON
COMPUTER SCREEN
FACSIMILE OF CHART
RECORDING
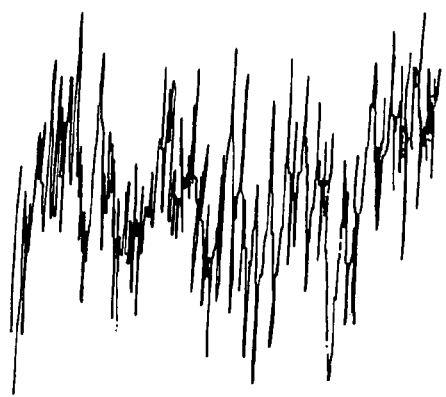
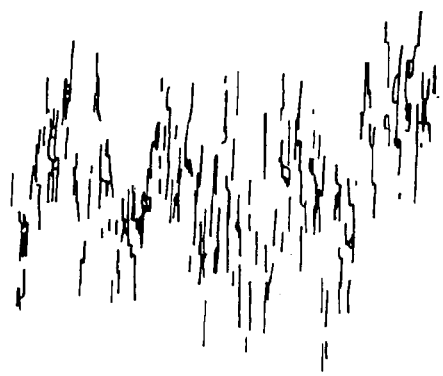
REPRESENTATIVE CALCULATIONS
* number of densities:136
* number of densities with areas > 70 units
* Total area of densities: 5709 units
* Total area of densities > 70 units: 2559 units

DETECTION OF ELECTROMAGNETIC FIELDS

REFERENCE TO RELATED APPLICATION

This application is a continuation of U.S. Patent application Ser. No. 09/493,686, filed Jan. 28, 2000, now abandoned, and is a continuation-in-part of U.S. patent application Ser. No. 08/696,880, now U.S. Pat. No. 6,150,812, effectively filed Oct. 18, 1996 as a 35 USC 371 filing of PCT/CA95/00082 filed Feb. 20, 1995.

FIELD OF THE INVENTION

The present invention relates to the detection of electromagnetic fields produced by certain events, such as chemical reaction, atomic and molecular resonance, fluctuation in molecular bond length, energy and strength, change in state of matter, atomic nuclear disintegration, fission and fusion, photoelectric-activated electron displacement, spontaneous fluctuations in fluctuation states, as well as a device for measuring the generation of such electromagnetic fields.

BACKGROUND TO THE INVENTION

The motion of the electrons within a single isolated atom or molecule generates electromagnetic fields which can be detected external to the boundaries of the atom or molecule. The magnitude and frequency of such external fields depends mainly upon the following factors:

(i) the angular momentum of the electron as it spins on its axis (=electron spin angular momentum), (ii) the angular momentum of the electron as it moves in quasicircular orbital paths around the nucleus (=electron orbital momentum), (iii) the quantized energy states of the electron orbital paths and angular spin velocities, (iv) interactions between intraatomic and intramolecular electron motions as governed by Lenz's law, (v) rate of individual transitions between quantized energy states and the frequency of transitional events, (vi) interactions between electron orbital and spin angular moments and nuclear magnetic moments, and (vii) intensity, frequency and direction of externally imposed magnetic fields.

The electromagnetic fields generated by electron motion within atoms or molecules are accompanied by the simultaneous emission of photons whose energies are characteristic of the frequencies of the associated intraatomically- or intramolecularly-generated external electromagnetic fields. The range of atomic and molecular electromagnetic frequencies extends from microwave and even lower-frequency energies, up to ultraviolet and even higher-frequency energies. The invention to be described herein utilizes novel means to record the extraatomic microwave energies which propagate away from the atoms of origin at the speed of light.

SUMMARY OF INVENTION

As described in more detail below, the present invention utilizes the electromagnetic consequences of intraatomic changes in electron position, energy state, acceleration, deceleration, formation and annihilation, to observe those events by recording the electromagnetic fields, both near and propagating, which can be detected in the close vicinity of the energetically-active atom or molecule or at regions remote from such energy-emitting or -absorbing ultramicroscopic entities.

A Hall effect magnetometer working with enhanced sensitivity is utilized to detect the extraatomic electromagnetic fields arising from intraatomic electron motion and quantum state changes in samples of matter under inspection. Detection of propagating electromagnetic fields is improved and enhanced by exploitation of microwave waveguide and surface-energized resonant magnetic and paramagnetic phenomena.

With such enhancements detection of extraatomic electromagnetic fields, such as those described above, permits the study of, among many other phenomena, interactions between molecules, and between molecules and atoms, permits characterization of types of reactions and identification of the reactant chemicals by (i) direct magnetometric detection of magnetic fields, especially electromagnetic fields propagating at the velocity of light and in the microwave frequency ranges, external to the reactant molecules or atoms and by (ii) magnetometric detection of magnetic domain configurations that are set up both by near and by propagating microwave electromagnetic fields in substances which surround the reactants and which behave as transducers of high frequency atomic/molecular magnetic field oscillations into magnetic domain fluctuations at much lower frequencies, e.g. 0 to $10^4$ hertz (Hz).

The transducing substances can be in gaseous, liquid or solid phases and are weakly ferromagnetic over at least some range of imposed microwave energies. Transducing substances which are strongly ferromagnetic by virtue of iterative metallic/metalloid crystal ionic bonds exhibit a weak ferromagnetic transduction mode as a surface phenomenon of only several atoms thickness, consistent with the ability of thin films of reactant systems observed in our studies to increase the sensitivity and reproducibility of the device described herein. The substances deoxyribonucleic acid (DNA) and heme:protein complexes are highly effective atomic/molecular transducers of radio-, microwave- and higher frequency electromagnetic energies and, by virtue of their iterative molecular structures, behave as low-loss resonant (ref. Co94) couplers for transmission of electromagnetic fields propagating from energetic atoms and molecules toward the magnetometric detector.

Similar frequency conversion mechanisms inherent in ferromagnetic, weakly ferromagnetic and paramagnetic micro- and nanostructures and systems (e.g. atoms, molecules, nano- and microcavities and stereosurfaces, nano-, micro- and ultrafine wires), are utilized in the invention to enable detection, by enhanced conventional magnetometry, of chemically- and intraatomic spontaneously-generated electromagnetic and quantum phenomena. Utilizing the magnetometry, microwave and energy-transduction technologies described here, quantum particulate and propagating high-frequency electromagnetic emissions released during radioactive decay are exploited to detect and measure alpha, gamma and beta (+) and beta (−) emission from radioactive sources whose energy levels may range from very weak to very strong.

Extraatomic propagating electromagnetic fields can be detected with the invention at distances remote from the sample of energetic matter. The propagating electromagnetic fields are only marginally hampered, impeded or shielded by, and often are enhanced by, conventional electromagnetic shielding measures since the interposition of shielding materials results ubiquitously in frequency conversions that give rise to the equivalent of a very broadband frequency source seen by the magnetometer detector, even where the original propagating signal may be largely monochromatic.

The invention, therefore, represents a universal detector of fluctuations in intraatomic electron and nuclear quantum states and of the near and propagating electromagnetic fields originating from the atom or atoms under observation. These quantal fluctuations reside in all forms of matter, whose dimensions may range from macroscopic to ultrananoscopic. The present invention thus constitutes a practical and reliable transducer of the magnetic intra- and extraatomic consequences of interactions between quantum electron states and propagating electromagnetic fields over an extremely wide range of field strengths and frequencies.

The present invention does not require any technically-generated external magnetic fields, either static or time-variant, but includes simple high-permeability ferromagnetic shielding as a means to reduce the ubiquitous geomagnetic field and its inherent fluctuations. The same shielding serves, over a wide range of frequencies, to reduce the effects of stray magnetic fields of non-geomagnetic origin and is also an important component of the frequency-changing transduction mechanism whereby electromagnetic energies originating at atomic frequencies promote the formation of ferromagnetic or quasiferromagnetic domains which participate in the frequency transduction process and give rise to electromagnetic fields at frequencies detectable by modified but essentially conventional magnetometry.

Accordingly, in one aspect of the present invention, there is provided a method of detection of an event in which quantum state changes in intraatomic electrons result in extraatomic electromagnetic fields, both near and propagating, which comprises detecting a change in extraatomic electromagnetic field strength caused by the event. Such event may comprise, among many other possibilities, exposure to a static magnetic field, to a slowly-varying magnetic field, to a propagating electromagnetic field at any frequency or combination of frequencies technologically-producible or that have been observed or are in theory observable in nature, a chemical reaction, a molecular interaction, a change of state of matter, stochastic fluctuations in strength, number, direction and configuration of atomic and molecular bonds, changes in interactions between electron quantum states and the atomic nucleus and changes in electron quantum states in ultrabrief intervals just preceding, during and subsequent to nuclear disintegrations.

In one embodiment of the invention, there is provided a method of detecting an event in which electron translation is accompanied by photon emission, which comprises measuring intra-atomically-generated magnetic moments, detecting changes in the electromagnetic field strength caused by the event, recording a time course of such changes in electromagnetic field strength as the characterization of the event, and analyzing the recorded characteristic time course of the changes to obtain information relating to the event.

Such event may be of known cause and a time course of the change in extraatomic electromagnetic field strength, i.e. the changes in electromagnetic field strength over time, may be recorded as a characterization of the event.

Alternatively, the event may be of unknown cause. A time course of the change of electromagnetic field strength is recorded and compared with predetermined time courses of known events in which changes in intraatomic electron quantum states are accompanied by changes in extraatomic electromagnetic fields, to determine the cause of the unknown cause event.

One specific application of the procedure of the invention is to determine the electromagnetic consequences of enzyme reactions by detection and measurement of changes in the extraatomic electromagnetic field strength at temperatures which are suitable, even when not optimal, for the enzyme reaction of interest.

The recordal of the change of extraatomic electromagnetic field strength may be effected in any convenient manner which permits the characteristic time course of the event to be provided and, if desired, compare with known prior-recorded time courses. Such analysis may be effected by one or more modes of signal spectral or frequency analysis, e.g. by Fast Fourier Transform (FFT) procedures and may be enhanced, augmented and/or assisted by other forms of signal analysis, such as response averaging, pattern recognition and/or waveform-trend forecasting.

The change in extraatomic electromagnetic field strength caused by the event may be detected in any appropriate and desired manner. As described in more detail herein, the detection may be made by a magnetometer probe capable of generating an electrical signal in response to an electromagnetic field with the electrical signal being of a strength proportional to the strength of the electromagnetic field and the recording of the change in electromagnetic field strength then being made by recording the time course of the electrical signal produced by the magnetometer.

Functional operation of the present invention relies preferably on a gallium arsenide semi-conductor and is based upon the Hall effect. With this effect loosely-bound electrons moving in an electromagnetic field experience a force exerted that is mutually at right angles to that of the field and to the electron's direction of motion. In a solid substance, this effect will cause a difference in electrical potential (i.e. a "Hall potential", or "voltage") between the two opposing surfaces. Semi-conducting crystals in general, and the semiconductor crystal, gallium arsenide, in particular, have electron characteristics highly suitable for utilizing the Hall effect. The magnitude of response to electromagnetic signals is virtually independent of magnetic field frequency (in cycles per second or hertz) thus making the detector exceptionally useful for measuring very weak electromagnetic signals over an extremely wide range of frequencies, from a steady, unvarying magnetic field (zero hertz) up to billions of hertz (gigahertz or even higher). All forms of matter, in following the rules of quantum mechanics, spontaneously emit propagating electromagnetic waves, typically at frequencies of one gigahertz or higher. This range of electromagnetic radiation is referred to, by technical convention, as microwaves.

The spontaneous emission of microwave energy occurs even when a chemical substance is not being excited by light, heat or nuclear radiation and not reacting chemically with any other compound. Under such conditions a chemical (atom, or molecule) is said to be in its ground state. Matter at or close to the ground state has reduced proportions of quantum-excited electrons but, nevertheless, even at room temperature, has sufficient electrons in excited states for the detector to respond to the spontaneously-emitted microwave energy generated by such electrons. This circumstance is enhanced by the broad-band characteristics of the recording system provided herein. The present invention detects spontaneous microwave radiation from chemicals at a distance, even when such chemicals are enclosed in different kinds of containers, including metals which would conventionally be expected to block the propagation of microwave emission. The ability of microwave energy apparently to pass through metallic shielding is a well-known and troublesome anomaly often seen in the communications industry. This phenomenon is most frequently encountered when eddy currents of electromagnetic current are set up by induction in the walls of a metallic enclosure, or in a virtual dipole constituted by a linear conductive structure of length fortuitously close to some integral multiple of the microwave signal's quarter-wavelength. Eddy currents occurring on the metallic structures serve to sustain and enhance further propagation of the microwave signals which originate in the chemicals being examined.

The ability of the device herein to detect extremely low microwave energies may in part be a consequence of a natural signal enhancement phenomenon, identified as stochastic resonance. The phenomenon has been more intensively studied in the disciplines of biology, chemical kinetics and information theory than in physics or communications, although practical applications in electronic circuit design are beginning to emerge. Stochastic resonance theory accounts for the enhancement of a weak, periodic, coherent signal, otherwise obscured by the presence of a non-coherent noise signal, to the point of clear detection by the superposition of additional noise with appropriate amplitude, frequency and phase.

The preferred embodiment of the sensor is capable, in a statistically sound manner, of distinguishing between substances on the basis of their electromagnetic emissivity over a wide range of frequencies. Intended applications of the invention include detection, at measurable distances from the probe, of concealed substances including explosives, radioactive isotopes, chemically active organic matter, enzyme activity, and geoterrestial phenomena.

BRIEF DESCRIPTION OF DRAWINGS

FIG. 1a is a schematic representation of a device provided in accordance with one aspect of the invention.

FIG. 1b represents a waveguide system utilizing a tapered microwave horn to match a large area of ambient microwave energy to the much smaller area at the Hall effect detector probe. The illustration shows a sequence of three cylindrical resonant cavities (total number is empirically optional) which serve as signal-activated repeaters of microwave energy from microwave sources to the wide opening of a linearly-tapered ("conical") waveguide and hence to the Hall effect detector. Samples are effective when placed at any point along the indicated chain of microwave energy transmission.

FIGS. 1c are contained in Table 5.

FIG. 24 shows chart recordings of four out of eight tests and four out of eight control runs in which a 500 mg bottle of hydrazine sulfate was contained in a tall cardboard box while the control was an empty bottle of similar size in a similar box. The test or control samples were placed a few inches from the sensor for periods of 10 seconds and then returned to the next room. Eight applications of test or control bottles were made is non-systematic order.

FIG. 29 comprises a pen-and-ink chart record and a computer-generated record.

GENERAL DESCRIPTION OF INVENTION

Figure 1C:
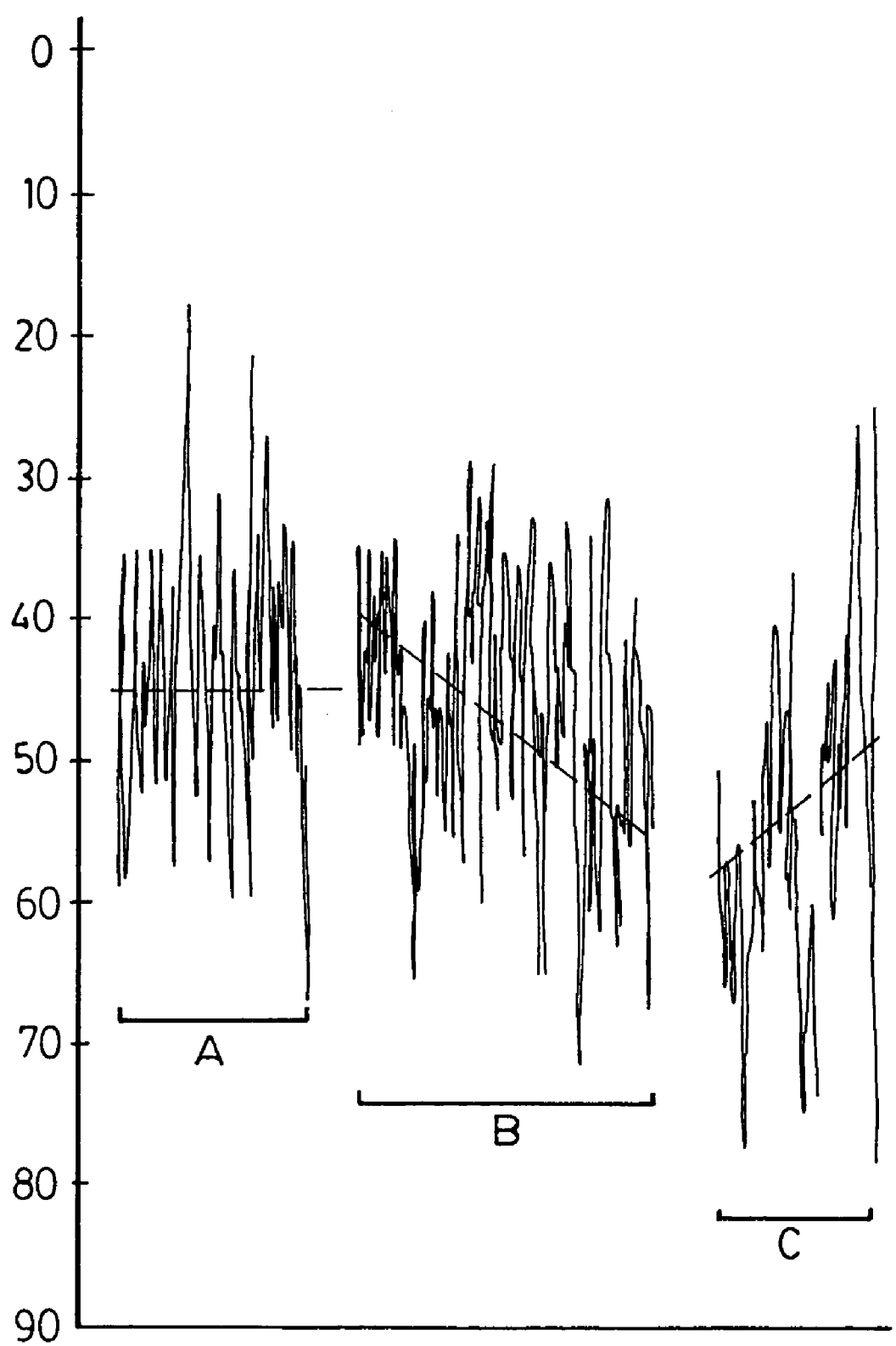
FIG. 1c is a graphical illustration of the microwave detection sensitivity of the invention. A is microwave field energy off, B is microwave field on; 1.0 picoWatt at 11.3 GHz, applied via the wide bell opening of a tapered waveguide radiation, 60 cm distant from a Hall effect detector surface. C is microwave field energy off. Details concerning

No net magnetic field at low (e.g. 0 to $<10^4$ Hz) frequency can be recorded, except over very short intervals, from macroscopic aggregates of atoms or molecules at rest in their ground state. This is because the magnetic moments of the individual atoms or molecules in such aggregates will on average find orientations whose resultant external magnetic field intensities are for all practical purposes zero. Only by the imposition of an external coercive agency can a macroscopic system in any state of matter including crystalline lattice structures generate detectable slowly-varying resultant external magnetic fields on other than a stochastic basis. The external coercive agency must be capable of aligning the magnetic moments of a plurality of the atoms or molecules in the aggregate. Past technology and geo/cosmological natural circumstance have relied upon the application of external magnetic or electric fields, electromagnetic radiation (including visible light) or extremes of heat (at times coupled with mechanical forces) to provide the coercive energy necessary for detectable resultant magnetic alignment.

The present invention is novel and unique that the intraatomic quantum dynamic electronic events which accompany nuclear disintegrations, spontaneous changes in intraatomic quantum states, annihilation and reaction of subatomic particles and changes in electron spin states during chemical reactions, are exploited to synchronize the alignment-coercing quantum events described in factors (i) through and including (vii) discussed above in the "BACKGROUND TO THE INVENTION" and thereby provide a coercive agency, intrinsic to the reacting atom/molecule itself, capable of producing the described atomic/molecular alignment. The alignment synchronization is initially temporal and will occur in any state of matter or medium in which the chemical reaction(s) occur(s). The temporal synchrony quickly leads to spatial ordering of atomic or molecular moments, since the electric and magnetic forces generated by the chemical reaction will interact complexly to reduce and maintain the total free energy of the aggregate to and at a minimum. In this sense, the initial and the maintained synchrony of chemical reaction-driven atomic electronic events substitutes for the ordered interatomic geometrical constraints and interactions which occur in the solid crystalline state of matter and which give rise to magnetization in ferromagnetic substances. Such interatomic or intermolecular ordering, which we designate as "chemical reaction-induced magnetosynchrony" or CRIM, can give rise to the equivalent of enormous applied fields in the material aggregate, e.g. in magnetized iron a submicroscopic domain of $10^{15}$ atoms can have interatomic alignments equivalent to an applied field of $10^3$ .T.cm$^{-1}$ (ref. Ha49). In many chemical reactions, the largest single contribution that will be made by CRIM is the quantized change in electron spin state, since the gyromagnetic ratio, g (ratio of electron spin angular momentum to electron orbital momentum), for ferromagnetic substances is characteristic of the spinning electron (ref. Ha49). In this regard, the present invention, while applicable to all categories of chemical reactions and molecular interactions, is especially useful for the detection and analysis of those reactions associated with changes in spin states (quantized energy levels for electrons in different orbits and orbitals) of one or more of the reactants. This is interpretable as the development of a reaction-specific pattern of intraatomic quantum states with such pattern expectedly capable of generating patterns of extraatomic propagating electromagnetic fields some portions at least of whose energy will be unique to or characteristic of the nature of the chemical reaction which has initiated atomic or molecular synchrony and spatial ordering. Such analysis is of particular relevance in evaluating the characteristics of enzyme reactions, since many enzyme-substrate interactions can be largely or totally characterized by reaction-driven electron spin phenomena, mainly those of enzyme-substrate interaction-initiated transitions in electron spin state. The present invention discerns such phenomena in the reaction vessel described herein via simple magnetometery, which requires no application of an external magnetic field and no high-frequency exposure or specialized high-frequency detection system. The present invention does not a require low-temperature cryogenic environment for its operation and can be utilized at noncritical laboratory temperatures, usually ranging from about 15° C. to about 40° C., with even greater latitude where desired.

DESCRIPTION OF PREFERRED EMBODIMENT

Referring to FIG. 1a, there is illustrated therein a schematic representation of a device for detection of chemical reactions, other molecular interactions, atomic interactions, spontaneous fluctuations in intraatomic quantum states and changes in state of matter. As seen therein, the device includes a reaction vessel 10, which can be equipped with a stirrer 12 when appropriate.

A Hall effect magnetometer probe 16, and when desired the reaction vessel, is/are enclosed in a thermostatted split solid aluminum block jacket 14 which is hermetically sealed to provide optimal temperature stability and intimate thermal contact between the thermostatted mass 14, Hall effect probe 16 and reaction vessel 10. This diminishes to small proportions any fluctuations in temperature gradient between the components sealed into the block 14. In a preferred embodiment of this invention, the magnetometer probe 16 is a semiconductor Hall effect generator, preferably gallium arsenide. Provision of the temperature-stabilizing jacket 14 reduces variation in magnetometer probe output that might otherwise arise from ambient thermal fluctuation. The stabilizing jacket 14 is fabricated from a solid block of nonferromagnetic metal having high thermal conductivity e.g. aluminum or copper. Active thermoregulation of the magnetosensitive probe 16, utilizing electronic temperature sensors and control circuitry, can be employed to enhance thermal stability even further. Thermal insulation, provided by adherent thermoplastic material, provides still greater protection from output signal variations due to ambient temperature changes.

In the specific equipment used to generate the magnetometer charts of FIGS. 2 to 23, the magnetometer probe 16 uses a gallium arsenide semiconductor Hall effect generator with a circular magnetosensitive area of 16 mm$^2$. The reaction tube 10 consists of a 20 mm length of borosilicate glass tubing of 4 mm i.d. and is fixed to the flat blade of the probe at the magnetosensitive area.

The reaction vessel 10 may be dimensioned to accommodate any desired volume of liquid. In the specific device described above, solution volumes up to 1000 microlitres (μL) may be added to the reaction tube 10 and volumes as low as 1.0 μL can be analyzed when presented to the probe blade surface on a thin film sandwiched between two thin plastic discs of slightly less than 4 mm in diameter, or other dimension depending on the effective magnetosensitive area of the magnetometer probe.

The use of a thin-film reaction system as just described is highly convenient and yields magnetometer responses that are accurate and rapidly analyzed. Samples and ongoing chemical reactions and interactions can be analyzed according to the invention also when placed simply in proximity to the magnetosensitive area of the magnetometer probe 16, even when the location of the sample is outside the stabilizing jacket 14.

The magnetometer probe 16 is connected to a magnetometer amplifier and control box 18. For a Hall effect magnetometer probe, the control box 18 may house a standard Hall effect amplifier and control system. Control box 18 is connected to a chart recorder 20 or other convenient manner of recording the output from the magnetometer probe.

In the specific experiments detailed herein, the standard Hall effect amplifier and control system was set to have a maximum working range of sensitivity of 20 nano Tesla (nT) [=200 microgauss (μG)] full-scale for display on a laboratory chart recorder. The working output of the magnetometer system is read out on a graph of time vs. magnetic field strength in microgauss, from the relationship 1 nT=10 μG (see FIGS. 2 to 23).

Since differing molecular interactions can be expected to produce time vs. field strength relationships which are characteristic of the specific reactants involved, a Fast Fourier Transform (FFT)-assisted spectral analysis of the unprocessed magnetometer output signal is expected to provide information concerning the nature of the molecular interaction(s) proceeding in the reaction vessel, even long before the reaction kinetics have reached equilibrium. Appropriate spectral analysis provides signature frequency spectra characteristic of specific chemical interactions and substances.

The generation of specific frequency spectra in accordance with this aspect of the present invention enables the identity of an unknown reaction or material to be determined rapidly and accurately. In Table 1 below, there are listed various specific types of chemical reactions which are amenable to identification by such signature spectra, as well as specific applications of this aspect of the invention in studies on biological, biochemical and biomedical phenomena.

The use of a superconducting quantum-interference detector (SQUID) probe can for certain selected chemical reactions and in interactions provide signal-to-noise ratios many orders of magnitude greater than the Hall effect magnetometer probe described here and may be employed in place thereof. Each improvement in signal-to-noise ratio permits the measurement of chemical interactions with progressively smaller reaction volumes. Thus, with the attachment of a SQUID magnetometer probe, the invention would be able to analyze chemical reactions in microscopic quantities and volumes or at great distances from the reacting substances. The latter facility would facilitate the ability of the present invention to be used to detect, identify and analyze non-invasively, in real time, specific chemical reactions ongoing in the interior of the living body, e.g. in humans. Increases in signal-tonoise ratios and smaller reaction volumes also decrease analysis times, since the FFT virtual-filtering routines have thereby less noise to remove. As an auxiliary component or attachment of the present invention, therefore, a SQUID magnetometer probe would provide a non-invasive, rapid, non-confining method of diagnosing metabolic disease states from without the human body.

The invention can be used as a sensor of electromagnetic energy in the microwave region, with a sensitivity adequate to detect microwave emission from chemicals spontaneously emitting or absorbing such radiation without undergoing chemical reactions, at distances of as much as twenty meters from the Hall effect detector element. Such telesensitivity is enhanced by sample-to-detector coupling via waveguide-configured directors and repeaters; a typical configuration of which is shown in FIG. 1b. Waveguide materials of bright-polished copper or ferromagnetic with very high permeability and polished surfaces, considerably enhance detection of microwave signals with the invention. Detectable frequencies ranges from about 1.0 gigahertz (GHz) up to about 20 GHz or higher. A 10 milligram vial of hexamethylenetetramine (HEX), a precursor of the military high explosive trimethylene trinitramine (RDX; No51), at distances of over 10 meters can produce in its resting or ground states spontaneous microwave emission at levels of signal strength that yield an instrumental deflection response equivalent in amplitude to that produced by a static magnetic filed of ca. 50 microgauss at a distance of 2 cm from the Hall effect detector. This sensitivity permits the detection and monitoring of microwave energy originating from small samples of many different species of chemical compounds and from various states of matter either in the presence or in the absence of chemically-driven activation and at distances of many microwave wavelengths, often as may as 100 to 200 wavelengths distant or more. Incremental changes in sample-to-Hall effect probe distance show distance-response relationships with maxima and minima consistent with microwave energies of wide bandwidths, over the range of 1 to 20 GHz or more. These phenomena provide a means of detecting and analyzing chemical events whose activity and specific chemical nature is characterized by microwave radiation in specific regions of the microwave spectrum and which are taking place in reaction vessels, or in the living body or elsewhere at locations remote form the magnetometer detector probe.

The present invention can detect, over a wide frequency range, electromagnetic fields arising from chemical reactions, from matter in the ground state, or from spontaneous inherent quantal fluctuations thereof. The source of the electromagnetic field energy can be very close to the Hall effect detector probe, or may be at various distances away. Sensitivity both to spontaneous and to excitation-dependent emission of microwave fields from matter in any state and over wide ranges of quantity makes it possible, essentially, to detect the presence or absence of matter in any state, to detect, at a distance, the removal or addition of different quantities of matter from or to specific batches of such and to discern changes in the state of matter under observation.

Sensitivity of the invention to microwave field energy was estimated from comparative measurements made by visual inspection of chart recordings obtained from the magnetometer output when the detector probe was irradiated with microwave energy from a Hewlett-Packard HP8673B microwave signal generator with accuracy traceable to NIST or similar standards. The invention was shown to be capable of detecting such fields when the microwave energy reaching the Hall effect detector element is equal to or greater than ca. $10^{-12}$ W effective radiated microwave power over any suitable band of frequencies (e.g. 11.3 GHz+/−10%) between 2 to 26 GHz (FIG. 1c). Hence, spontaneous emission of microwave energy from suitably-situated forms of matter is similarly detected by the device.

Machine measurement of the invention's ability to detect and record microwave (about 2.0 GHz) and very high-frequency (VHF: about 50 MHz) radiant electromagnetic energy was made to diminish subjective errors inherent in visual response estimation. With conventional response-averaging techniques the sensitivity to 2.0 GHz irradiation was 10.0 milliwatts, with +/−3.0 percent error. Sensitivity at 50 MHz was 2.0 nanowatts +/−3.0 percent error, with no response averaging. In one experiment, a sensitivity of 1 picowatt, at 50 MHz, was observed. All energies specified here have been normalized to that measured at the detector probe element.

One practical application of the ability of the invention to detect spontaneous emission of microwave energy from matter and thereby the presence of chemicals at a distance in their ground state at room temperature, is described below. The substance chosen for investigation was hydrazine sulfate, a reactive nitrogenous compound known to be an environmental and workplace hazard implicated in tissue toxicity and carcinogenesis (refs. Wi76, Do80, FO86). The chemical instability of hydrazine presents explosive hazards in its legitimate use as a rocket fuel (ref. Wi76) while the same properties have raised fears that hydrazine might be added to terrorist armamentaria. Detection and identification of hydrazine and its derivatives in ambient air at low levels has proven difficult (ref. FO86).

The ability of the invention described herein to detect the presence of a distant source of hydrazine sulfate was tested by placing 1.5 grams of hydrazine sulfate into tightly-capped plastic vials and placing these singly in the open bell of a broadband microwave horn. The horn was configured to have a low-frequency cutoff in the vicinity of about 15 GHz and was coupled in conventional waveguide-fitting fashion to the Hall effect detector probe. Distance from test vial to Hall effect detector element was about 26 cm. Control conditions for a largely hydrazine-free environment were approximated by similar placement of capped clean, empty, new plastic vials in the bell mouth.

Placement of 15 hydrazine-loaded vials and 15 empty control vials, as described, resulted in downward-sloping output responses; the mean sloping response (rate of change of slope, in arbitrary units) to placement of hydrazine vials in the microwave horn bell was −646 +/−113 (mean +/−S.E.) units while the mean response to similar placements of 15 empty ("control") vials was −46 +/−143 identical output units. The difference was significant (Student's t-test, d.f.=14) at the level of "p"=/<0.01.

The signal-to-noise ratio factor and hence the operational sensitivity of the microwave sensor function of the invention is markedly enhanced by the addition of a broadband stochastic resonance (refs. Be81, Co95) generation system in close but noncritical proximity to the Hall effect detector probe. One effective embodiment of such a stochastic resonance generator consists of an aperiodically-rotating circular tray of randomly-oriented metallic objects, chemical samples and radioactive sources of variegated strengths. Dimensions of the stochastic resonance generator are small compared with total size of the remaining components and accessories comprising the invention.

Another effective means of signal enhancement via stochastic resonant phenomena consists of the simultaneous recording of signals originating in spontaneous emission of radiant energy from matter in any of its ground states during excitation of the Hall effect detector with microwave energies over the ranges of about $10^{-12}$ W to about $10^{-3}$ W at frequencies ranging from about 2 to about 26 GHz.

In complementary fashion, attachment of a SQUID magnetometer probe to the invention would enhance the sensitivity of the device to these phenomena by many orders of magnitude.

The addition of a simple static or slowly-varying magnetic field generator to the device, alone or in conjunction with a SQUID magnetometer, permits the present invention to function as an electron spin resonance (ESR) spectrometer and thereby discern molecular structure without requiring the chemical sample to be submitted to microwave or other propagating radiation. One condition where this would obtain is during a chemical reaction involving known or unknown molecular entities. The structure-discerning result is achieved because the pattern of microwave signals from chemically-reacting molecules in a magnetic field changes with imposed magnetic field strength in unique fashion for individual molecules. Such application of the invention can with convenience be further enhanced by attaching to the magnetometer probe a semiconductor Peltier-effect thermoelectric cooler, with appropriate electronic control system. This facility permits the analysis of chemical structure at cryogenic temperatures, a circumstance which reduces the rotation of protons around single bonds in the molecule of interest, thereby permitting more accurate representation and resolution of molecular conformation. The extension of the invention to provide a nuclear magnetic resonance facility involves merely the addition of the necessary magnetic field coil(s) and control system to the magnetometer probe.

The practical shortest analysis time for the generation of a specific frequency spectrum from a given procedure is approximately ten times the period of the lowest frequency present in the frequency bandwidth chosen for analysis. With the small volumes and reactant concentrations necessary for achieving results using the present invention this lower limit may approach no more than about one to two minutes. Spectral or other modes of analysis, for example pattern recognition and waveform-trend forecasting, can be accomplished with a user-programmable digital computer which stores the unprocessed signal, the analyzed result and experimental notations on magnetic media. Outputs of all stored modes can be displayed, as chosen, on the computer screen. These outputs can then be compared by visual and statistical means with response patterns previously obtained from known reactions under controlled conditions or derived from theory. Thus, general and specialized libraries of spectral and response pattern data can be built up as the invention is utilized in an individual laboratory or can be compiled from variegated laboratories in several different areas of investigation. An expert system would be available to assist the investigator with the interpretation of results.

The detection device of the present invention utilizes the Hall effect features of the specially suitable semiconductor, namely gallium arsenide, that has been determined to be sensitive even to very weak electromagnetic fields over a very wide range of high-frequency electromagnetic fields propagating at the speed of light. Furthermore, the detection of weak signals is enhanced via stochastic resonance, a ubiquitous, natural phenomenon, where an increase in the signal-to-noise ratio at the sensor is effected by the presence of background noise having appropriate signal characteristics.

The sensor responded robustly to a picowatt ($10^{-12}$ watts) of an 11.3 GHz microwave signal, emitted by a commercial microwave generator 60 cm distant form the detector. The sensor also yielded relatively large output responses when subjected to very high frequency (VHF) radio signals from a domestic infant monitor, located in an adjacent room and generating signals calculated to impose an estimated $10^{-9}$ to $10^{-12}$ watts of 50 megahertz power at the sensor surface.

The detection of weak electromagnetic radiation emitted by chemicals is one application of the invention. Others are described below. The detector is a "passive" receiver of microwave signals, i.e. there is no requirement for application of an energy source, for example, radiation, to activate the chemical substances. The chemicals are detected even when in containers, including, for practical purposes, even those made of metal, and placed remotely. This latter capability can be ascribed to induction of eddy currents on conductive enclosure walls and on nearby rod-like metal structures, with establishment of virtual oscillating dipoles and consequent resonant propagating reinforcement of the original signals. The inherent ability of a semiconductor Hall effect device to sense electromagnetic energy emitted by non-excited (ground state) chemicals has not been exploited previously in adverse non-laboratory environments.

Chemical compounds at room or even much lower temperature comprise atoms with some proportion of electrons in excited states. Chemicals that form the basis for explosives, or are precursors in the synthesis of explosives, tend to be reactive, hence incipiently unstable, compounds. Electrons in such compounds emit microwave energy extra-atomically as they move spontaneously about differing intra-atomic energy levels within their atoms. Thus, the atoms that constitute explosives contain relatively more electrons in excited states than do more stable compounds and presumably tend to emit more radiant energy. Studies with hydrazine ($H_2NNH_2$), an explosive rocket fuel, among other uses, and potassium perchlorate ($KClO_4$), a highly corrosive oxidizing agent used in the illegal manufacture of explosives, including fireworks and terrorist devices, have been made. On a weight basis, perchlorate is more effective than hydrazine and much more effective than, for example, sodium chloride, with respect to activation of the Hall effect sensor.

Signals from the sensor are amplified by a Hall effect magnetometer with carrier-amplifier circuitry. Initially, acquisition and characterization of signals generated by the detector may be effected by chart recordings displayed on a rectilinear chart recorder, as seen in FIG. 1. This method is not ideal for determining frequency-response characteristics, although invaluable for critical visual inspection. A computer-screen display of simulated virtual chart recording may be employed and is more convenient and versatile.

The activation of the sensor by the presence of a chemical substance placed remotely may be expressed on a chart recording in a number of characteristic patterns, as may be seen, for example, in FIG. 1c. (a) at the beginning of a response to initial placement of a chemical sample the ("ON" response), there tends to be a "denser" baseline trace during such activation, i.e. one with smaller, more rapid excursions in the recorded signal, (b) emergence of a gradual slope in baseline mean position with time, and (c) a peak of the slope magnitude occurring two to three minutes after initial exposure to sample, (d) when samples, in contrast to controls (i.e. containers lacking the chemical), are present for long periods and then removed, the "OFF" response emerges: there may be an abrupt change in the slope of the recording, followed by the densest areas of the pen/trace movement observed over the entire recording.

The features of the chart record that accompany exposure of the sensor to an active sample have been utilized as a basis of mathematical analysis that demonstrates objectively the ability of the sensor to distinguish a chemical sample from an empty container. Statistically-significant differences in sensor responses have been found between chemical samples and control (blank) samples with respect to the quantitative determinations of highly reproducible features of the chart recording usually observed, viz: slopes of the ink trace, confidence limits for the range of voltages, mean voltages, and the number and size of dense areas in the record. Moreover, these significant differences were obtained in the context of several unrelated variables, e.g.: type of chemical compound, time of exposure, time of test over a several-week period, distance of specimen form the sensor, sequence of applications of test and control samples, nature of the container, and utilization of two different sensor instruments situated at highly-separated locations on two different floors in a large building.

The reproducible feature of the sensor's response to chemical samples may be used to "train" a computer "neural network" program (based on known mechanisms for transmission of information in the human brain), to distinguish chemicals from the control samples. In preliminary studies, a trained network has been successful in identifying concealed samples of hydrazine sulfate, with a mean success rate of 61.9% and a mean of 58.8% success rate for controls (empty containers, or a non-reactive chemical). The 121/200 success rate represents an odds ratio of greater than 100:1 against this rate occurring by chance alone. It is highly likely that much higher success rates would have been achieved, had the available data been processed by individual experienced in neutral net analysis.

DESCRIPTION OF FURTHER APPLICATIONS OF INVENTION

This patent application is concerned with all applications of the principles described herein, for the detection or analysis of chemical reactions, molecular interactions, radioactivity and changes in state of matter, including the formation of plasmas, polymers, spin glasses (ref. Vi77), liquid crystals and phase transition in gases, liquids, solids (ref. Si82) and colloids constituted from all states of matter.

The present invention, in addition to the specific uses described above, is useful for the detection, characterization and measurement of microwave and other propagating electromagnetic energies arising from:

(1) Free radicals, in solution or in gaseous, liquid, sol or gel colloid suspension, whether stationary or in motion relative to the magnetometer probe.

(2) All chemical entities with unpaired electrons or with asymmetric nuclear magnetic momentum, whether stationary or in motion relative to the magnetometer probe.

(3) Chemical reactions, especially those in enzymatic pathways, within the living body, by means of a magnetometer probe attachment of suitable shape, size, and adequate sensitivity and signal-to-noise ratio, whether the reaction and molecular interaction is under intended observation, are the result of ongoing bodily activities in health or disease or are stimulated to CRIM magnetosynchrony by the administration of exogenous substances, such as specific substrates for chosen enzyme systems or by the application of electromagnetic energy, such as bioluminescence either coherent or noncoherent, coherent light, such as laser energy, electromagnetic fields at any frequency or by ultrasonic, thermal or mechanical energy.

(4) Chemical reactions and molecular interactions observed in vitro in tissues excised ethically from plants, insects, animals, patients and their controls, in order to distinguish healthy from diseased tissue and under experimental conditions as described above.

(5) Industrial effluent gases, liquids, solids and suspensions, whether colloidal, quasi-colloidal or crudely macroscopic systems.

(6) Magnetic field patterns to be used in seeking fossil fuels, whether gaseous, liquid or solid; underground water and its variant solute-modified constitutions; underground pollutants, especially those hazardous to underground workers, the hazardous to include coal dust, explosive gases and toxic gases; specific rock formations indicating species of ore, fault lines and tectonic formations and hazards, solid or liquid pollutant substances in soil, groundwater and aquifers.

(7) Electromagnetic field patterns predictive of impending earthquakes and other massive tectonic or geothermal events.

(8) Chemical reactions and molecular interactions in oceans, rivers, lakes and reservoirs where analysis or detection of the chemical reactions can yield information concerning ongoing or incipient environmental pollution hazards.

(9) Chemical reactions and molecular interactions in soil, where analysis or detection of the chemical reactions can yield information concerning the ongoing biochemical activity of soil organisms and concerning ongoing or incipient environmental pollution hazards.

(10) Chemical reactions in industrial processes where on-line information in real time is desired concerning the kinetics and phases of continuous chemical reactions in the ongoing batch or bulk process with the object of automating and regulating the process for optimal productivity and quality. In reactions of all kinds, the abilities of the invention will detect and identify intermediates in the total reaction process, in laboratory micro-, bench-top and industrial-scale batches. The present invention, being particularly useful for monitoring the reaction rates and kinetics of polymerization reactions since the formation of polymerizing bond structures generates molecular magnetic domains similar to those found in magnetized mineral and ferrite substances, may be used also for real-time detection and monitoring of polymerization processes.

(11) Incipient and ongoing ice formation in shipping ports, on rivers and in lakes, on highways, roads and rail lines, on surface vehicles, especially on windscreens and windows and on wings, ailerons, cowling, wheel fittings and other ice hazard-sensitive areas of aircraft and spacecraft.

(12) The ability of the invention to distinguish between the presence of heavy water (deuterium oxide; $D_2O$) and ordinary water (hydrogen oxide; $H_2O$), either in samples at distances from the magnetometer probe, or in its close proximity.

EXAMPLES

Example I

The devices illustrated in FIGS. 1a and 1b have been employed in the generation of charts depicting the time course of various reactions carried out in the reaction vessel 10 and these charts are shown in FIGS. 2 to 23. The specific reactions and conditions are outlined in the figures using certain abbreviations and are tabulated in Table 3 below. Examples of some biochemical pathways identified by the device of FIG. 1a and shown in certain of the FIGS. 2 to 23 are detailed in Table 2 below while specific identification of experiments depicted by FIGS. 2 to 23 is shown in Table 4 below.

Example II

The devices illustrated in FIGS. 1a and 1b have used to study hydrazine sulfate and potassium perchlorate. Simultaneous recordings were made with pen-and-ink recorders and with computer-display virtual chart recorders. For the studies with hydrazine, a glass container of chemical or an empty container (control) was placed at varying distances from the sensor, from a few inches to several meters, and for periods of time varying from 1 second to 240 seconds. The bottles were placed in cardboard containers. Computer-displayed representations of the chart record were virtually identical with respect to the features of the chart record itself in response to hydrazine (see FIG. 24): an early "ON" density, a gradually developing slope reaching a peak after several minutes, a more condensed consolidation or "tightening" of recorded fluctuations, a reversal of the slope towards the original baseline when the sample is removed (beginning of the "OFF" period), with the most dense part of the record occurring during this reversal or OFF period.

Usually, more pronounced effects were seen in the record when repeated "ON" and "OFF" sequences were performed manually or with a rotating metal shield placed between a sample and the sensor. The shield had areas cut out and its speed of rotation could be adjusted to vary the duration of the ON and OFF phases. The overall features of the record, however, were similar to those seen with exposure of samples for a finite, uninterrupted time of exposure.

Figure 25A:
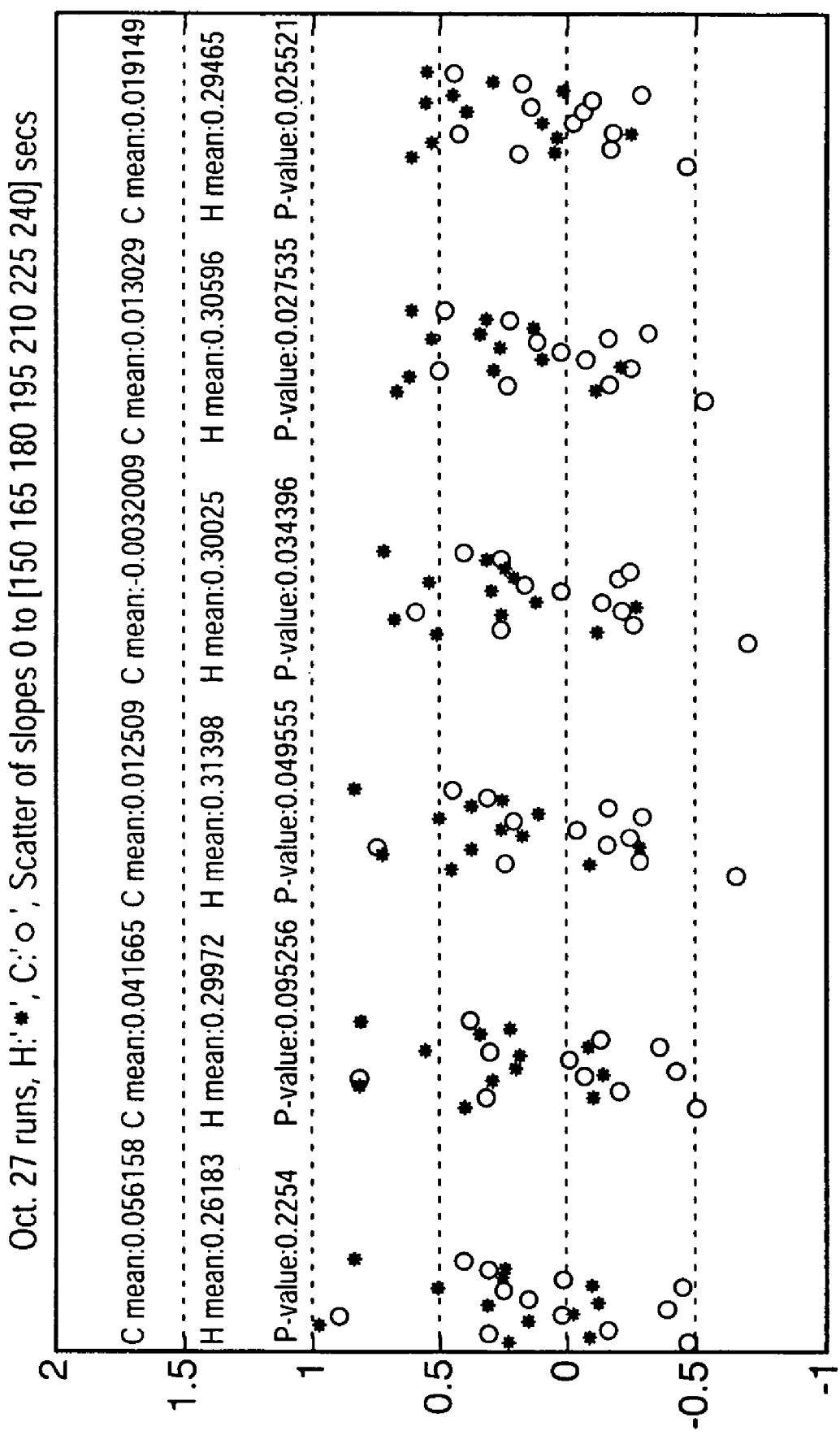
FIG. 25 shows statistical comparison between test and control for recording slopes and for confidence limits which indicate the general range of pen excursions from the baseline in the experiments depicted in FIG. 25. To generate this FIG., the 300-second time course of each run was divided into six 50-second windows; mean slopes (upper panel) and mean 95% confidence limits (lower panel) were determined for hydrazine (*) run and control (o) runs.
Figure 25B:
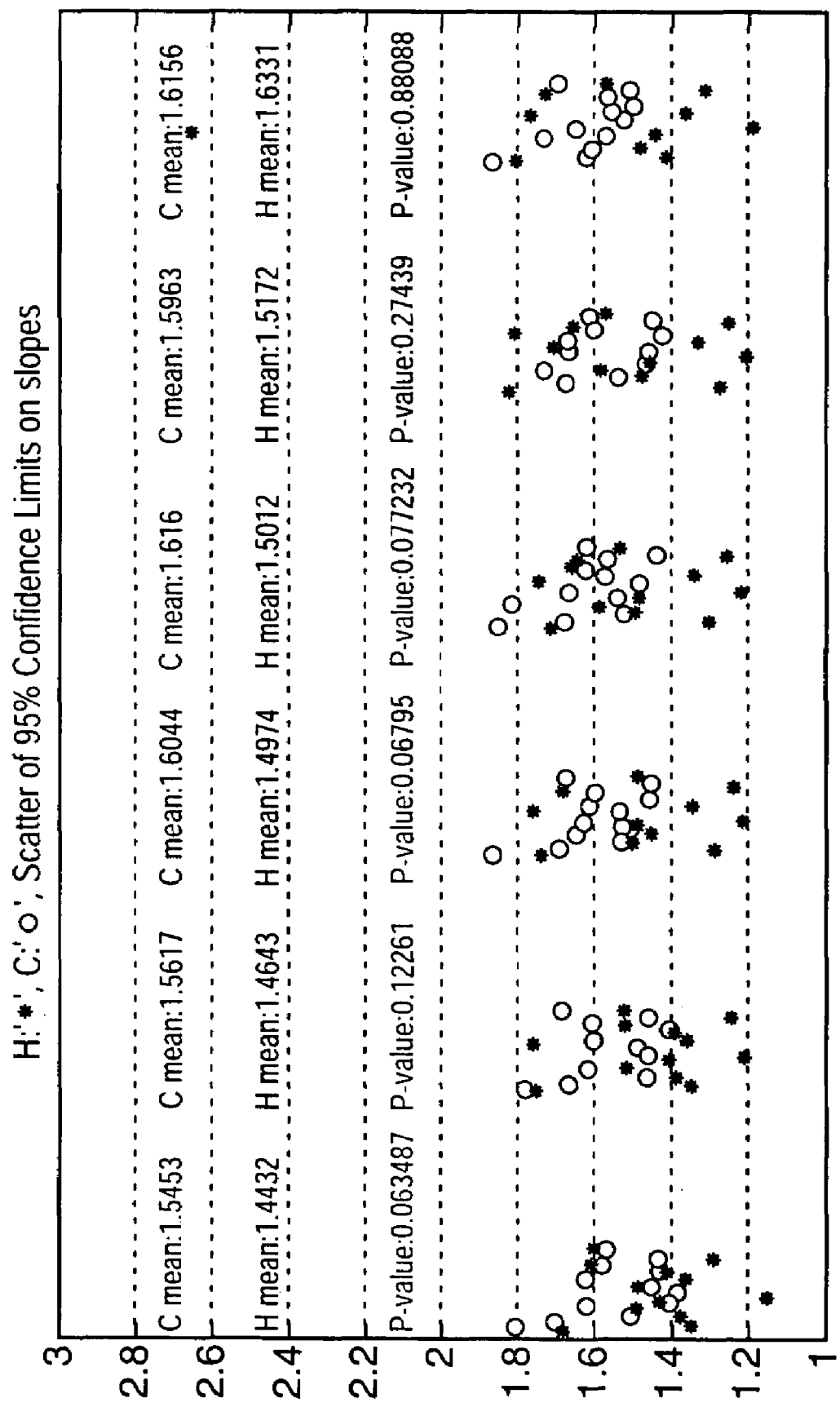

In the statistical analysis of these results for the first set of experiments presented in FIG. 25, for the slopes of the responses, P values of the differences between hydrazine and control runs range between 0.025 and 0.098 for the five periods after the first. These values indicate the significantly greater slope values that occur when the sensor is exposed to hydrazine rather than to control. For confidence limits, P values of 0.07 to 0.12 occur for the first four 50 second periods of the response, i.e. the hydrazine records are less divergent than the control (showing lower 95% confidence limit values).

Figure 26A:
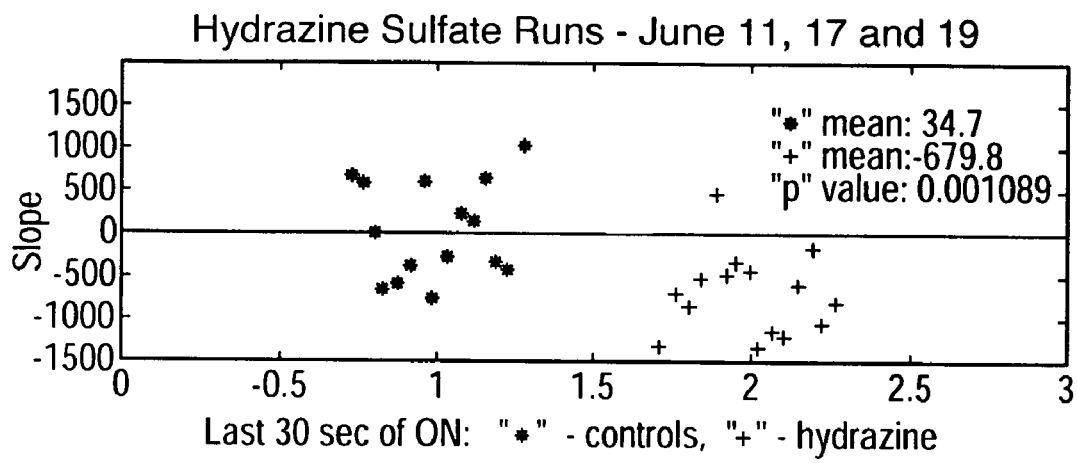
FIG. 26 shows a further set of experiments from those reported in FIGS. 24 and 25 showing values for slopes of the sensor responses, representing changes in baseline voltage, for hydrazine as compared to controls.
Figure 26B:
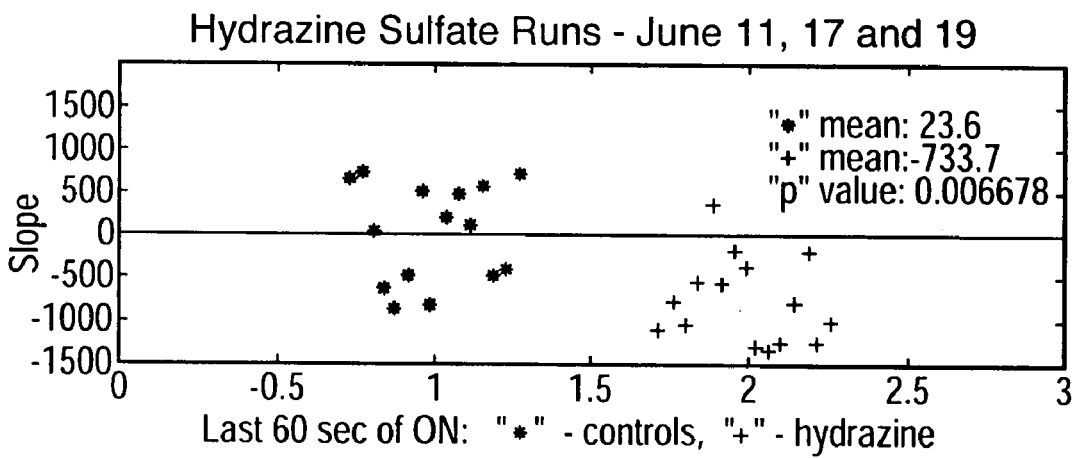
Figure 26C:
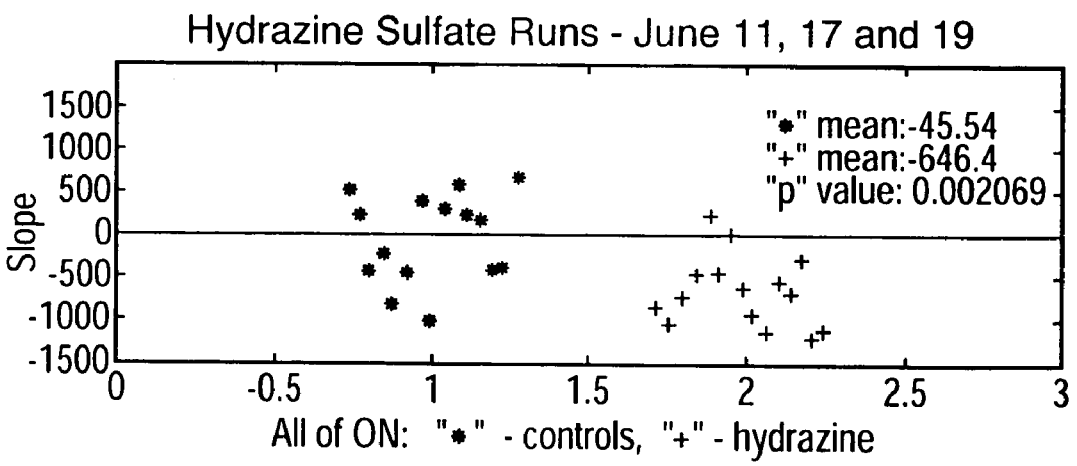

In generating the data shown in FIG. 26, control (a 2-inch high empty vial) or chemical (about 2 grams of hydrazine sulfate) was placed, in non-systematic order, in an aluminum can near a microwave horn attached to the sensor-holder and dynamically coupled to the detector. The can was placed on a shelf which had a plastic cap to provide a complete enclosure for the sample holder containing chemical or empty vial. The analysis measures the arithmetic mean of the detector/gaussmeter output signal over various time periods. This reflects the change in voltage produced when the electrons within the detector element are induced to migrate and establish a Hall potential.

"Scatter" diagrams show the distribution of the values for each of the test and control runs. Different time intervals were used to determine the voltage means. Note the highly significant difference in voltages between test and controls for either the last 30 or 60 seconds of the 4-minute ON period with the sensor exposed to the test samples. The average voltage mean for control "ON" period was 165 microvolts. As seen in Table 6, the large change in voltage between hydrazine ON and hydrazine OFF, when the chemical is abruptly removed from the proximity of the sensor. For the hydrazine, the mean was −1344 microvolts. The mean was negative, i.e. a relatively large digression to the right on the chart. Note the absence of statistical significance between control on vs. control off (high P value) as compared with high statistical significance (low P values) between hydrazine on vs. hydrazine off. In other words, the sensor demonstrated a clear change in response to the electromagnetic environment when the hydrazine was relocated.

Example III

Figure 27A:
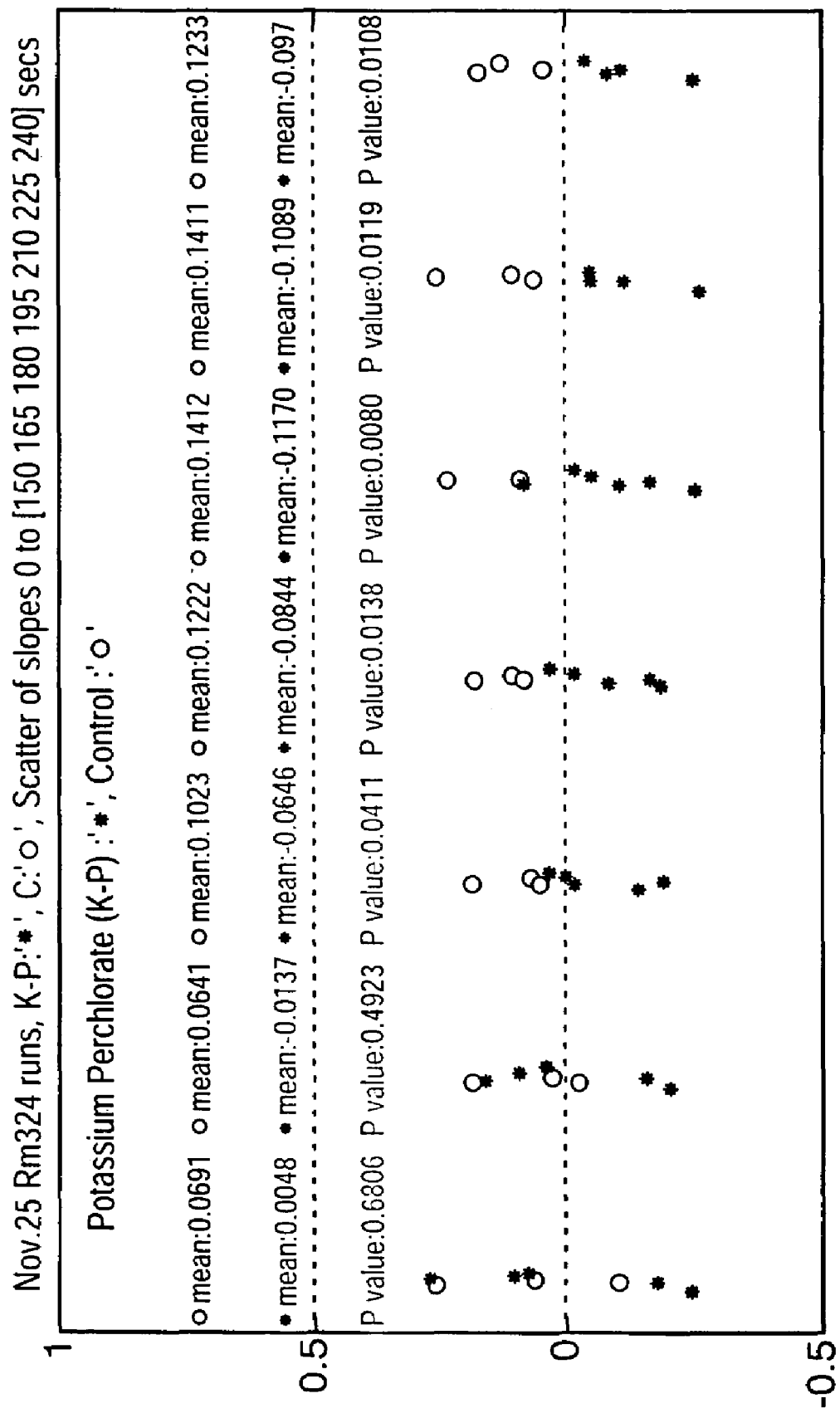
FIGS. 27 and 28 are "scatter" diagrams showing the significances from control slopes and confidence limits, range of magnitudes of pen excursions, in microvolts, generated by samples of potassium perchlorate.
Figure 27B:
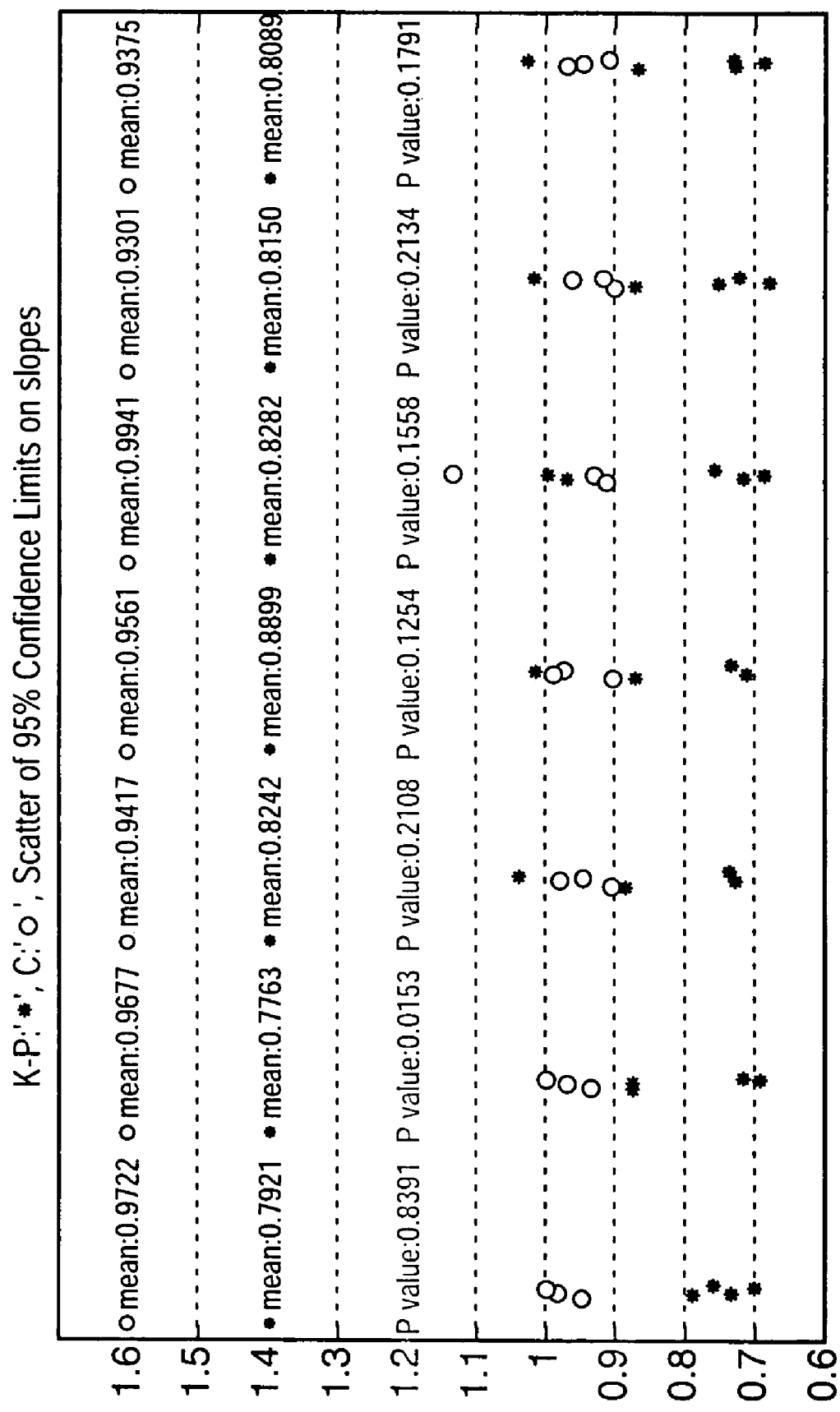

The experiments described in Example II were repeated using potassium perchlorate in place of hydrazine sulfate. The results obtained are depicted in FIGS. 27 and 28.

The columns represent periods of time after a 10-second application of the sample at the sensor. In an experiment presented in FIG. 27, significant differences in slopes and confidence limits occur between chemical samples and controls. The slopes for hydrazine are more negative (the chart record digresses to the right with time), and the confidence limits smaller, for hydrazine runs (generally smaller excursions of the pen with time).

Figure 28A:
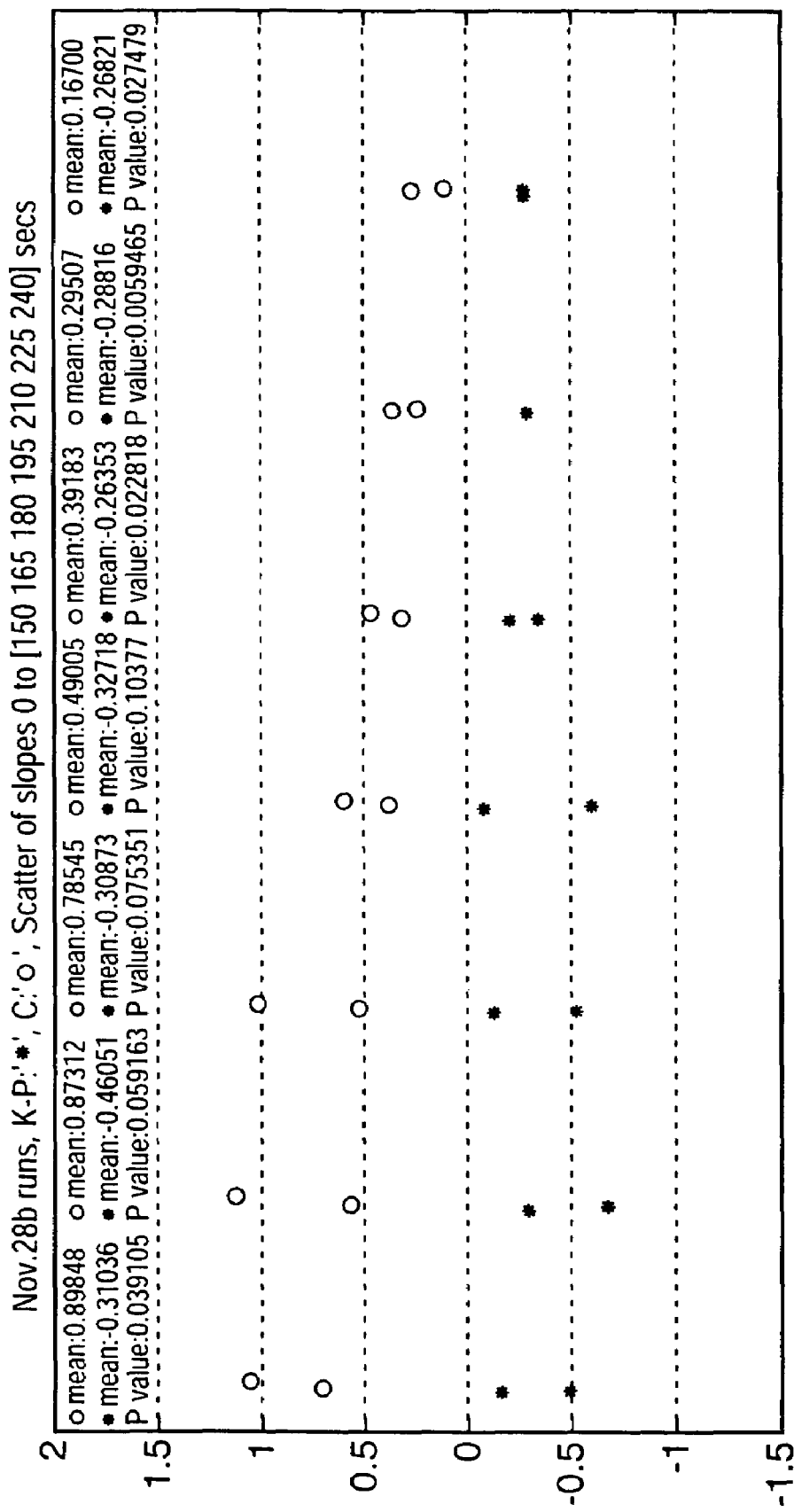
Figure 28B:
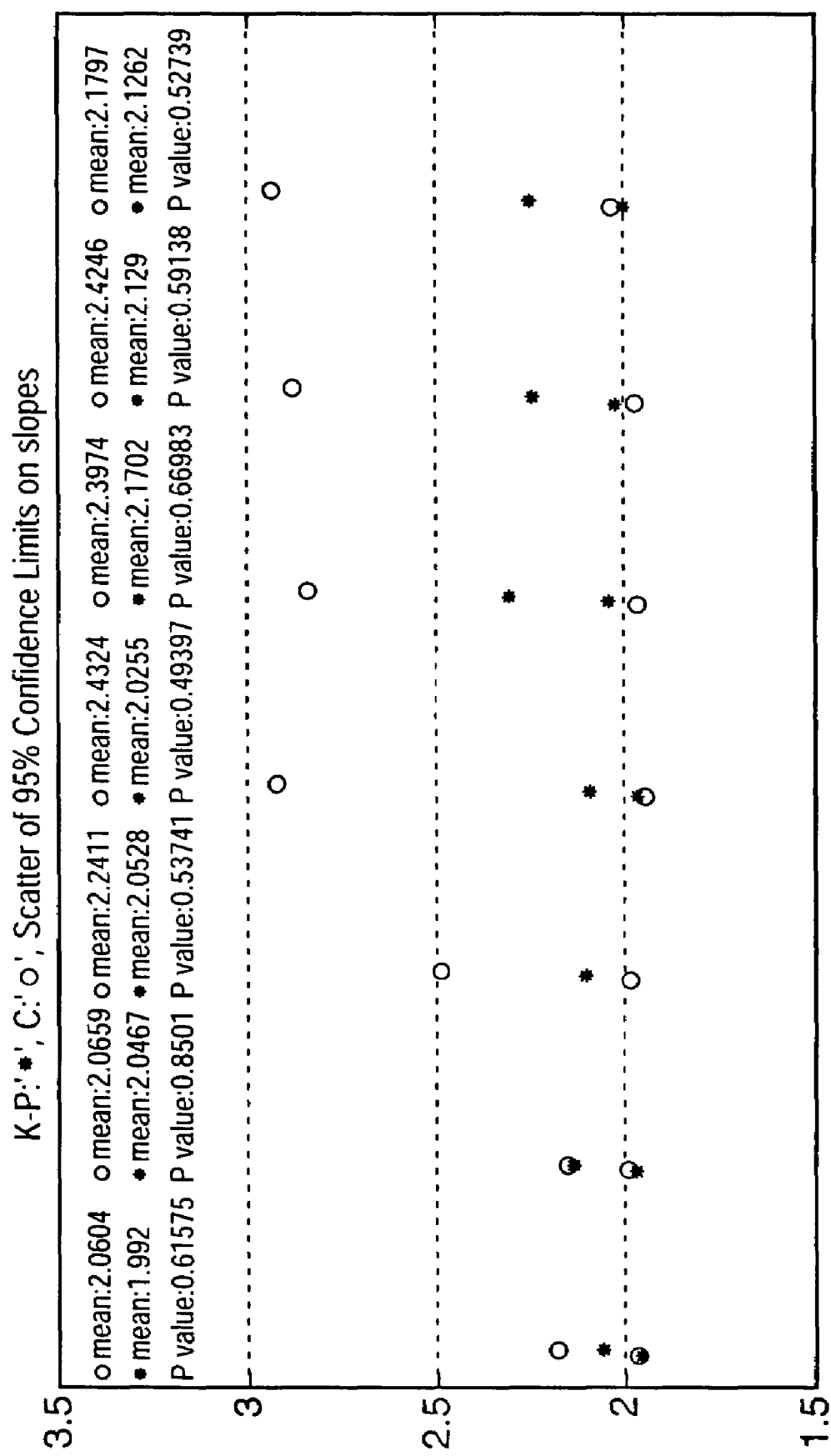

In another experiment, FIG. 28, with fewer individual runs, the perchlorate records, again, showed significantly greater negative slopes, but no significant difference was seen in confidence limits.

FIG. 29 contains a quantification of regions of ink density in the chart record. A computer-generated facsimile of the chart record is shown in the left panel (A). At the right (B), the same record is shown with elimination of recording densities having areas below an arbitrary threshold. The numbers of densities within a certain range of sizes (areas) are determined. Data obtained by this procedure are presented in Tables 7 and 8 for hydrazine and perchlorate respectively.

As discussed earlier, the presence of a chemical substance influences the detector system so that the response of the pen to signals generated by the gaussmeter-amplifier system results in areas of more concentrated pen activity, i.e. dense areas of ink, which we have termed "densities". The columns in Tables 6 and 7 are as follows:

$1^{st}$: the total amount of density in a 4-minute period $2^{nd}$: the number of densities in a 40-minutes period $3^{rd}$: the mean size (area) of the densities (column 1 divided by column 2)

$4^{th}$: the number of trials

Each column has two sub-columns labelled C and S, the means of the Control runs and the actual Sample (hydrazine) runs, respectively.

In general, it can be seen from these Tables 6 and 7 that the total area of density and total number of densities behave inversely, the larger the one, the smaller the other, the wider the densities, the more they overlap and merge, so that there are fewer individual densities.

The postulate, based on visual inspection of many chart records, is that there is more total density for hydrazine samples than for controls. Thus, the S sub-columns should be larger for Total and Mean Size, and the C sub-column larger for Number.

Potassium perchlorate was used as the sample on two quite different systems. For instrument 405, the results again bore out the prediction, with the most significant result coming in the Number column. There were 8 out of 8 days where the higher number of densities was for the control runs. The odds against this happening by chance alone are 256:1.

For instrument 324, the overall amount of density of the recording was greatly reduced and the expectation that Total Density and Number of Densities behave inversely does not appear to apply. Thus, the first column does not match the postulate. However, the Number and Mean Size columns do. The best result again is for the Number column, with 6 out of 6 days showing the higher number of densities in the control runs. The odds against this happening by chance alone are 64:1.

The results with hydrazine over 29 different days follow the prediction for all three columns. The odds against seeing 21 or better out of 29 by chance along are at least 100:1. If the results from the 2 systems are pooled, the prediction is matched 8/14 times for the Total density, 14/14 times for the Number of densities, and 11/14 times for the Mean Size of densities. The most significant result, 14/14, has an odds against ratio values of 16,384:1.

Example IV

This Example provides a clear visualization of the changes in pattern of the ink trace, representing sensor output, to permit a better application of the relative magnitude and time course of events initiated by test materials.

As previously noted, the pen movement of the recorder reflects changes in the output voltage, produced when electrons within the detector element, namely the gallium arsenide crystal, are induced to migrate and establish a Hall potential. The mechanically-operated pen recorder is limited to low-frequency signals, which represent only a small fraction of the total sensor output. Nevertheless, clear and consistent changes in chart recordings occur when the sensor is exposed to samples of chemicals, including radioactive substances and biological and non-biological chemical reaction system. Samples containing passive matter, chemical reaction system or radioactive materials all induce consistent features in the chart record, namely changes in pattern in the ink record, changes in slope of the ink record and the development of small, circumscribed, dense areas in the record, the latter feature reflecting a change in signal frequency.

The visual features of the chart record that accompany exposure of the sensor to an active sample have been utilized as a basis for mathematical analysis that demonstrates objectively the ability of the sensor to distinguish a chemical sample from an empty container, as set forth in Examples II and III. As may be seen therein, statistically-significant differences in sensor responses were found between chemical samples and control (blank) samples with respect to the quantitative determinations of highly-reproducible features of the chart recording, usually observed, namely slopes of the ink trace, confidence limits for the range of voltages, mean voltages and the number and size of the dense areas in the record. Moreover, these significant differences were obtained in the context of several unrelated variables, for example, the type of chemical compound, time of exposure, time of test over a several-week period, distance of specimen from the sensor, sequence of applications of test and control samples, nature of the container, and utilization of the different sensor-amplifier instruments situated at highly-separated location on two different floors in a large building.

In a further series of experiments, a mason jar half-filled with ordinary sand was placed, for a few seconds, near a microwave horn antenna tapering towards the sensor situated about 130 cm distant and served as control. Two other jars, one containing several grams of manganese phosphate mixed into the sand and the other containing several grams of beryllium sulfate mixed into the sand.

In this further series of runs, each Figure comprises three replicates of a single chart recording. In such case, the bottom trace has a line through the estimated mean of the baseline control period, i.e. the trace prior to the introduction of the test sample (at the arrow) for a specified number of seconds. In the case of the bottom trace, this line is extended into those regions of the trace where a response to experimental intervention was anticipated.

The middle trace shows slopes throughout the baseline and test periods. The envelope of the upper trace is shaded in order to show more clearly both the variability in the pen excursions (changes in voltage) and number, areas and distribution of dense regions ("densities") in the pen trace.

Figure 30:
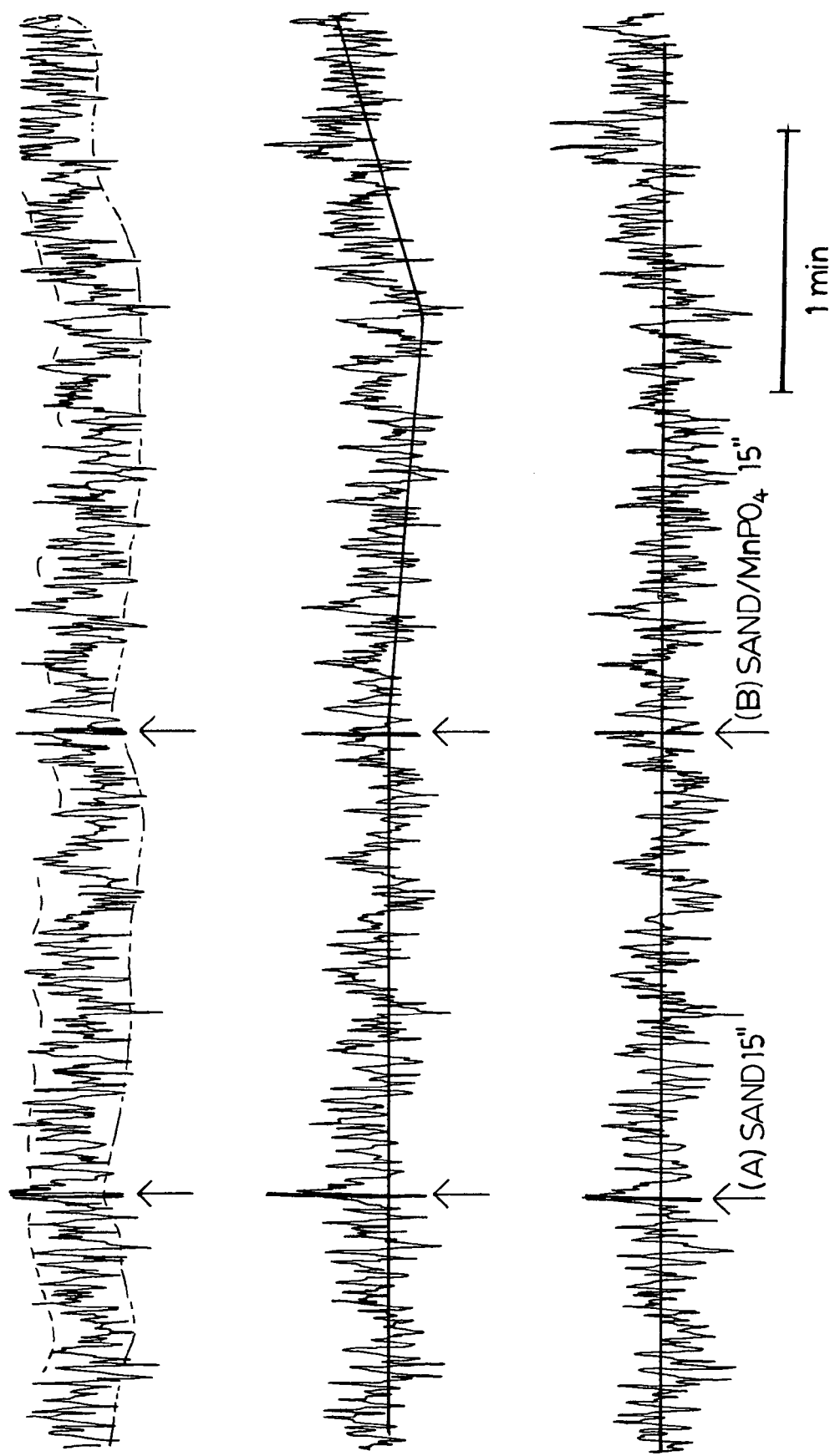
FIGS. 30 to 49 show the results of series of experiments conducted with passive material.
Figure 31:
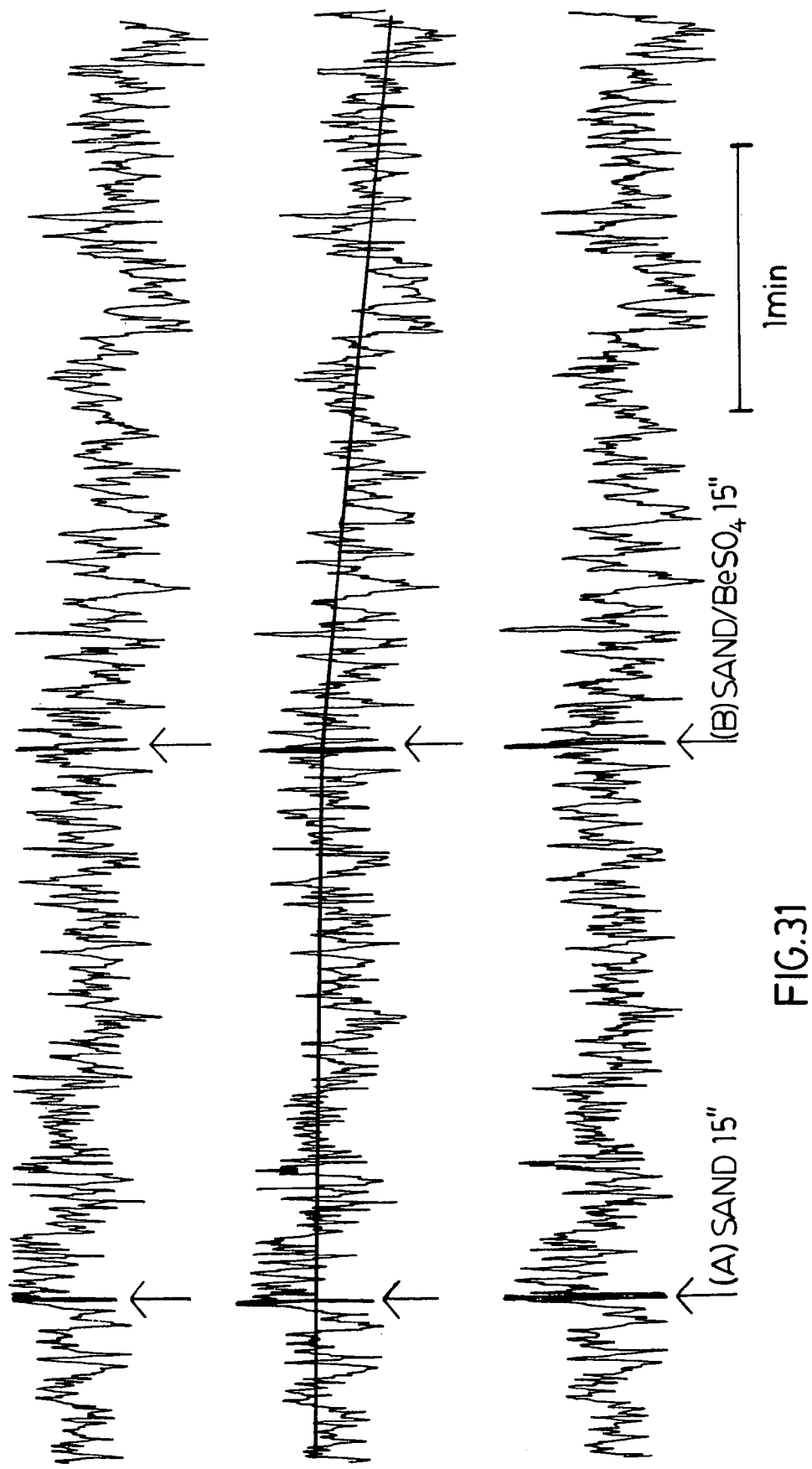
Figure 32:
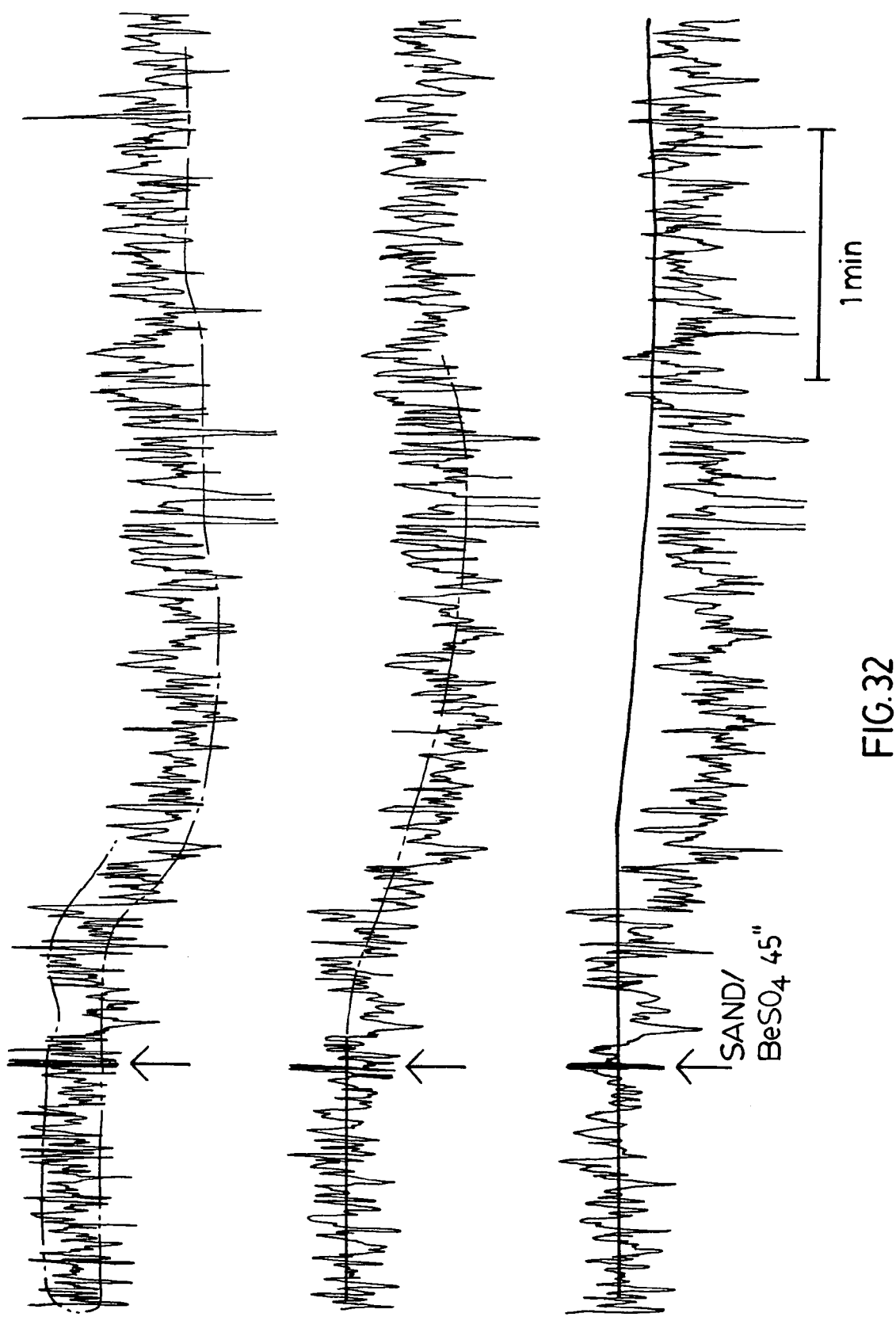
Figure 33:
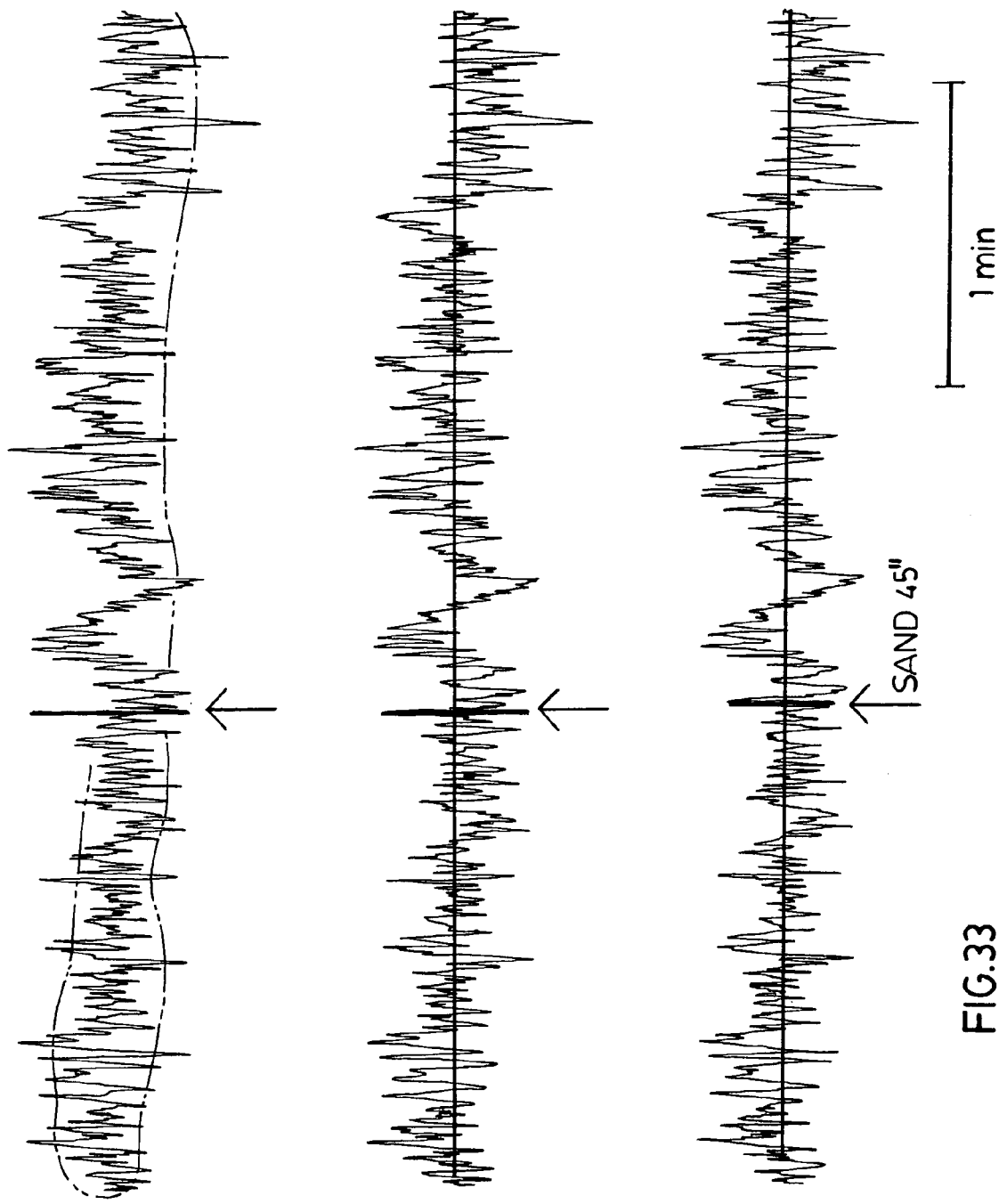

These results of the further series of runs are shown in FIGS. 30, 31, 32 and 33. FIG. 30: The sand alone (arrow A) causes only a slight change in the pattern of the ink trace. Sand plus manganese phosphate (arrow B) causes a clear, sustained change in the pattern after a delay of ca. 1.4 min. The record is more dense where spikes in the trace cluster together, and output voltage fluctuations in either direction from the baseline are smaller. FIGS. 31 and 32 (sand plus beryllium sulfate) show sensor responses similar to those with sand plus manganese phosphate. FIG. 33 shows the minimal effect of sand alone.

Figure 34:
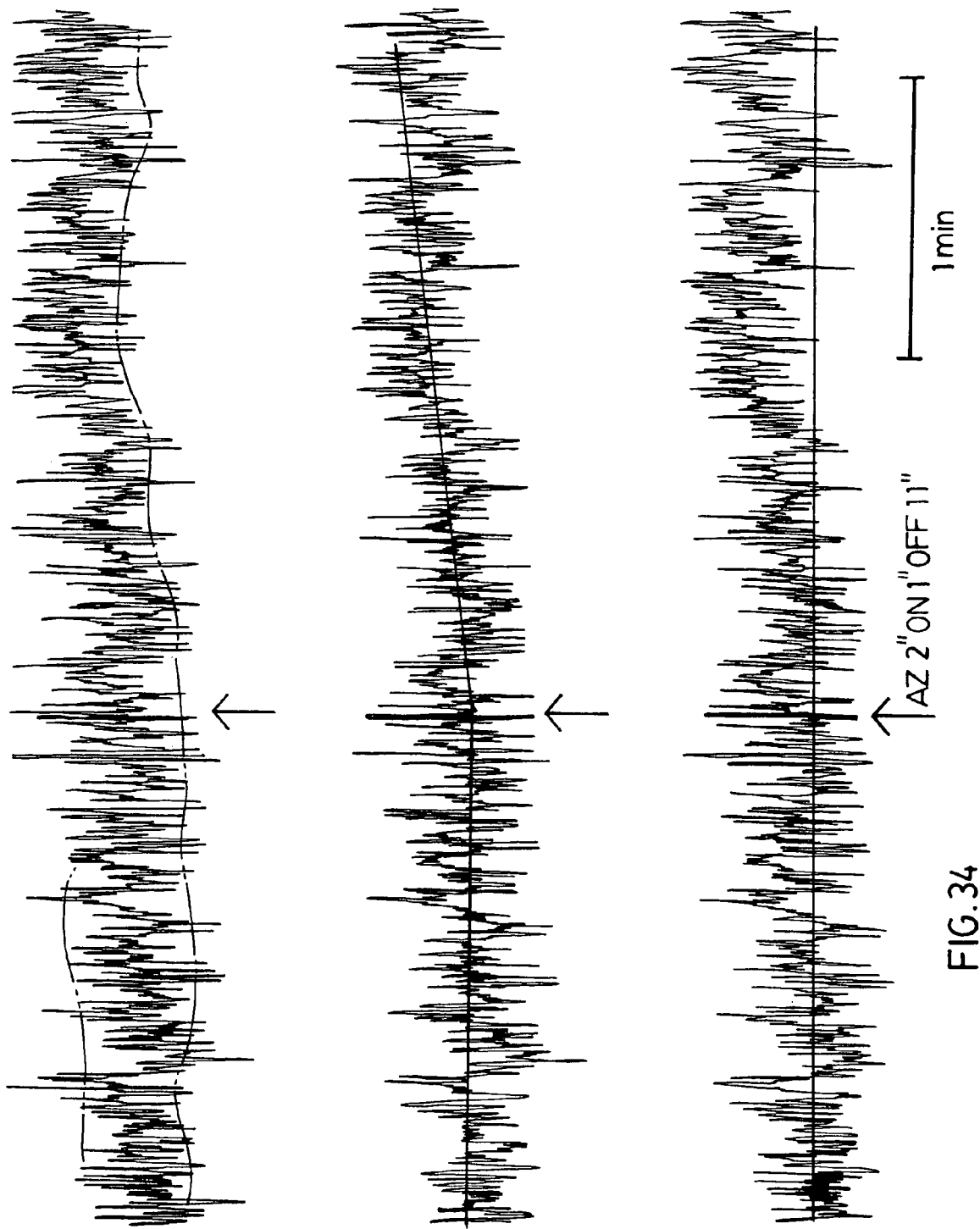
Figure 35:
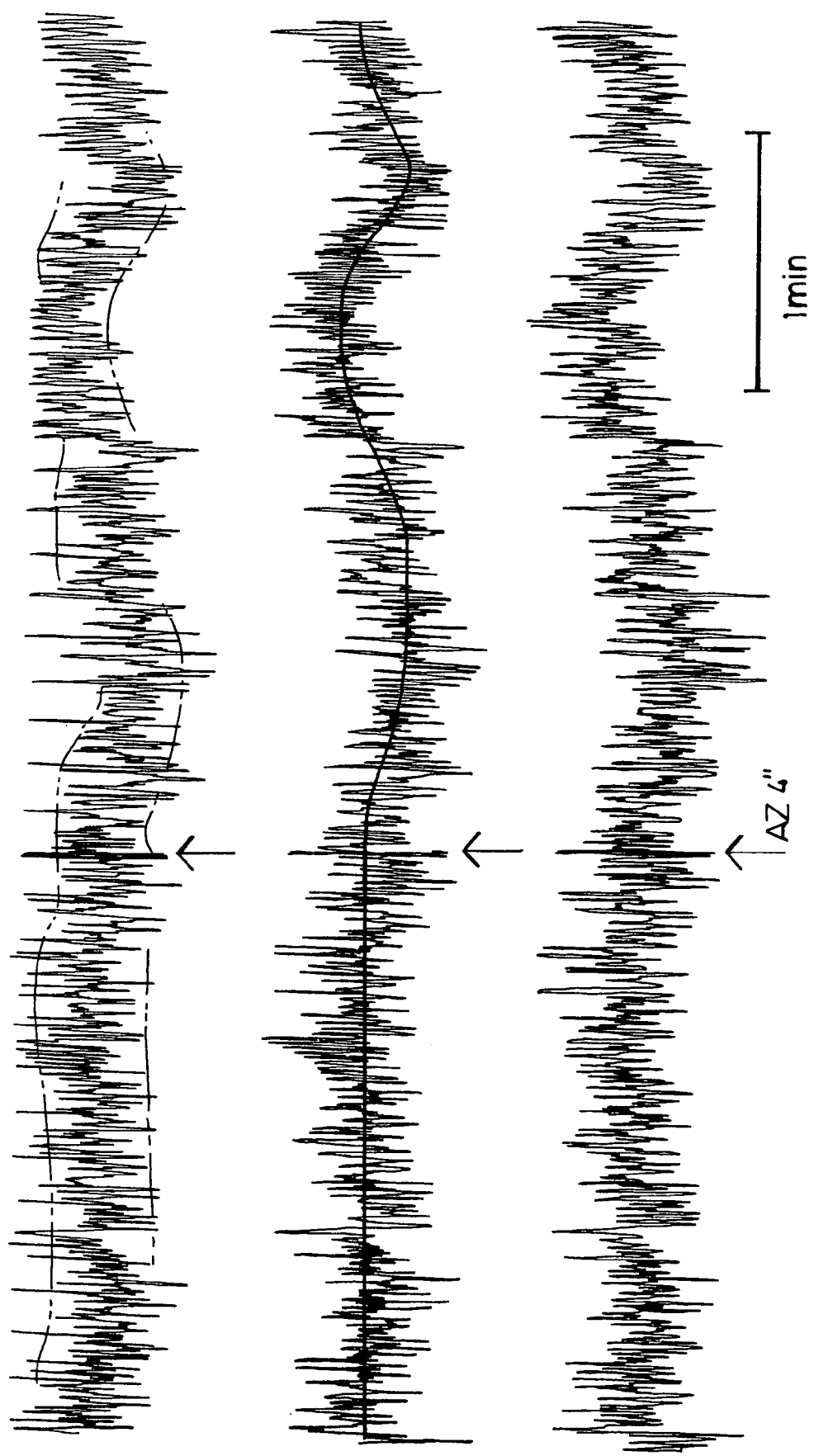
Figure 36:
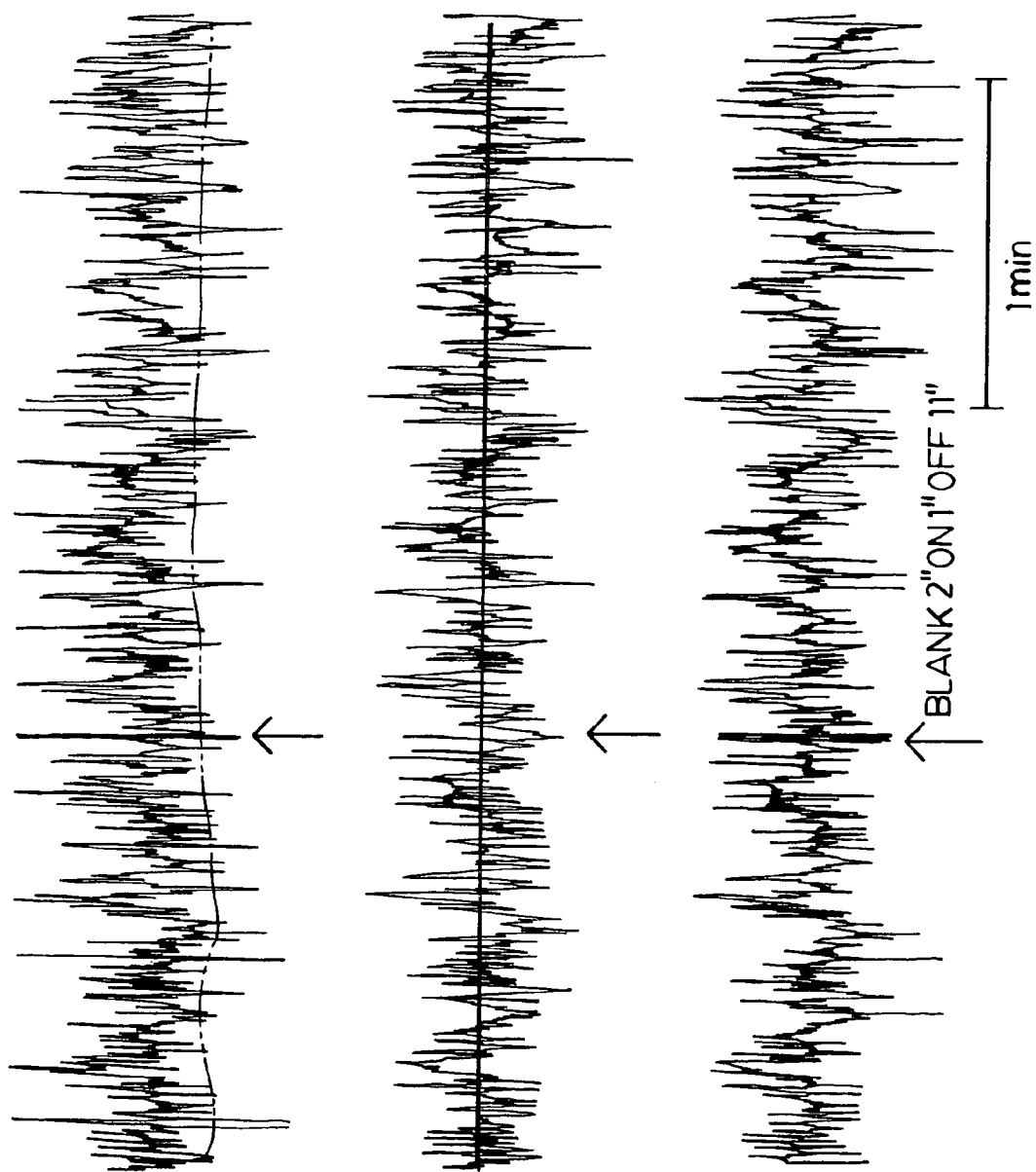

In one series of runs, a dark-glass bottle of sodium azide (AZ) or a similar but empty bottle is placed a few inches from the detector for a few seconds and then removed. Within a few seconds after removing the test material, there occurs a change in pattern and/or slope of the pen trace. The effect persists for several minutes, the pen record eventually returning to the original baseline and pattern. The results obtained are recorded in FIGS. 34 to 36. FIG. 34 shows a baseline segment prior to placing the bottle of sodium azide (AZ) near the sensor. The AZ was placed near the sensor for 2 seconds and removed for 1 second, repeated 4 times. FIG. 35 shows a response to AZ placed at the sensor for 4 seconds continuously. This overwhelming response is seen with any test material that, in quantity or in duration of placement at the sensor, clearly exceeds the levels of activation that are needed to induce a trace with a continuous slope in one direction. Response to an empty vial (BLANK) is seen in FIG. 36.

Figure 37:
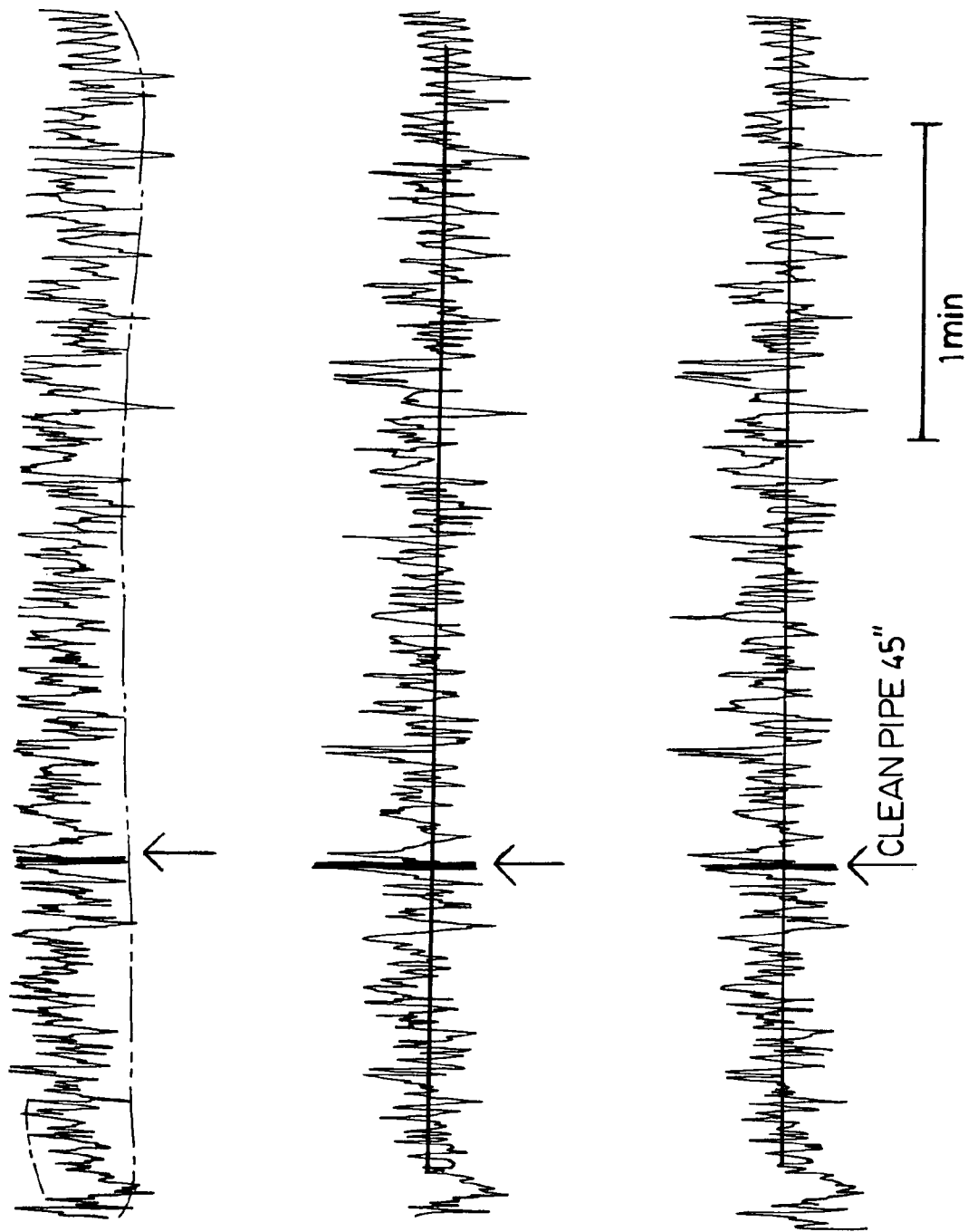
Figure 38:
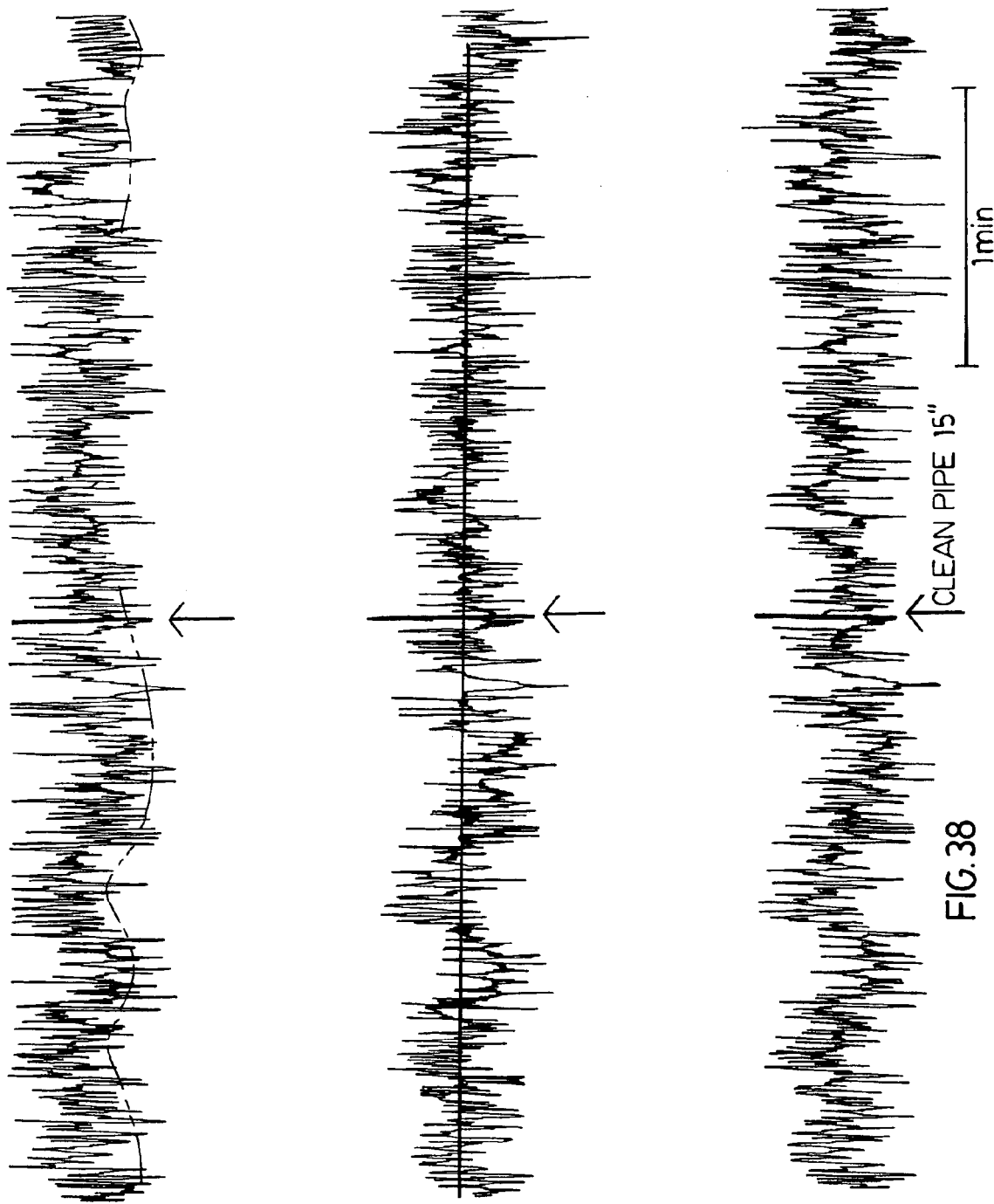
Figure 39:
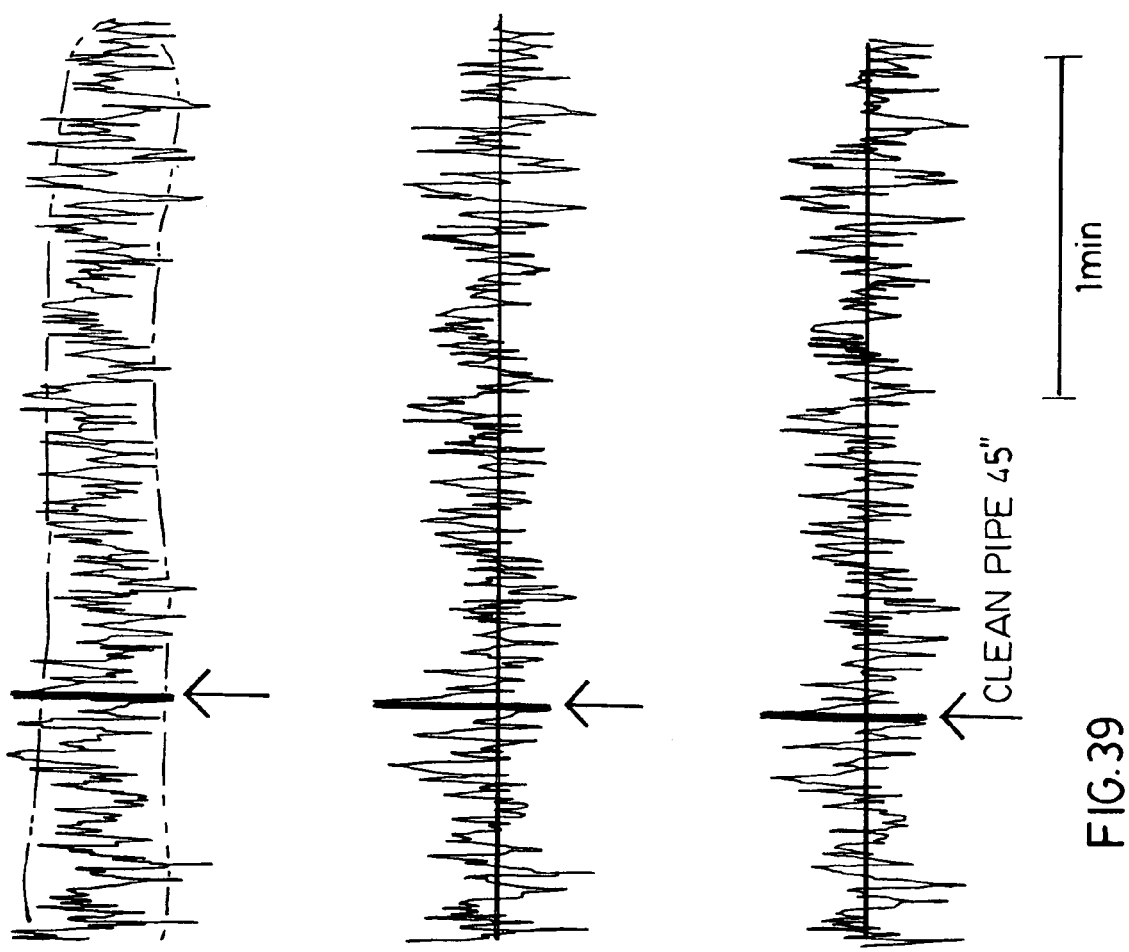
Figure 40:
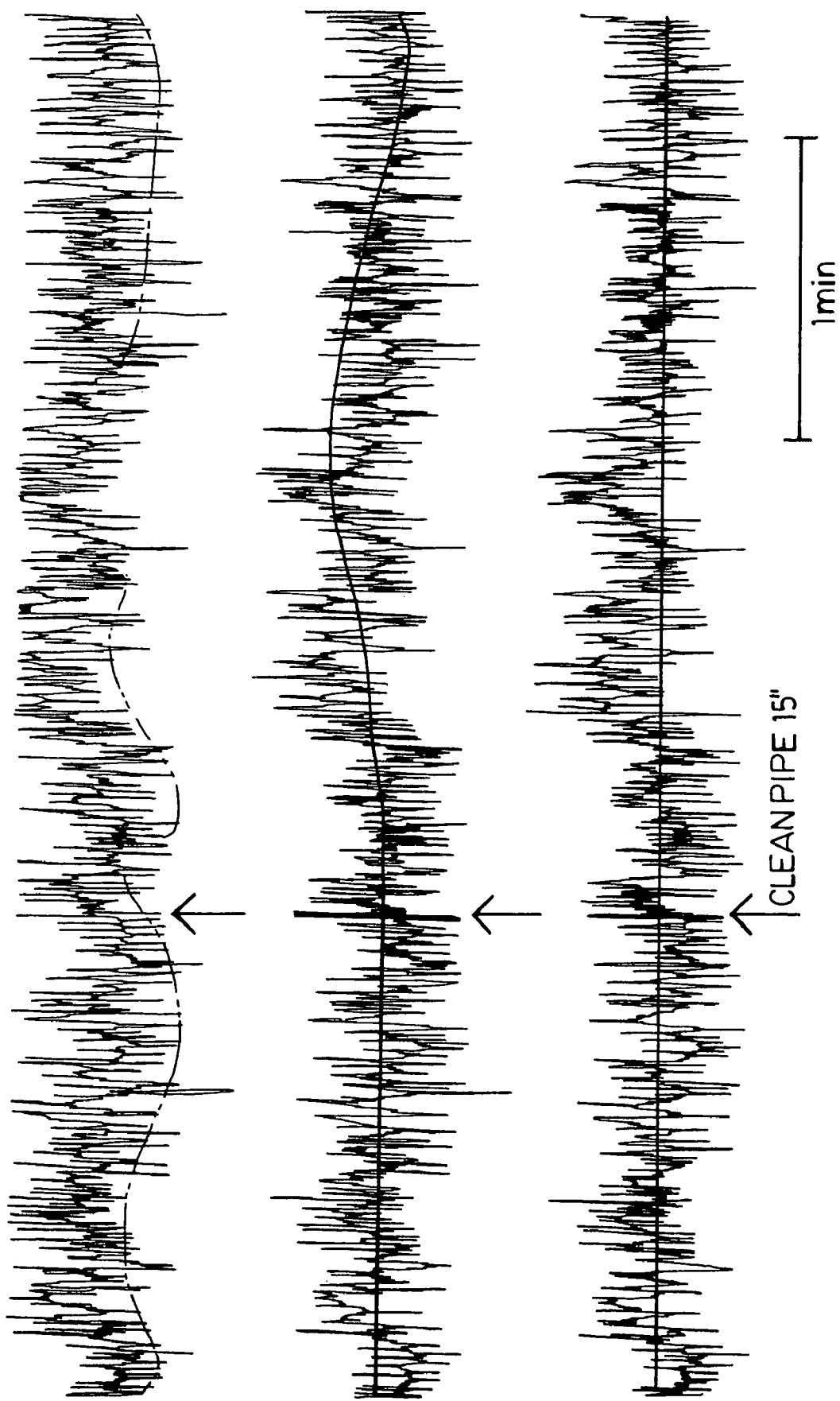
Figure 41:
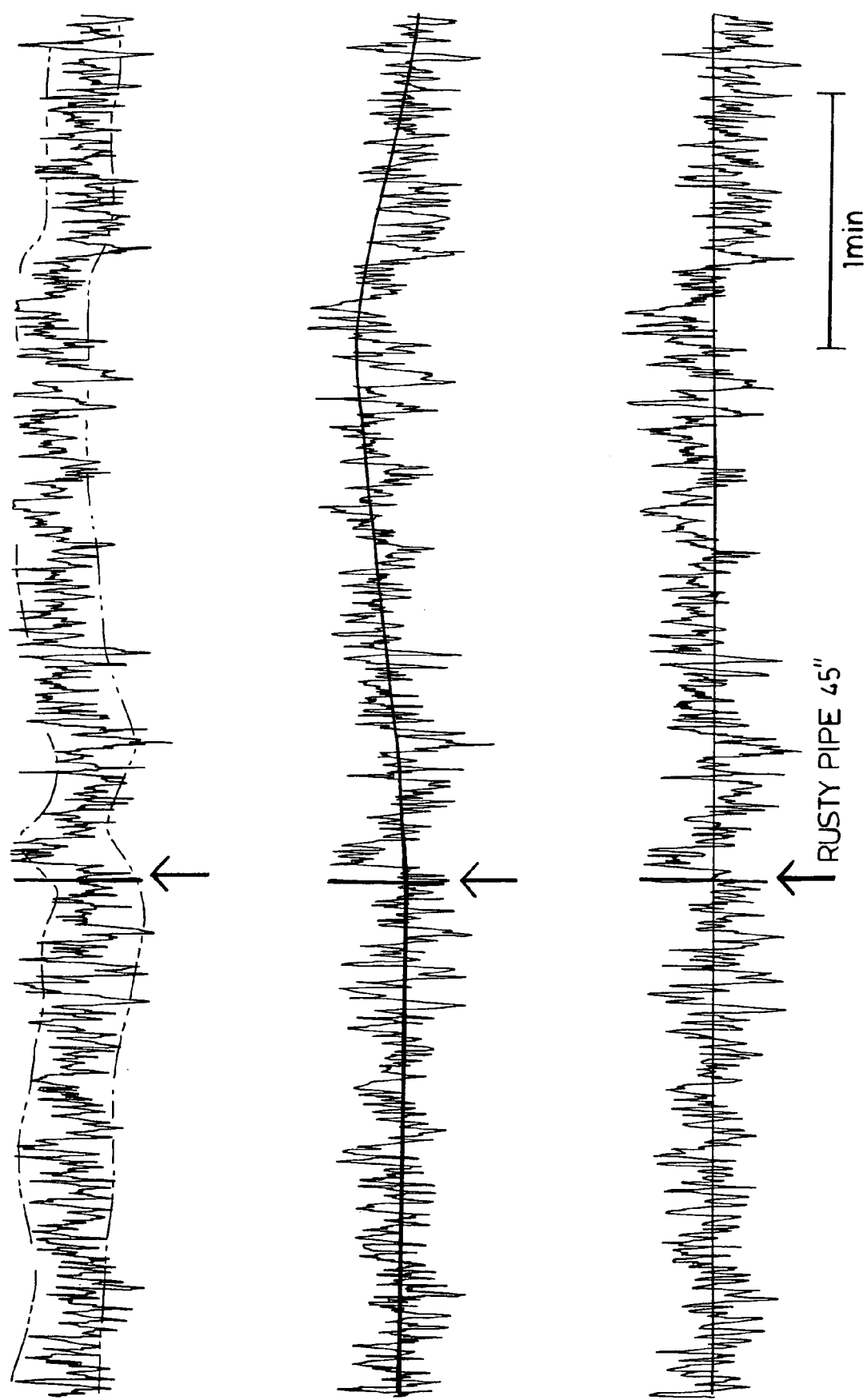
Figure 42:
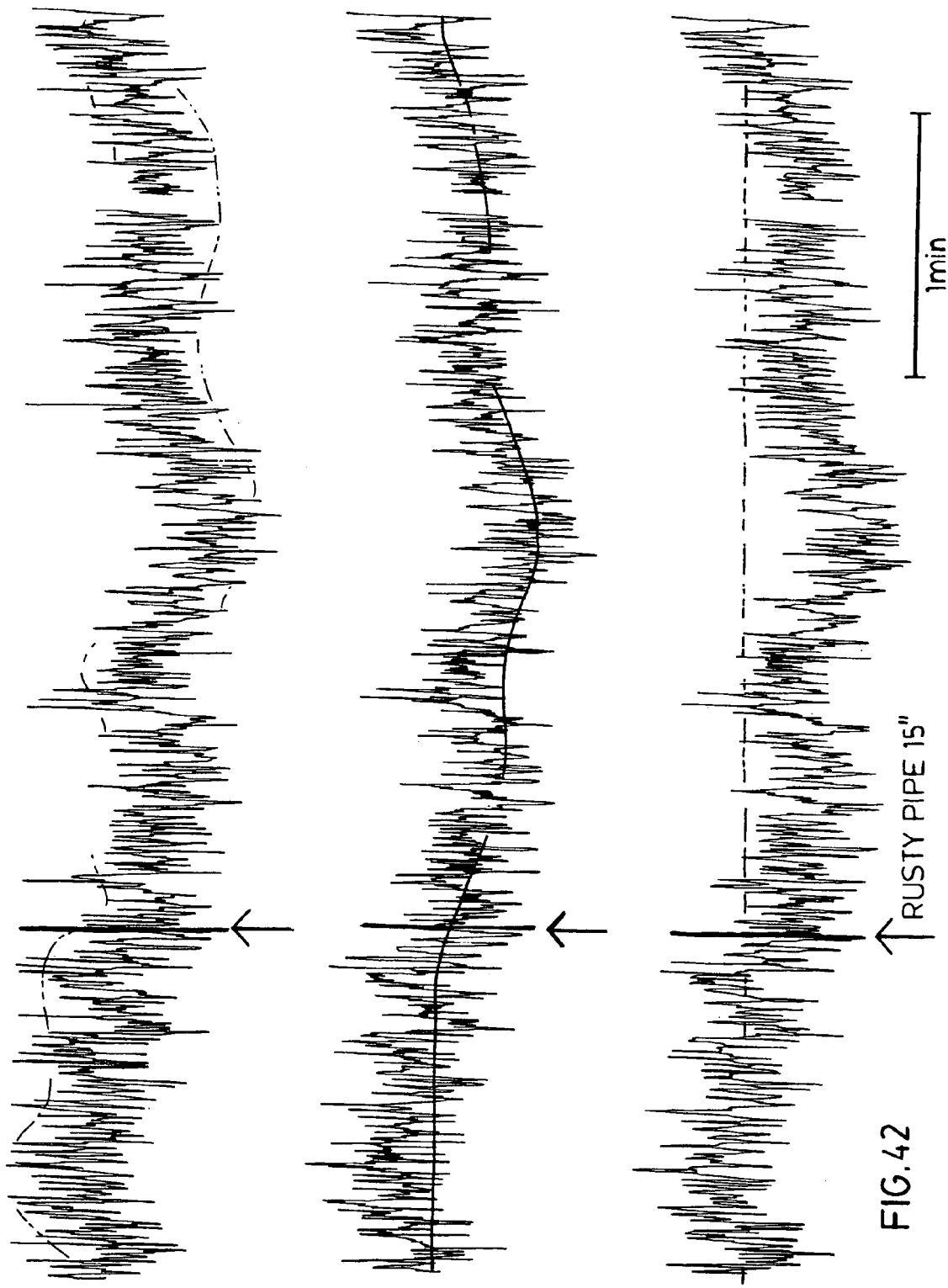
Figure 43:
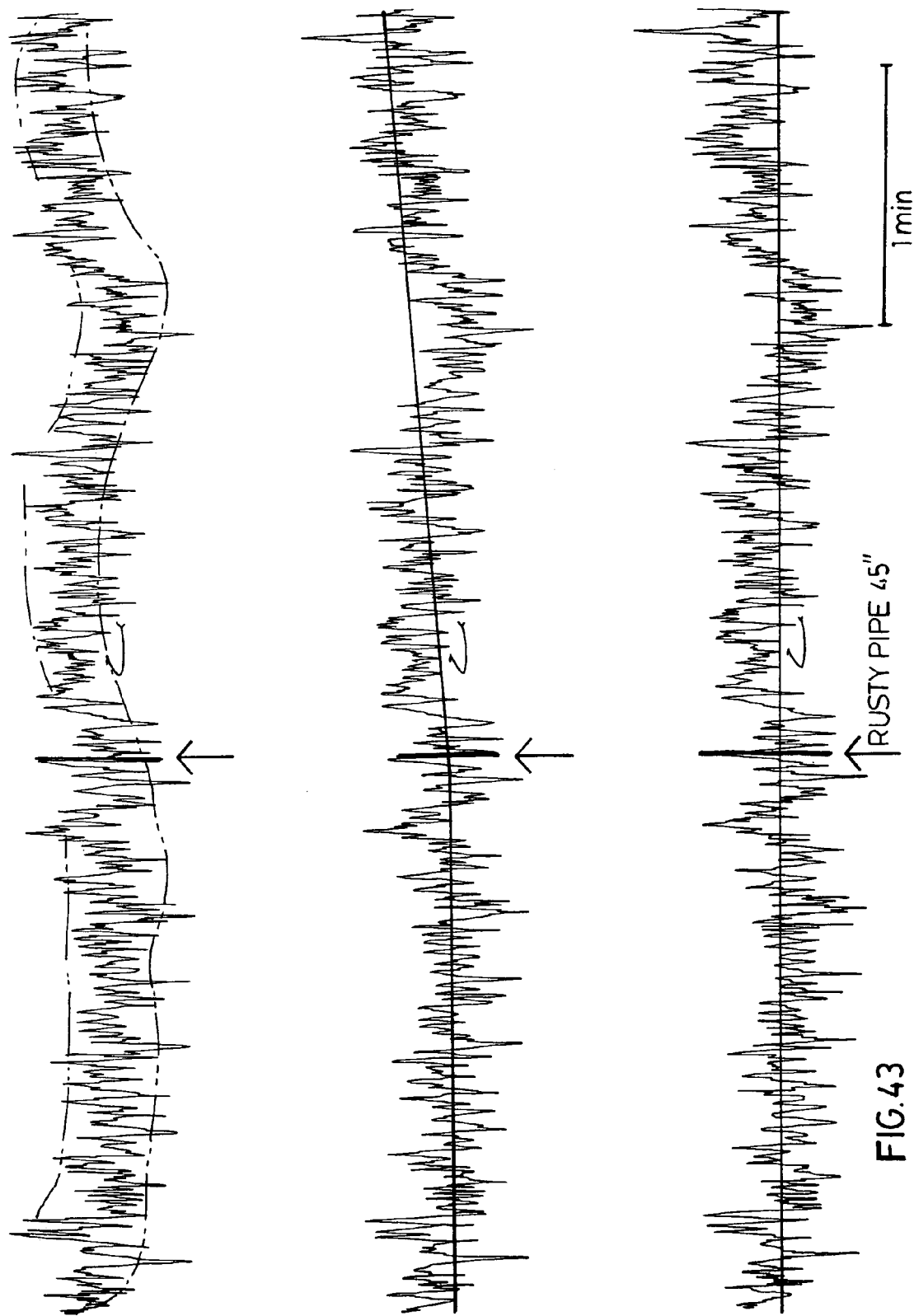

Another test system consists of a glass mason jar contained in a large plastic container filled with sand, facing the large aperture of the tapered horn. Test samples consist of a clean hollow steel pipe and another where the interior walls of the pipe are coated with rust. The two pipes are identical in size, about 10 cm long and 5 cm in diameter. The pipes are placed individually into the empty jar for a few seconds. The results obtained are recorded in FIGS. 37 to 43. FIG. 37 shows a minimal response to a clean (non-corroded) pipe, in that there appears to be more dense regions in the trace upon exposure to the pipe. There is little, if any, change in slope or digression from the baseline mean. FIGS. 38 and 39 show that the clean pipe elicits minimal changes in the trace. In FIG. 40, there is a modest transient slope from the baseline. In contrast, the corroded pipe (FIGS. 41 to 43) elicits a sustained change in the baseline, i.e. a gradually increasing slope.

Figure 44:
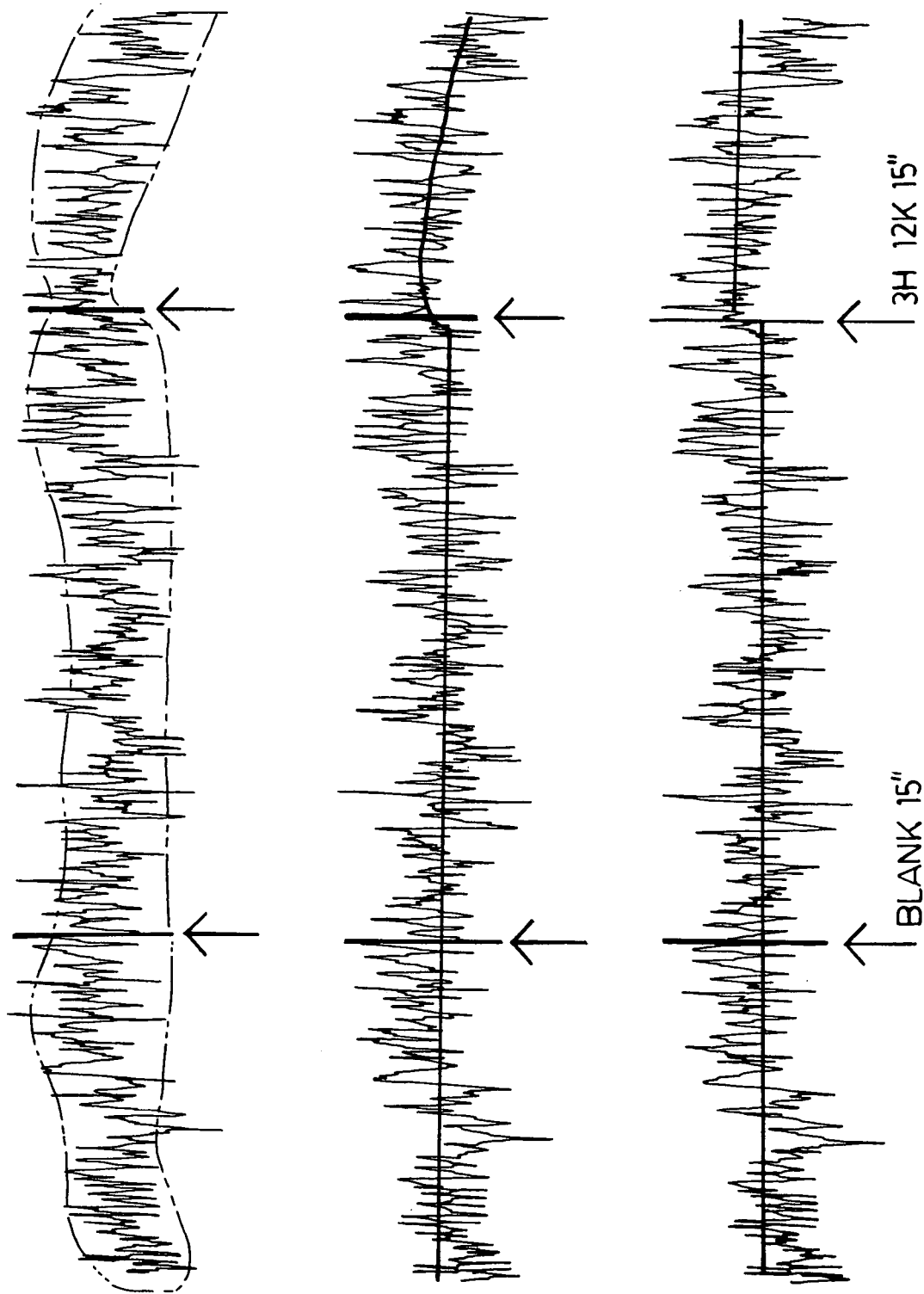

Tritium in a small plastic vial (the vial may be concealed in other types of containers) generates changes in sensor output signals, as do the other materials just described. $^3$H-progresterone, 12,000 dpm, elicits a sustained slope change in the ink trace, as seen in FIG. 44.

Figure 45:
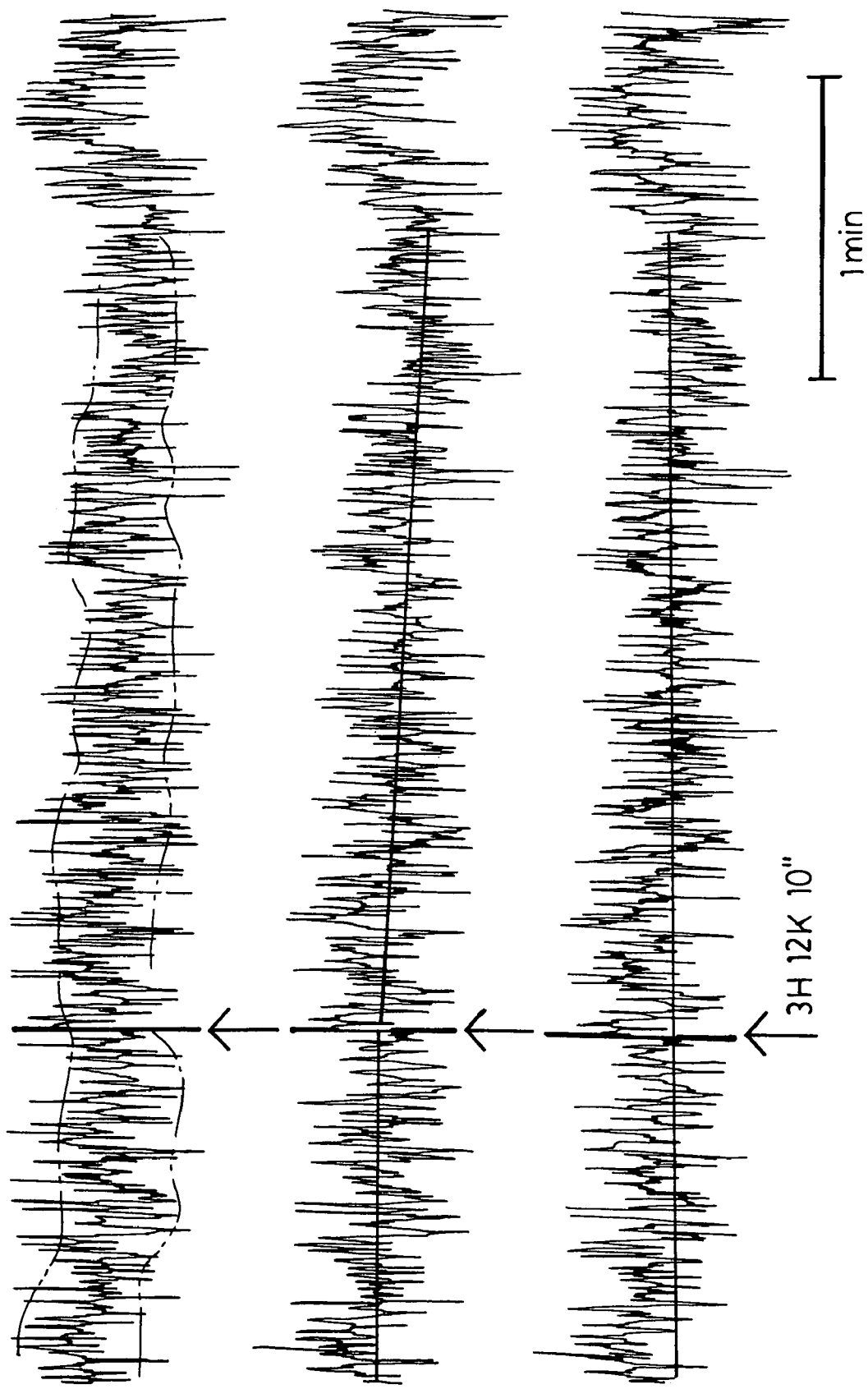
Figure 46:
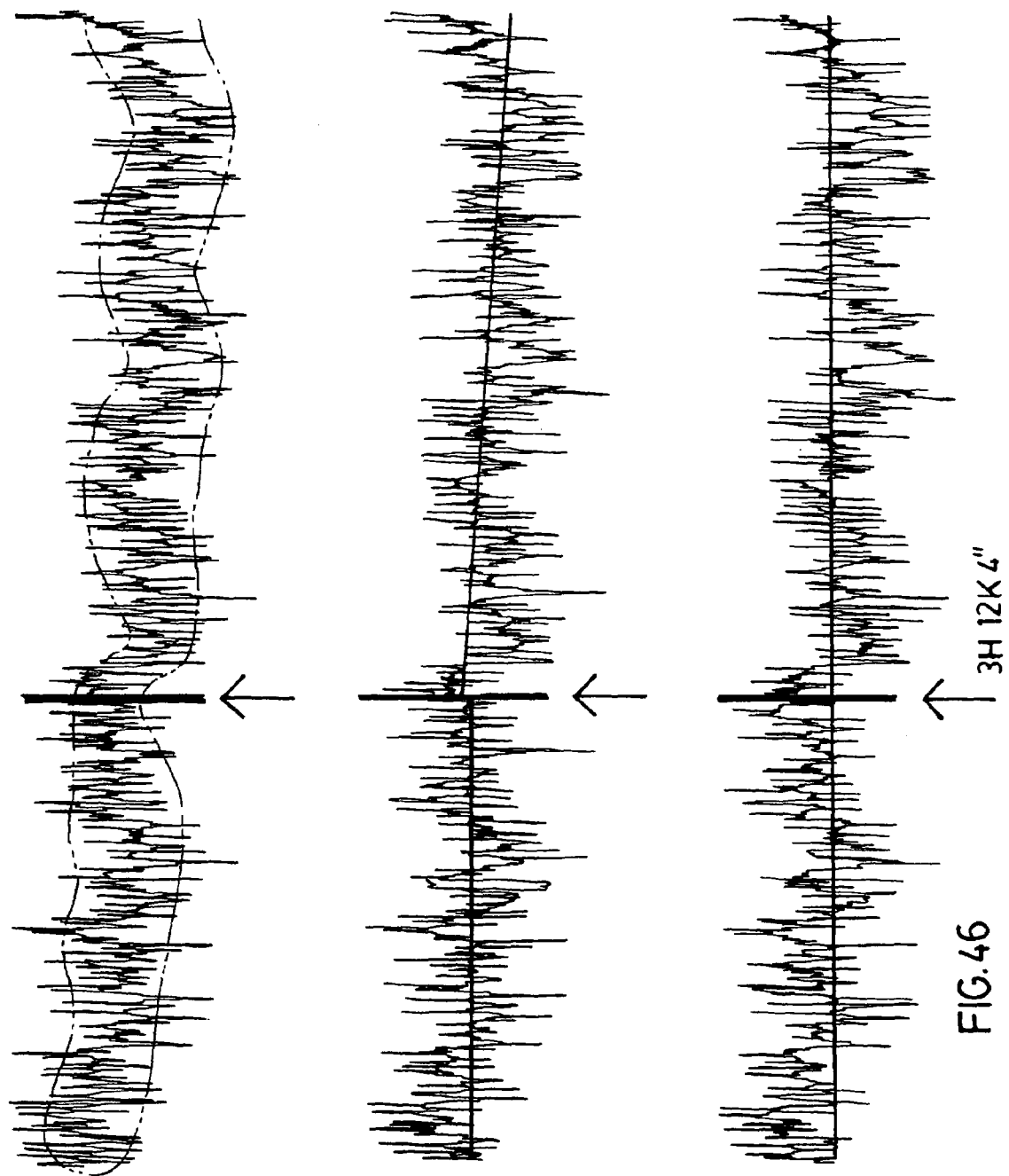
Figure 47:
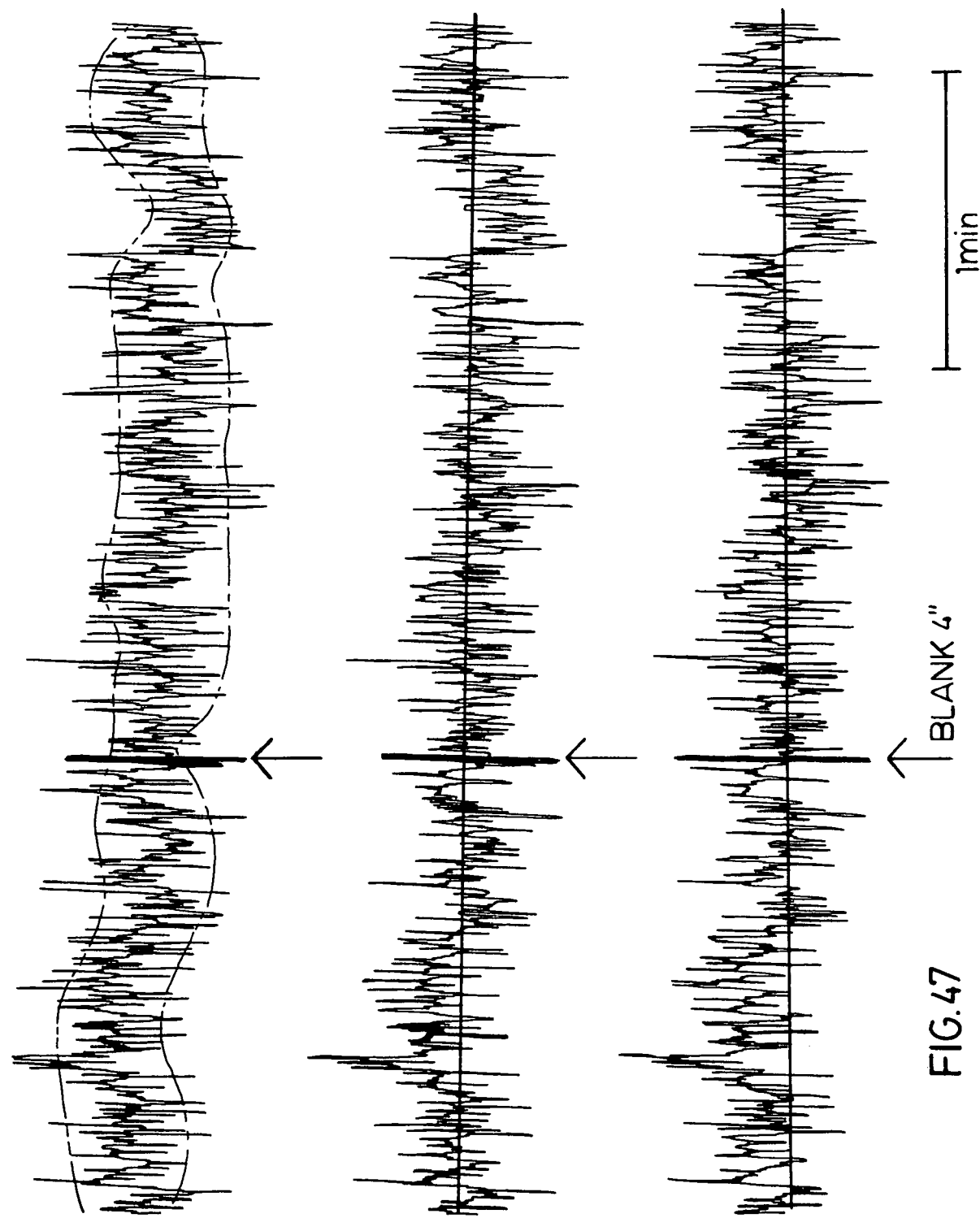

A series of runs with tritium, in succession, was done on a different instrument from that with which the previous record (FIG. 44) was obtained. FIG. 45 shows a typical "overwhelming" response, i.e. a symmetrical alternation of traces above and below the baseline mean voltage. This response resulted from the tritium (12,000 dpm) placed at the sensor for 10 seconds. The same tritium sample, placed for only 4 second (FIG. 46), generated a response characterized by a sustained trace below the baseline. A plastic vial control (with no tritium), placed for 4 seconds, did not elicit visually obvious changes in the trace (FIG. 47).

Figure 48:
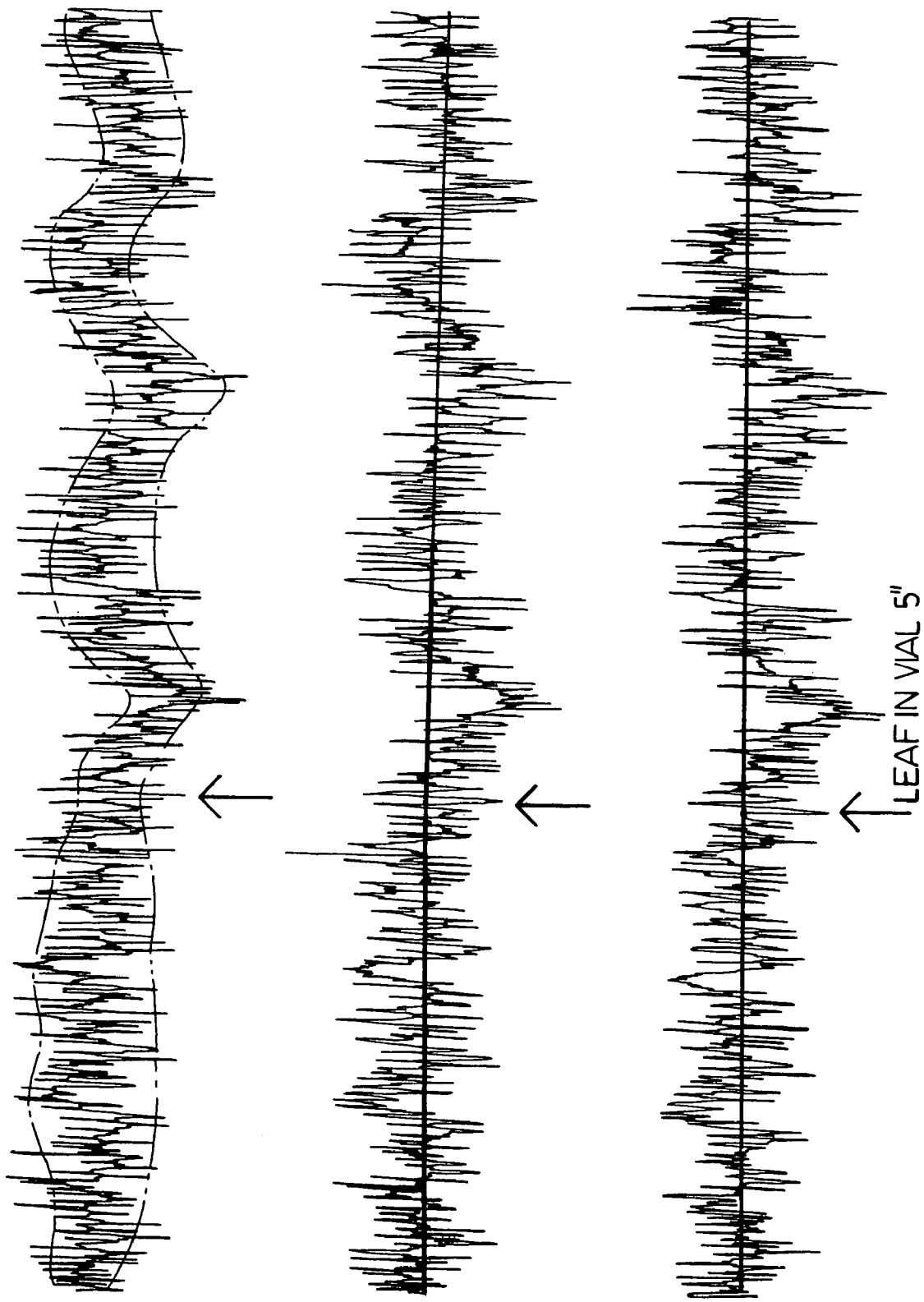
Figure 49:
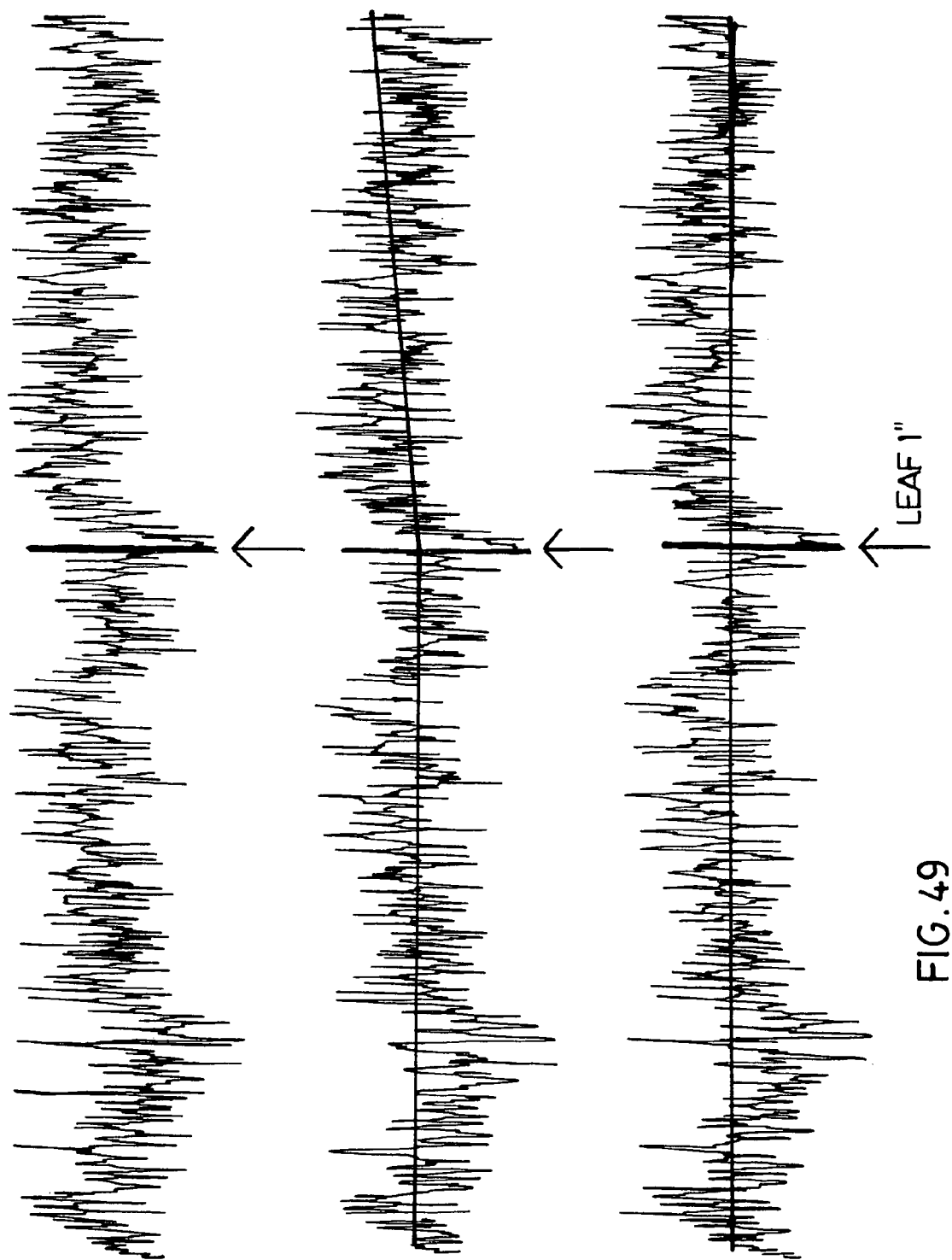

A piece of leaf (1×0.3 cm), cut from a potted African Violet plant, was placed on the inner surface of a clear glass vial, so that the entire surface of the leaf was exposed, through the glass wall, to the sensor. The vial was placed about 12 inches from the sensor for the number of seconds, as indicated on the chart record. Placement of the leaf vial for 5 second elicited a clear "overwhelming" response (FIG. 48), characterized by the undulating trace around the baseline mean. Note the increased number, as compared to baseline trace, of dense areas in the trace. A placement of the leaf for 1 second (FIG. 49) generated a sensor response represented by a sustained change in voltage above the baseline and a denser, more consolidated trace than that of the baseline.

SUMMARY OF THE DISCLOSURE

In summary of this disclosure, the present invention provides a novel method of detecting or analyzing an event or substance, such as a chemical reaction, molecular interaction and/or change of state of matter, by detecting a change in electromagnetic field strength. Modifications are possible within the scope of this invention.

REFERENCES (Be81) Benzii, R., Sutera, A. and Vulpiani, A. (1981). *J. Phys. A:* Math. Gen. 14:L453-L457.
(Co94) Cosic, I. (1994). IEEE Transactions on Biomedical Engineering 41(12):1101-1114.
(Co95) Collins, J. J., Chow, C. C. and Imhoff, T. T. (1995). *Nature* 376:236-238.
(Do8O) Doull, J. et al. (1980). Casarett and Doull's Toxicology. Macmillan, New York.
(FO86) "FOCUS" Article (1986), *Analyt. Chem.* 58(14): 1428A-428B.
(Ha49) Harnwell, G. P. (1949). Principles of Electricity and Electromagnetism. McGraw-Hill, New York.
(No51) Noller, C. R. (1951). Chemistry of Organic Compounds. W. B. Saunders, Philadelphia.
(Si82) Sinal, Ya G. (1982). Theory of Phase Transitions: Rigorous Results, Pergamon Press, Oxford.
(Vi77) Villain, J. (1977). *J. Phys.* C10:4793-4803.
(Wi76) The Merck Index, 9th Edn. (1976). Windholtz, M. et al. (eds.). Merck & Co. Inc. (publ.), Rahway, N.J.

TABLE 1

Some Applications of Signature Spectra and Pattern Analysis

A. Enzyme reactions
   1. Sequential addition of substrate,
   2. Mixtures of substrates
   3. Optimization of conditions: co-factors, ions, metals
   4. Spectra from cells and tissues
B. Molecular interactions
   1. Ligand/receptor
   2. Antigen/antibody
   3. Substrate/enzyme
C. Tissue/cell profiles
   1. Basal conditions or in response to added ligand
   2. Normal vs. diseased
   3. Specific frequency spectrum signature

TABLE 2

Examples of some biochemical pathways that the inventors have identified by use of the device described in this document

| | Metabolized by | |
|---|---|---|
| Substrates | rat liver Microsomes | *pig liver chromatin |
| Non-NADPH-dependent | | |
| histidine | + | ++ |
| histidinol | + | + |
| histamine | + | + |
| adenosine | + | + |
| ornithine | ++ | + |
| NADPH-dependent | | |
| aminopyrine | + | − |
| aniline | + | − |
| putrescine | + | + |
| testosterone | − | + |
| estridiol | − | − |
| progresterone | + | − |
| cortisol | + | − |
| amitryptyline | + | + |
| fluoxetine | + | + |

Legend:
"+" = Pathway response readily apparent.
"++" = Strong pathway response.
"−" = No response; no evidence for pathway.
*Most of these observations and virtually all in the chromatin are original to our laboratories and can be done with our device, in its present state of development, in a total of no more than 10 experimenter-hours. Currently available state-of-the-art analytical systems would likely require a minimum of 2500 experimenter-hours to accomplish the same results.

TABLE 3

Abbreviations on Figures
(Numbers in parentheses indicate vol in μl concentrations of stock solutions added)

| | |
|---|---|
| AD = | adenosine (0.2 mM) |
| AN = | aniline (0.2 mM) |
| AP = | aminopyrine (0.2 mM) |
| B = | 0.1 M TRIS-$PO_4$ buffer |
| CHROM = | chromatin from pig liver nuclei (1 mg protein/ml) |
| CORT = | cortisol (1 μM) |
| EST = | β-estradiol (1 μM) |
| GBT = | glass bottom tube |
| HA = | histamine (0.2 mM) |
| HD = | histidine (0.2 mM) |
| HOL = | histidinol (0.2 mM) |
| NADPH = | reduced nicotinamide adenine dinucleotide phosphate (0.5 mM) |
| ORN = | ornithine (0.2 mM) |
| PBT = | probe blade is bottom of tube |
| PGT = | flat-bottom glass tube on probe |
| PL = | phospholipid substrate |
| PLase = | bee venom phospholipase |
| PLN = | pig liver nuclei (1 mg protein/ml) |
| PROG = | progesterone (1 μM) |
| PU = | putrescine (0.2 mM) |
| Regen = | NADPH regeneration system: glucose-6-phosphate, glucose-6-phosphate dehydrogenase, NADP |
| RLM = | rat liver microsomes (1 mg protein/ml) |
| TEST = | testosterone (1 μM) |

TABLE 4

Legends to FIGS. 2 to 23

Figure 2:
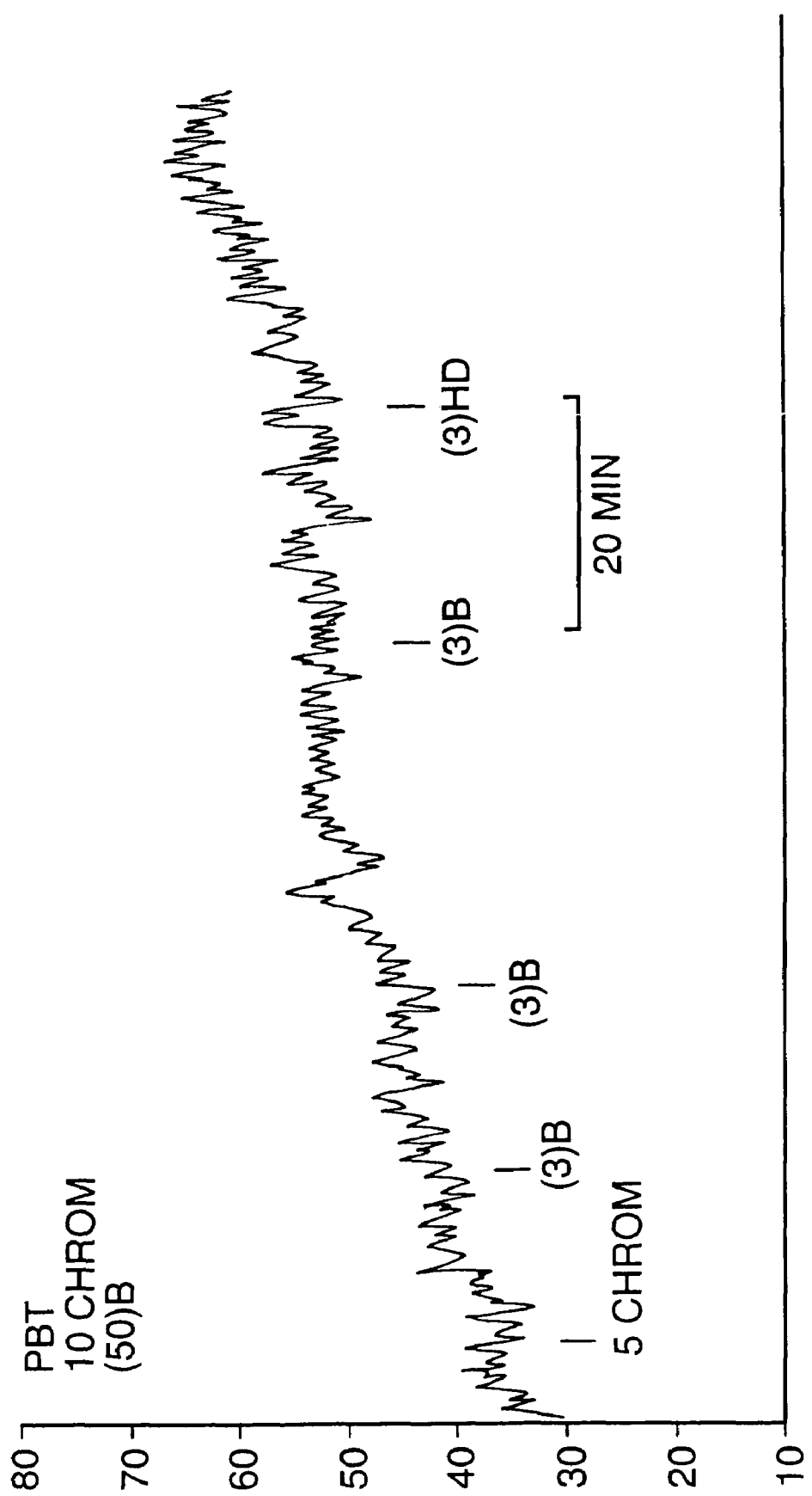
FIGS. 2 to 23 are a series of actual charts generated using the apparatus of FIGS. 1a and 1b, illustrating some typical reactions examined, showing the experimental conditions employed and the results obtained.
Figure 3:
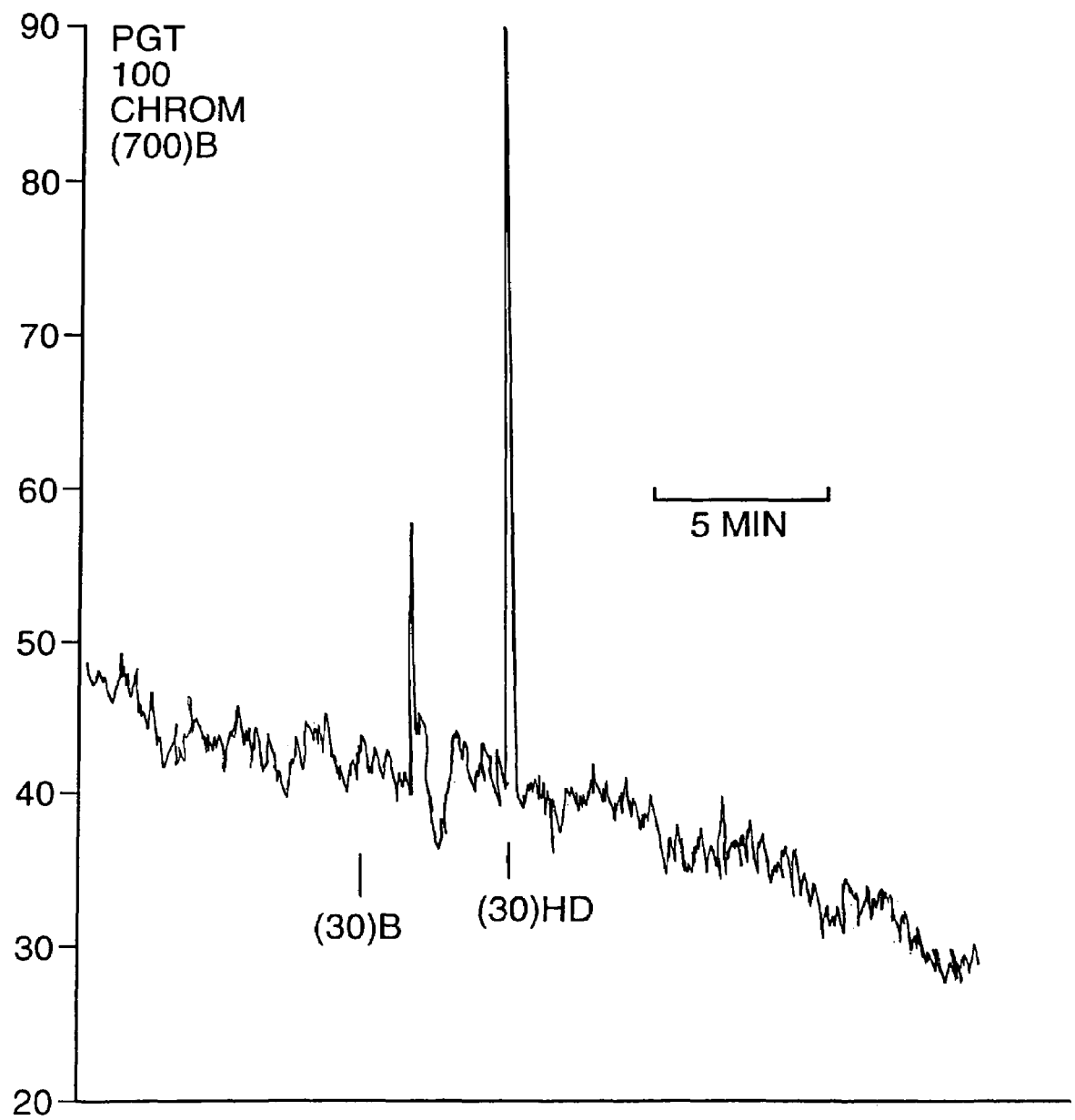
Figure 4:
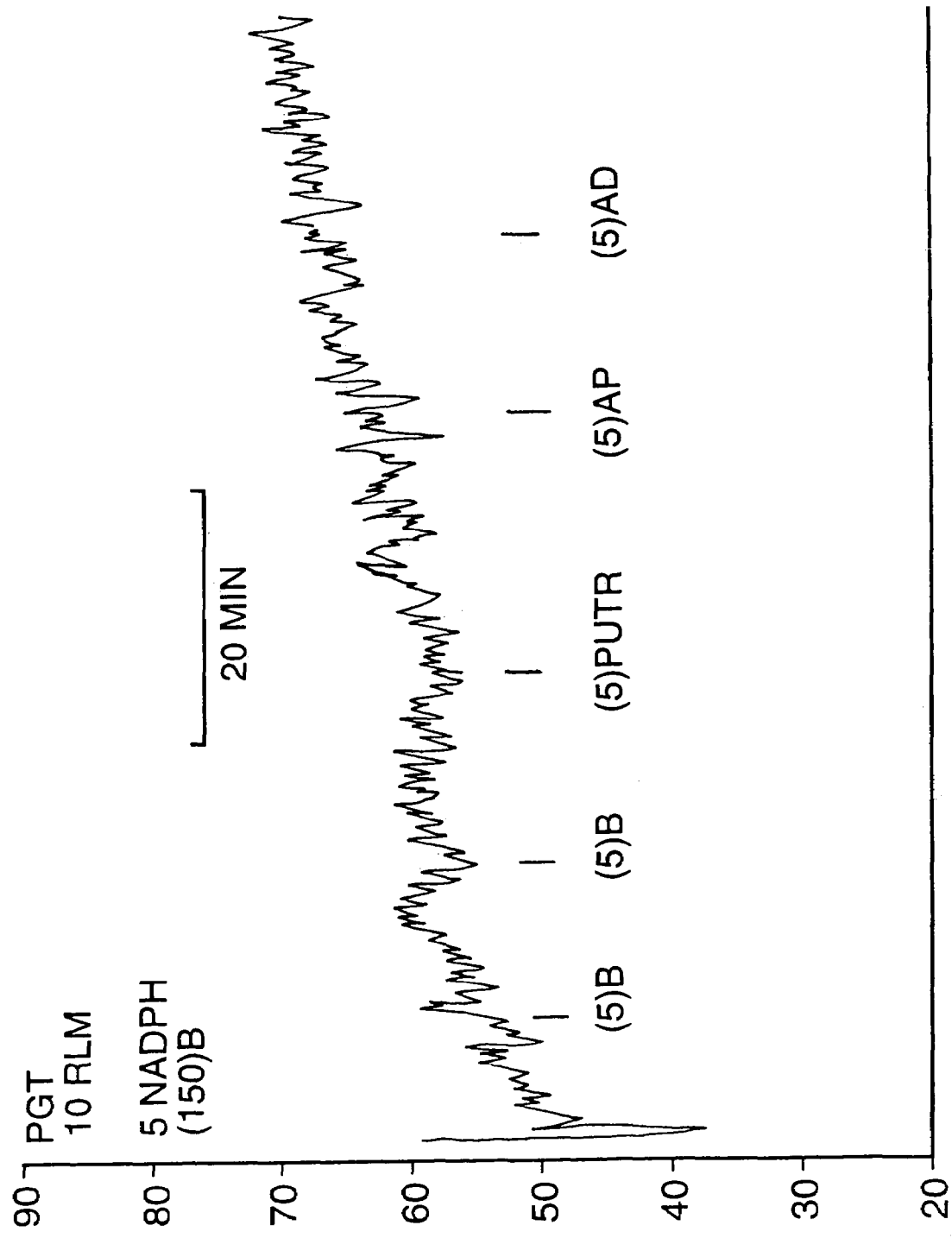
Figure 5:
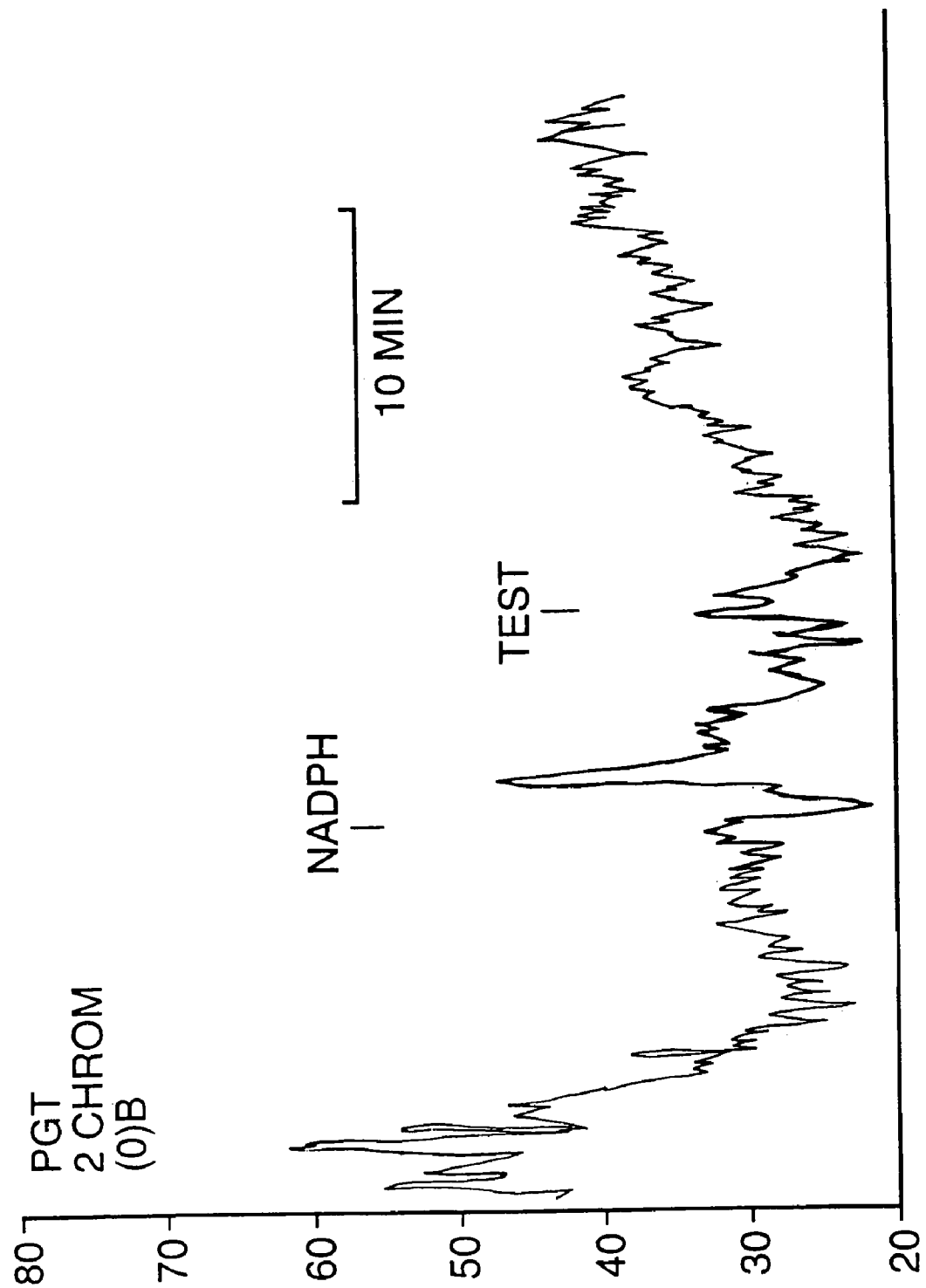
Figure 6:
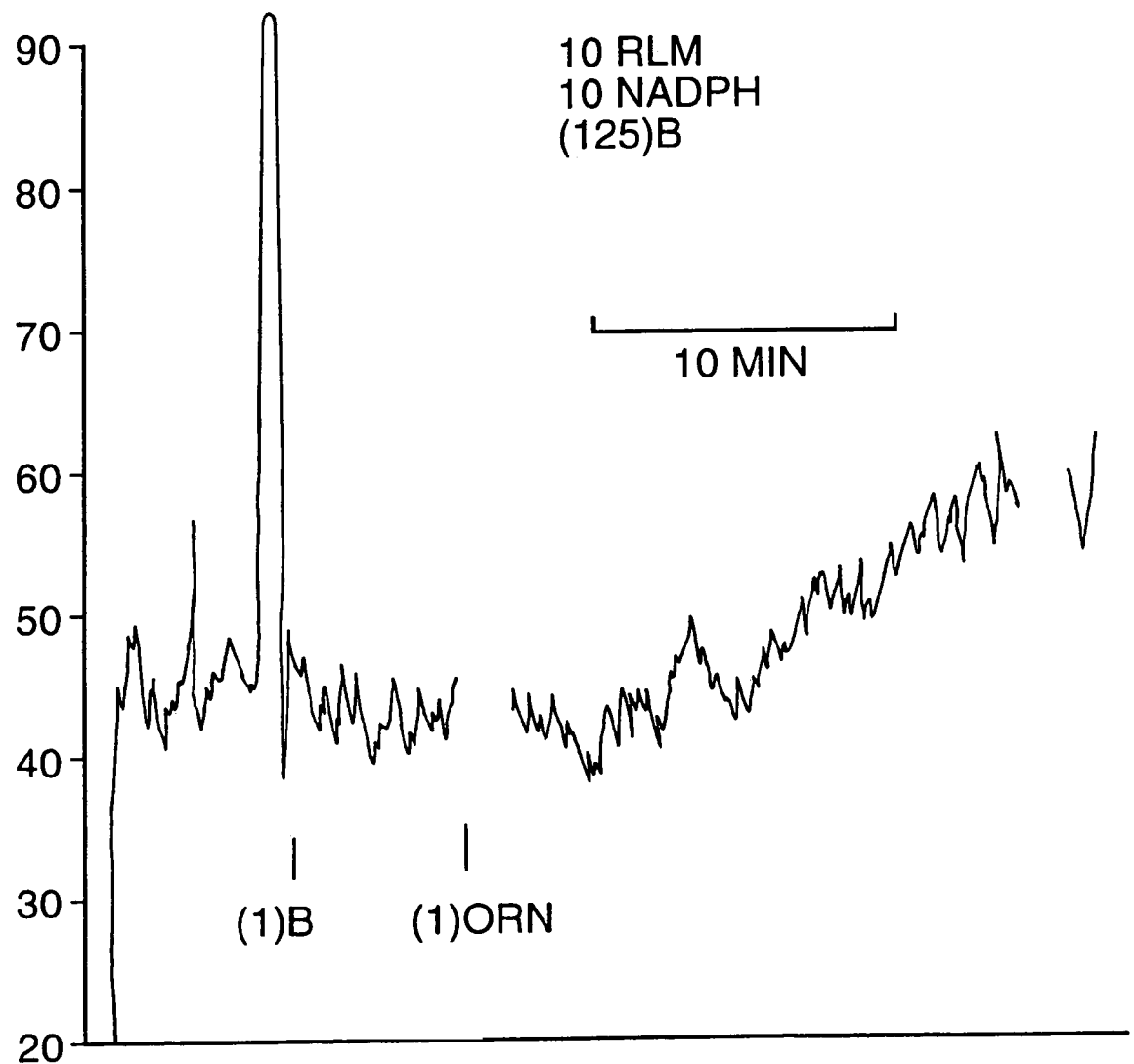
Figure 7:
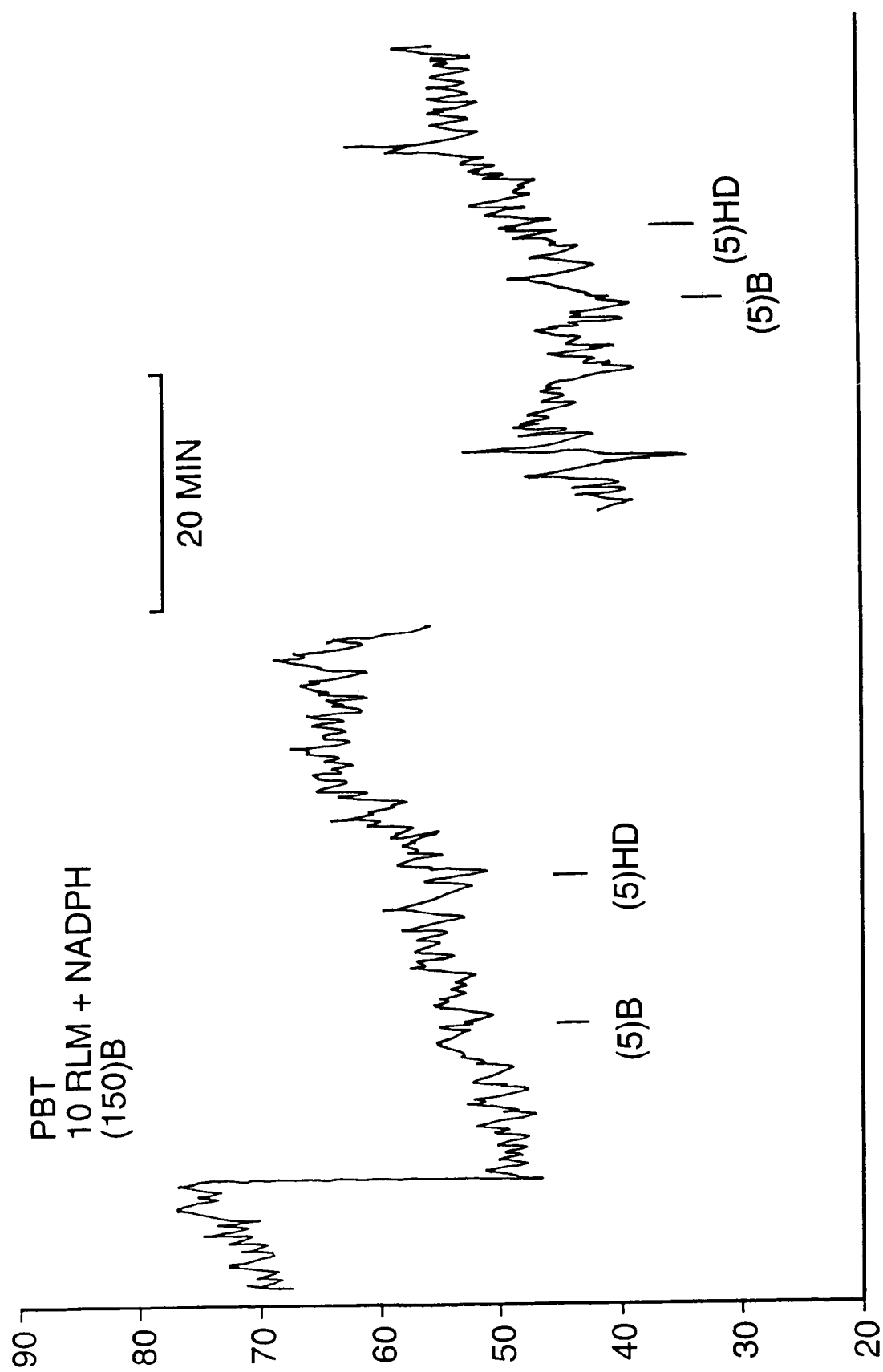
Figure 8:
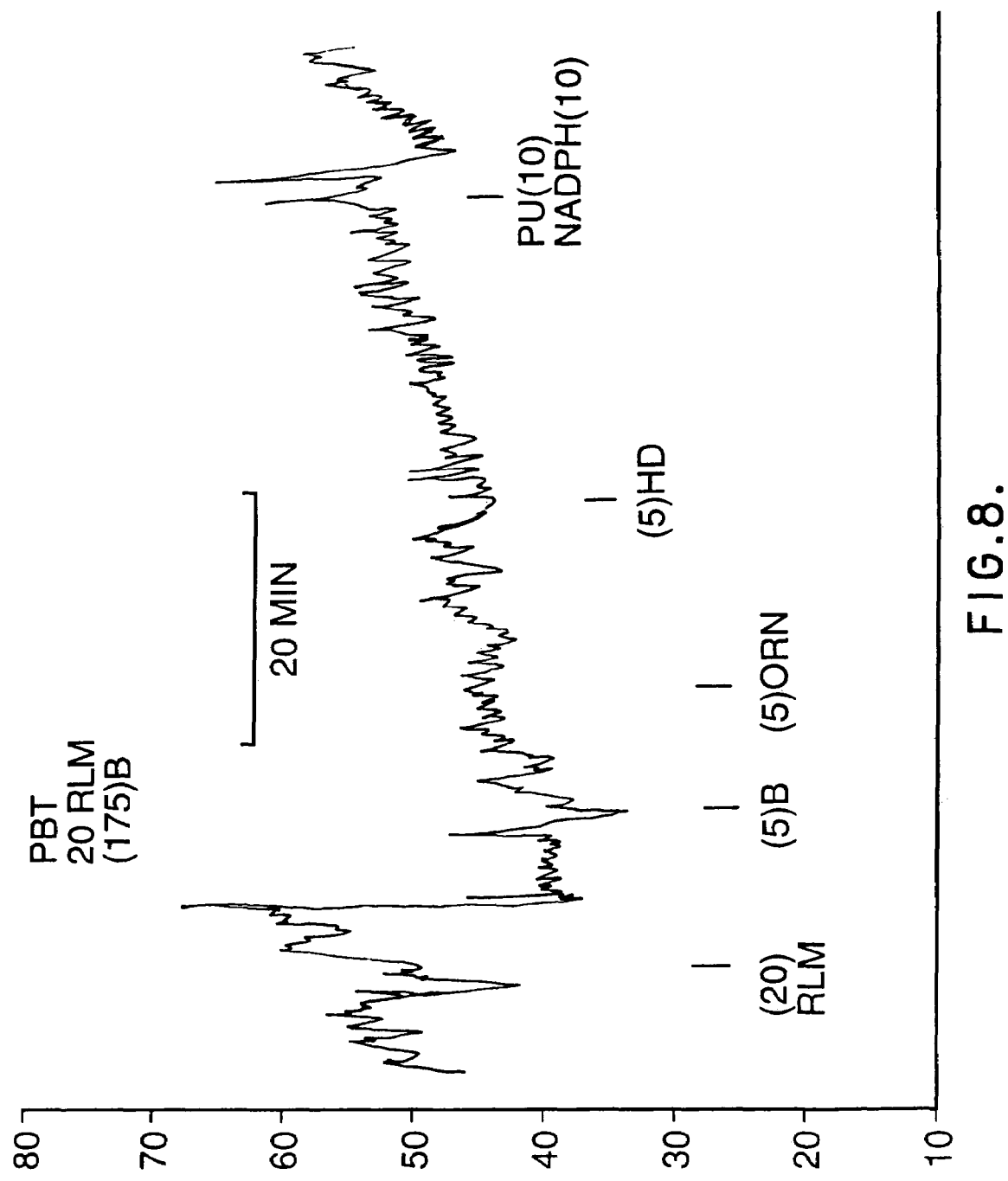
Figure 9:
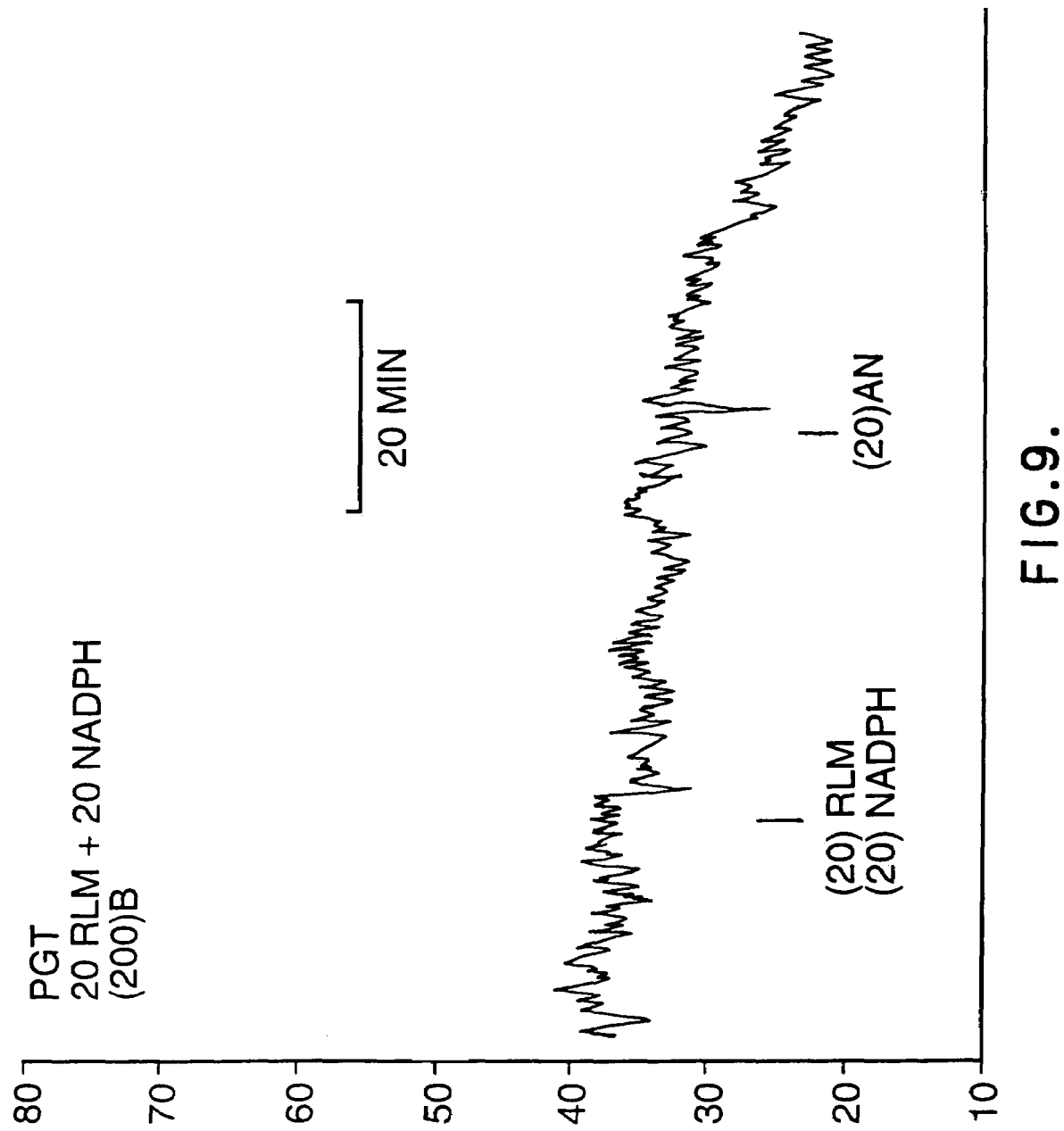
Figure 10:
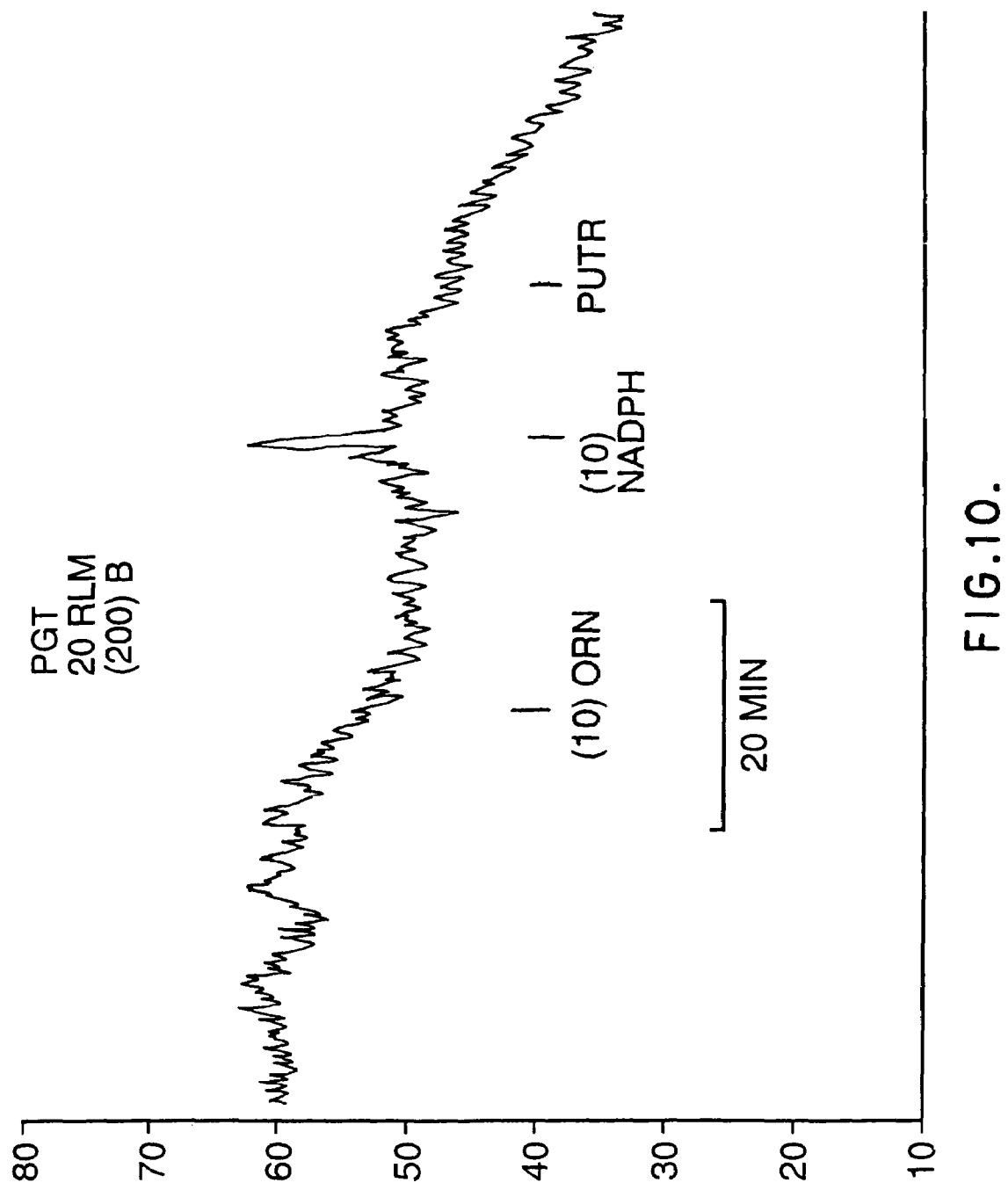
Figure 11:
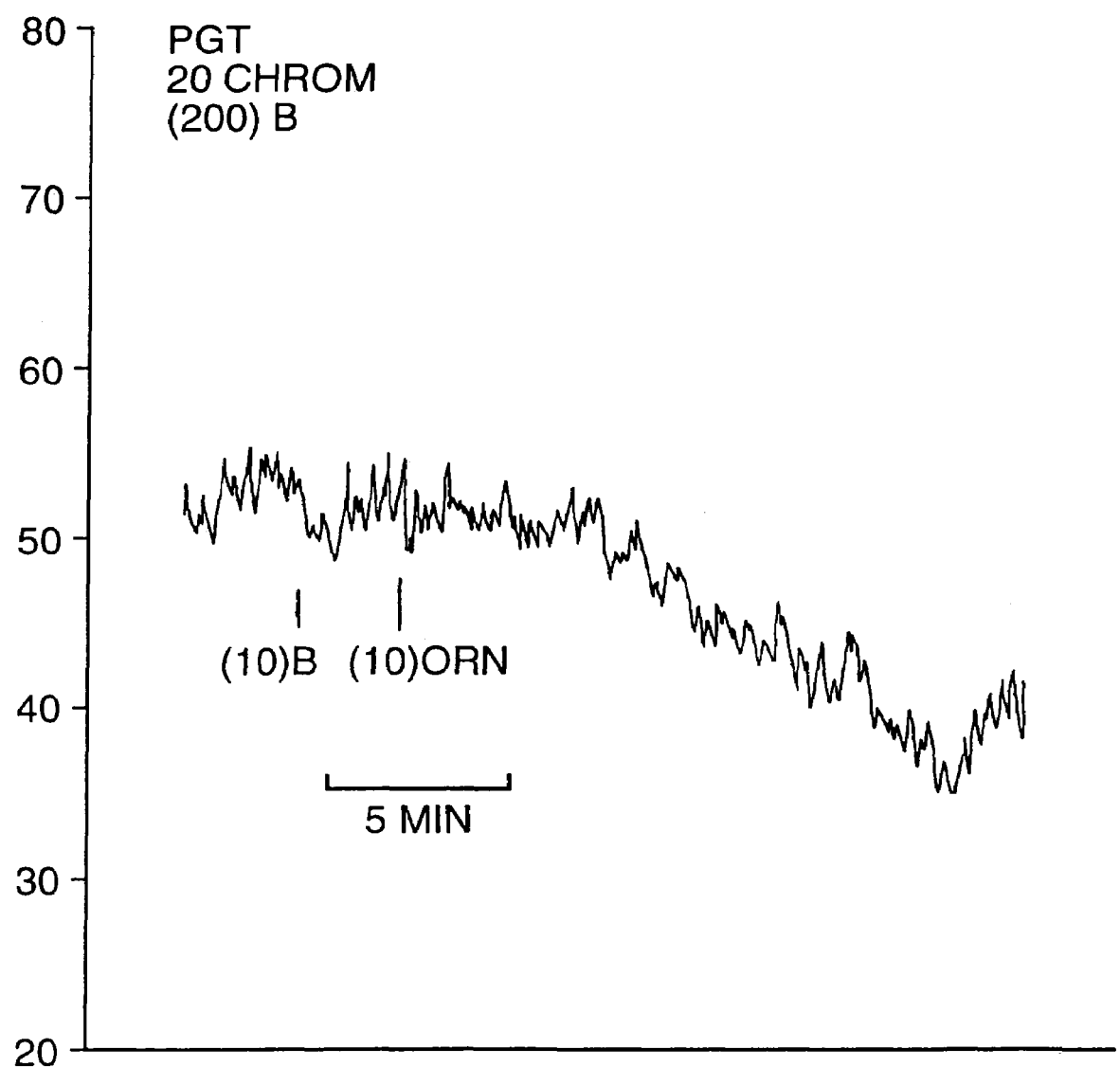
Figure 12:
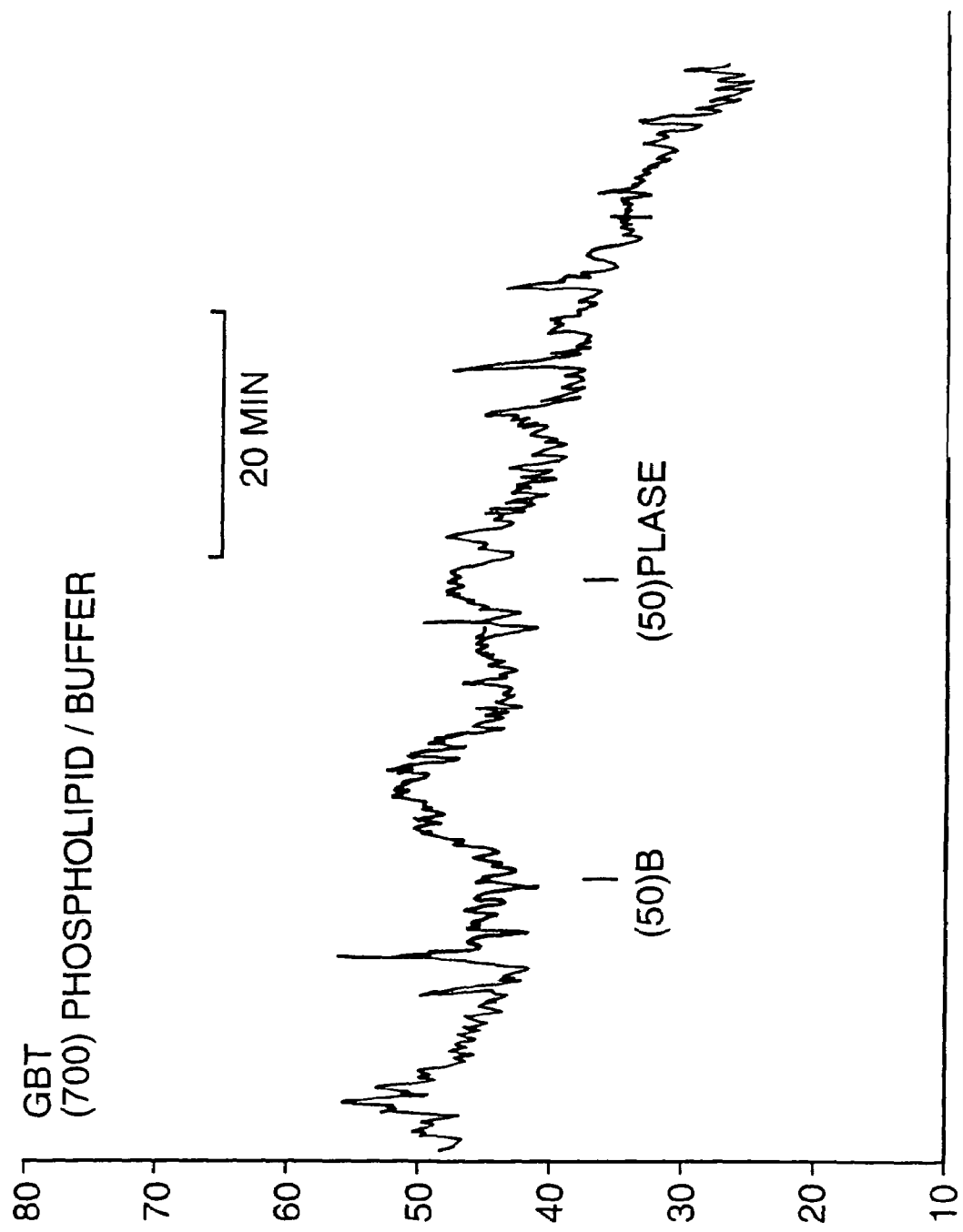
Figure 13:
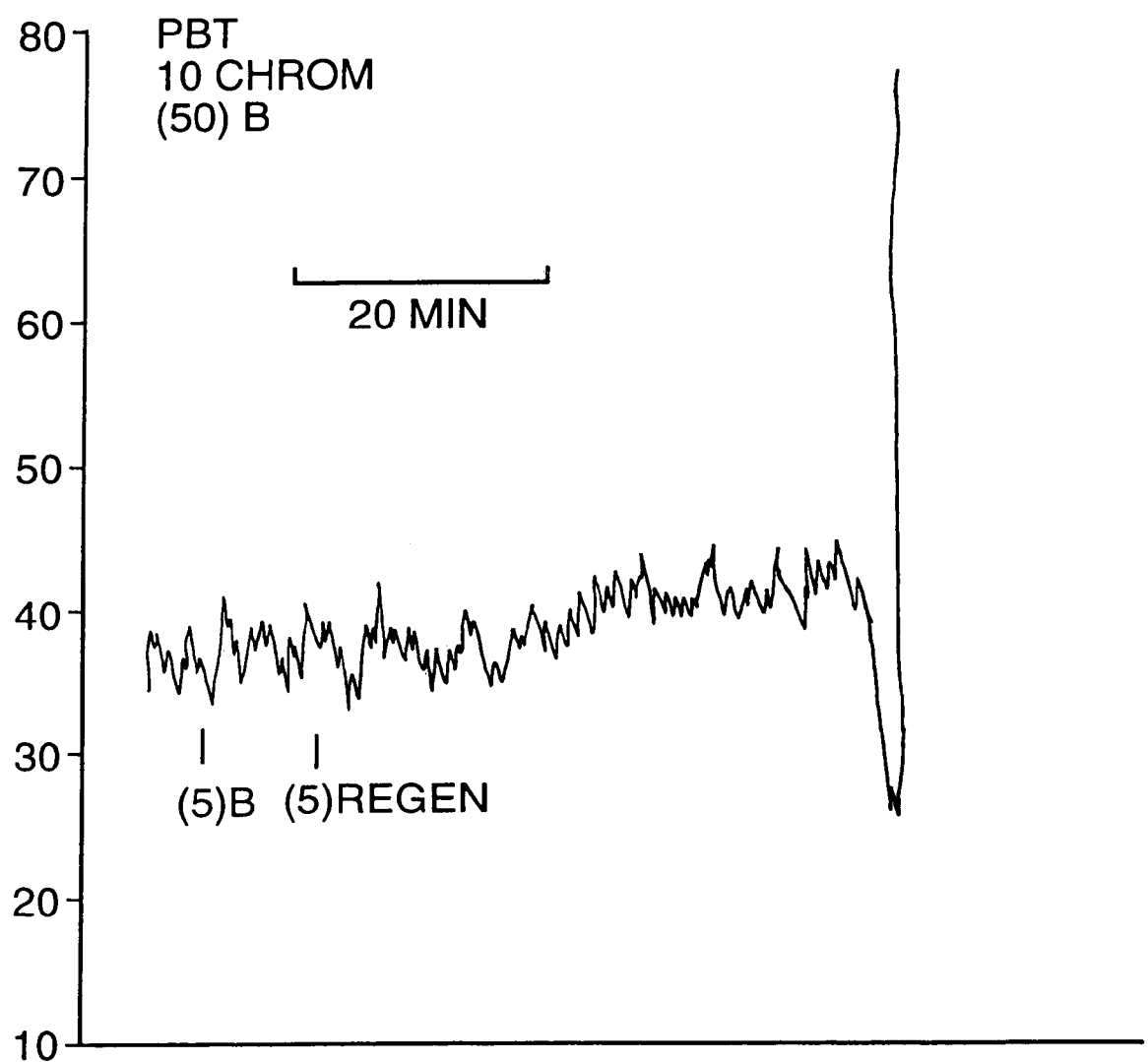
Figure 14:
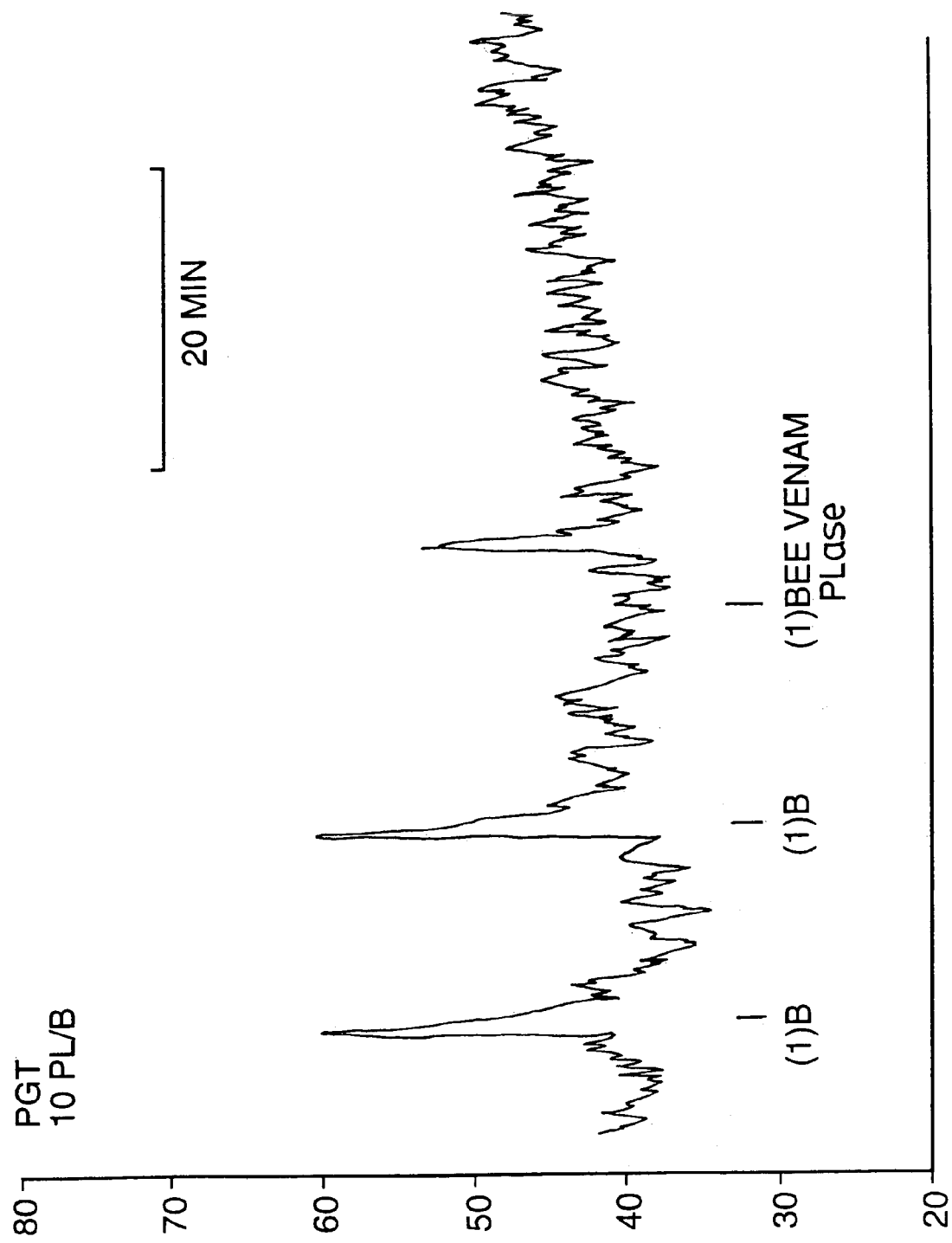
Figure 15:
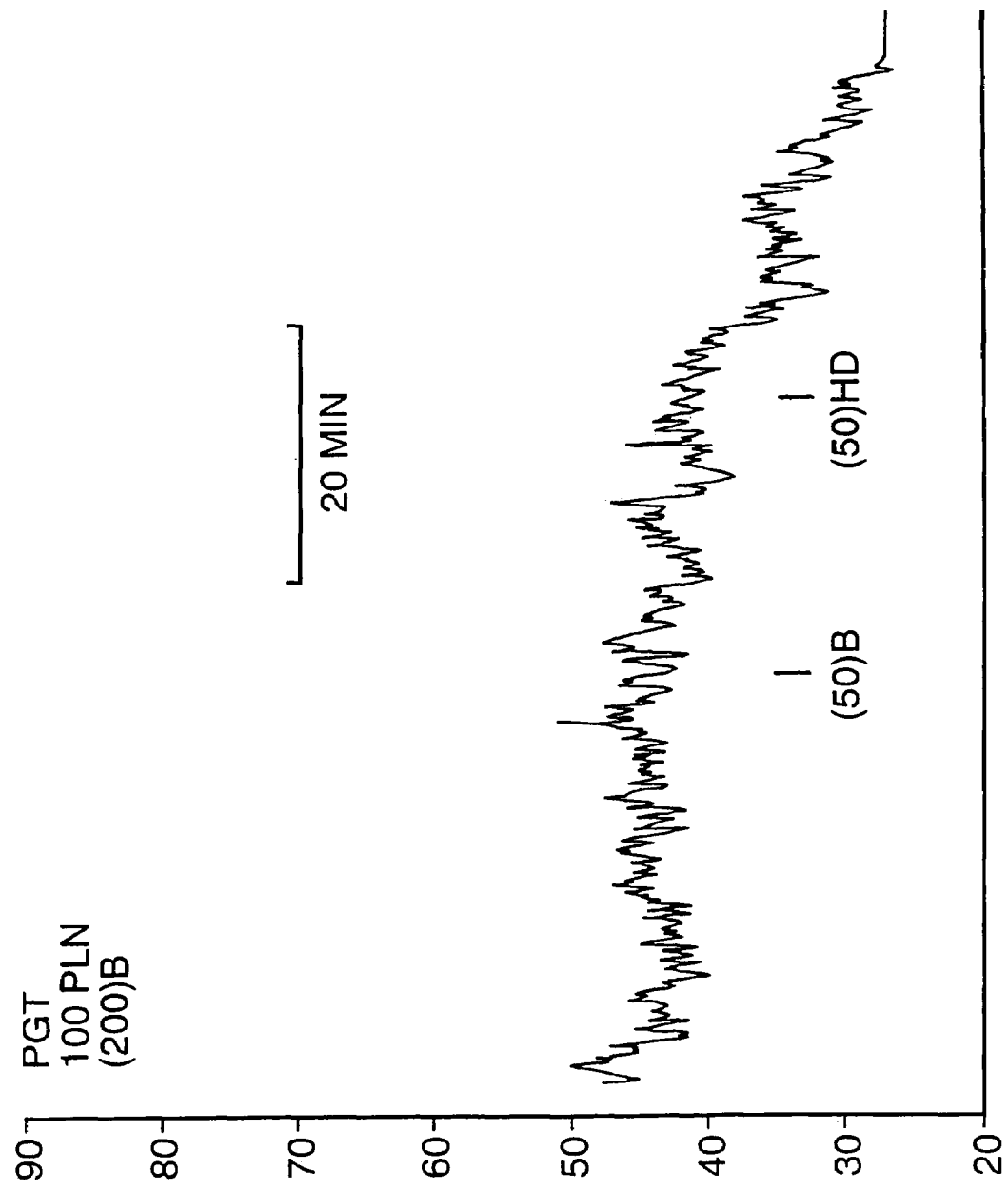
Figure 16:
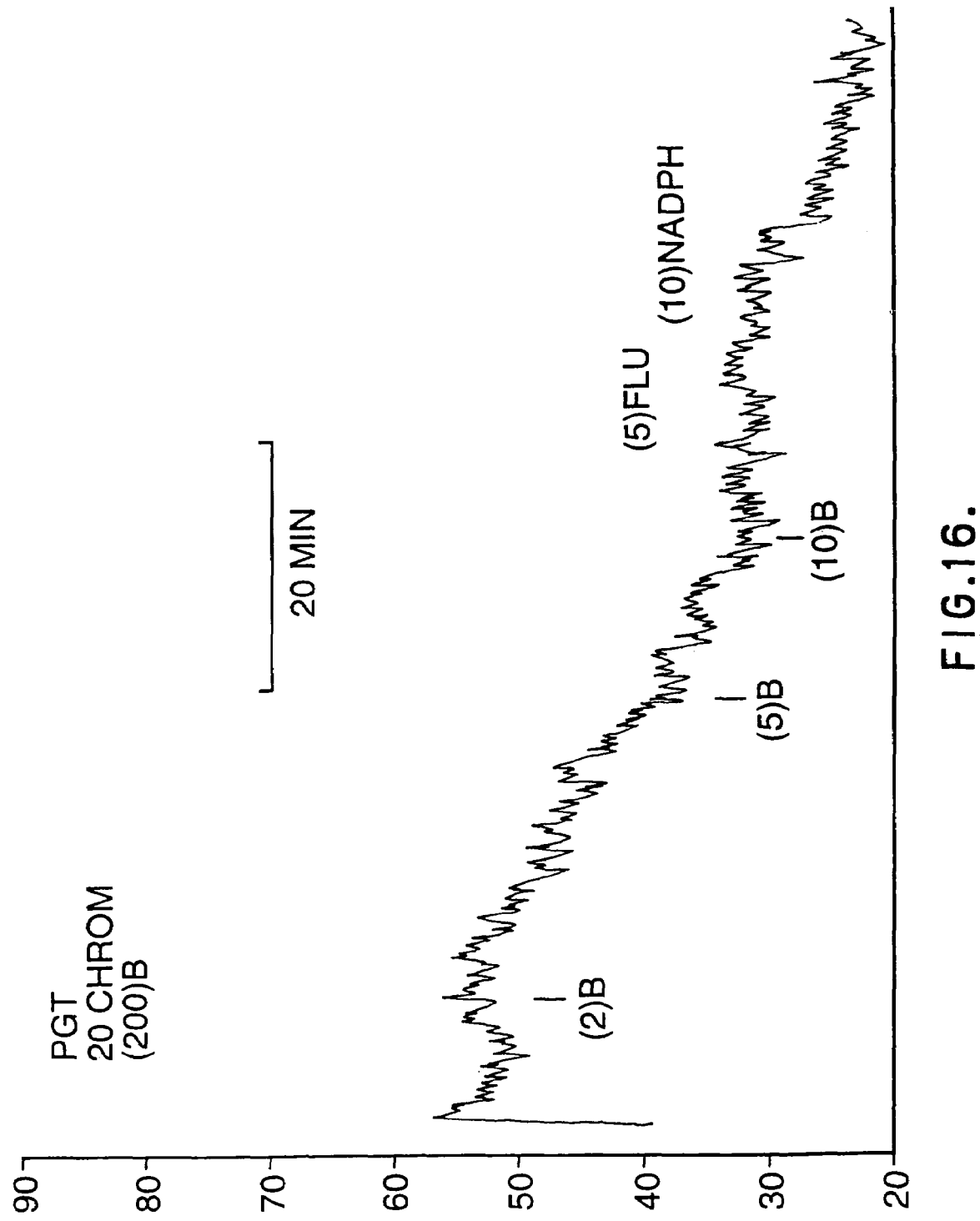
Figure 17:
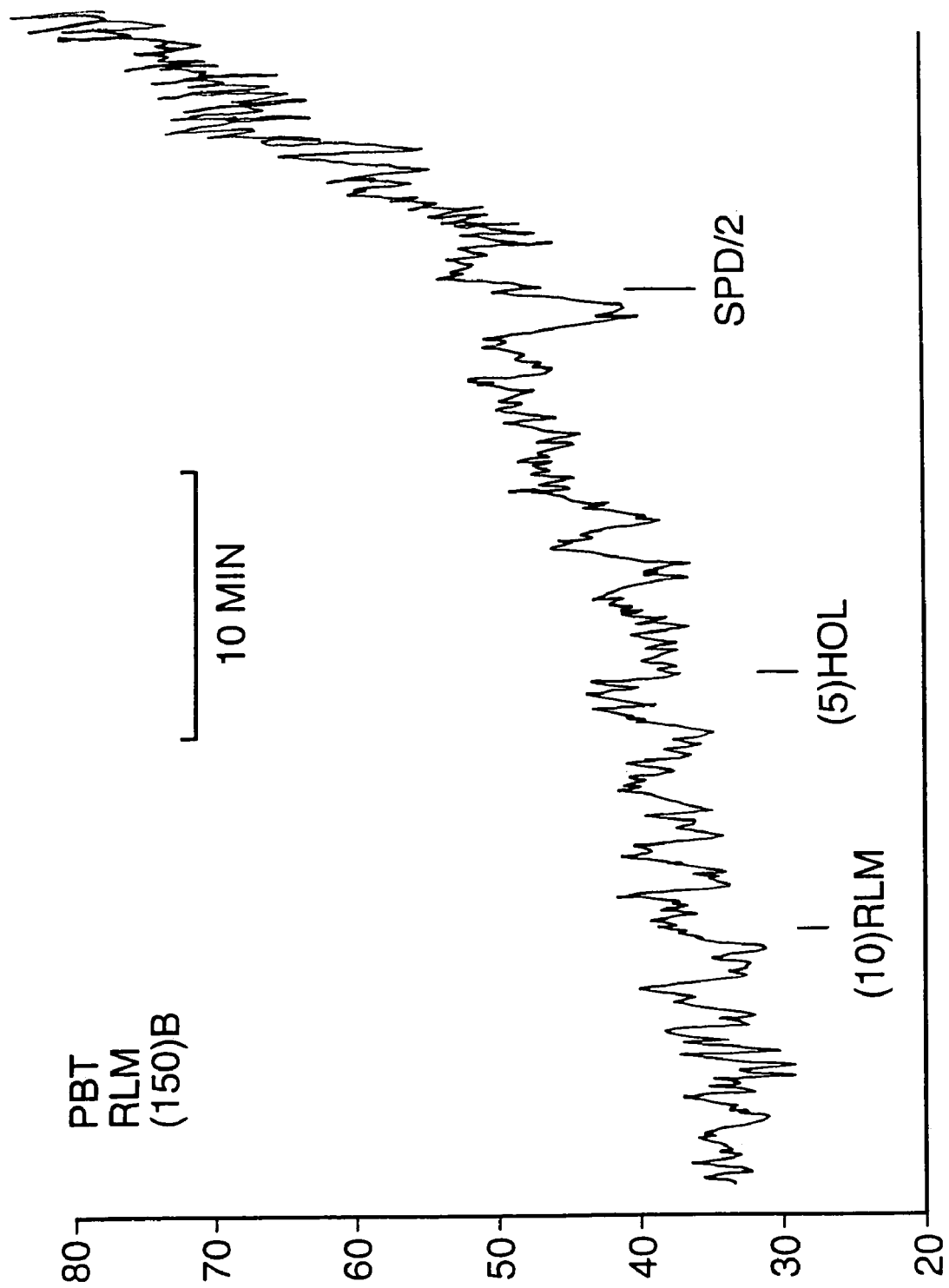
Figure 18:
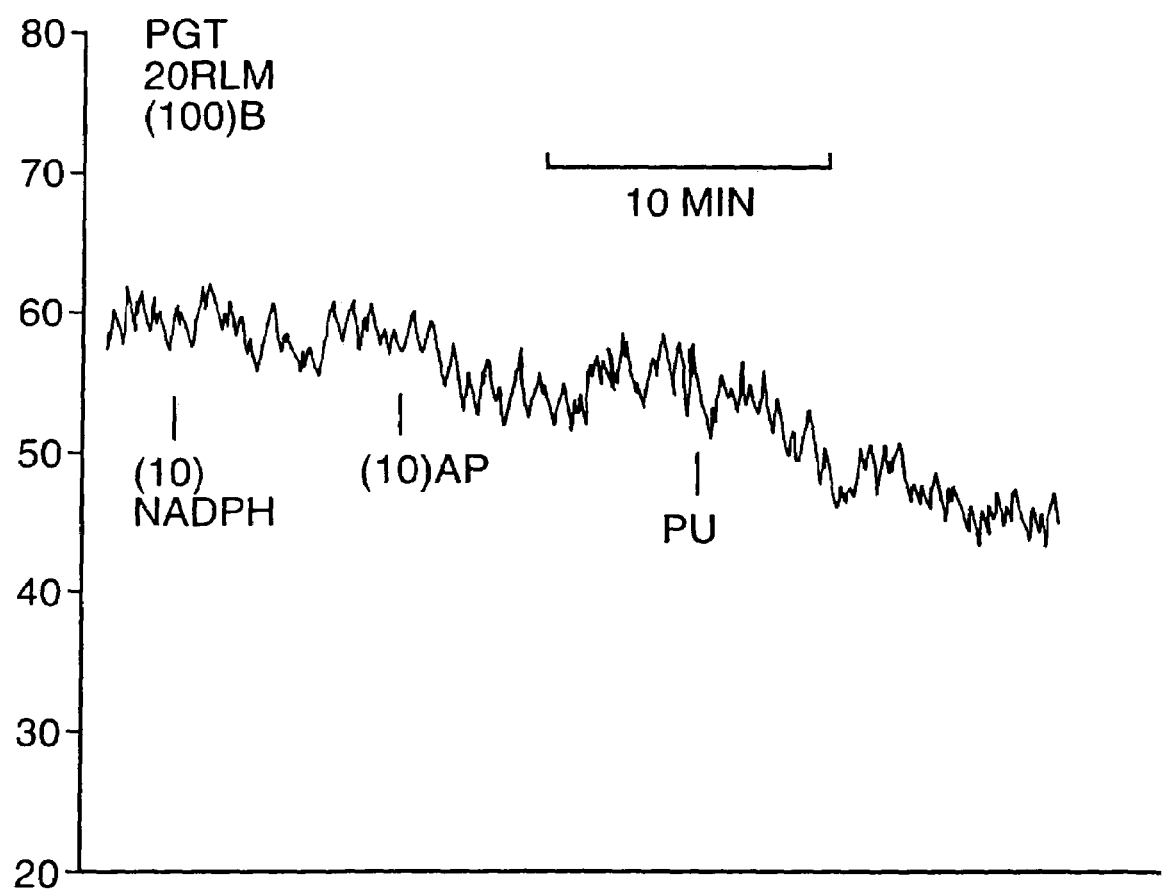
Figure 19:
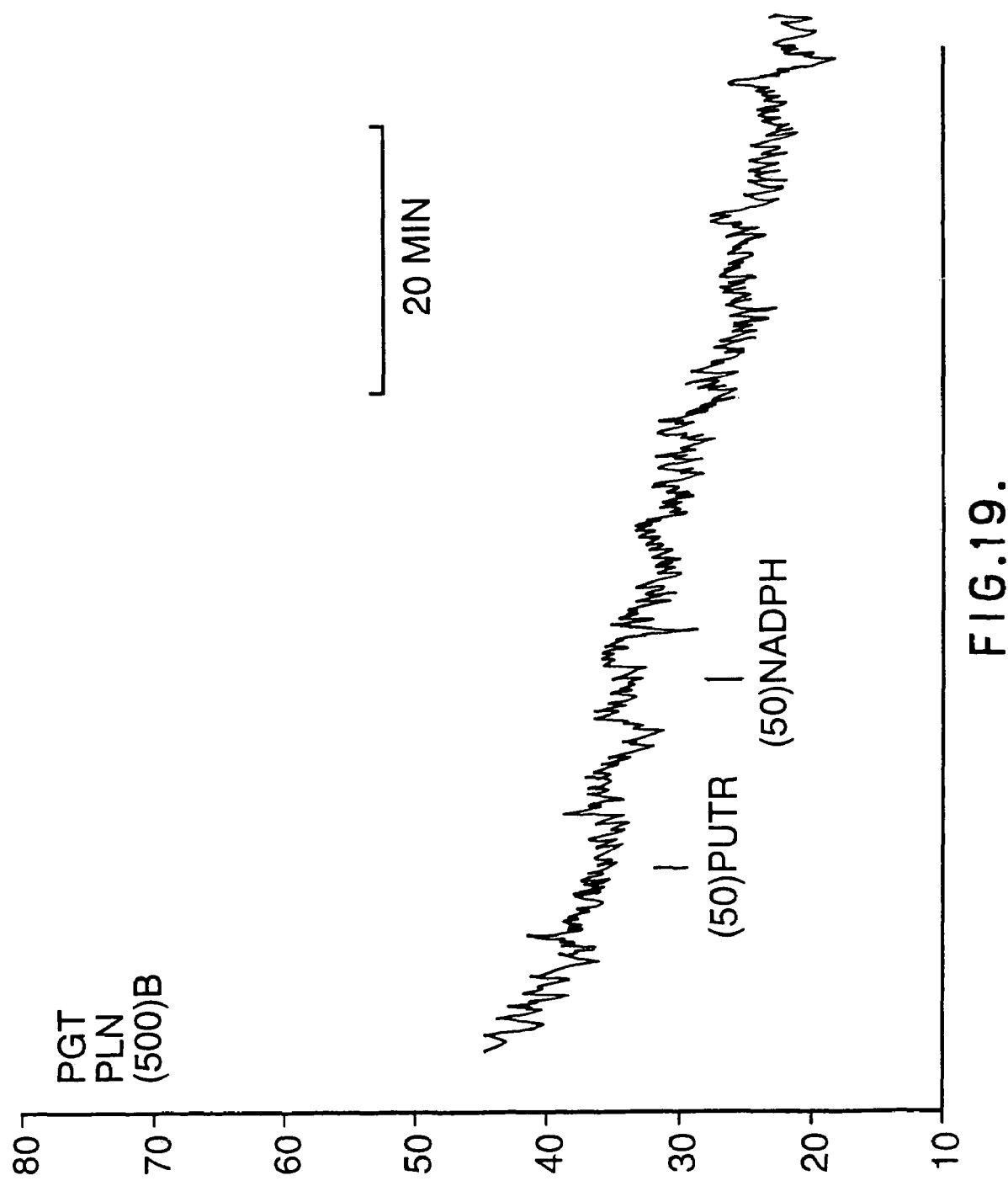
Figure 20:
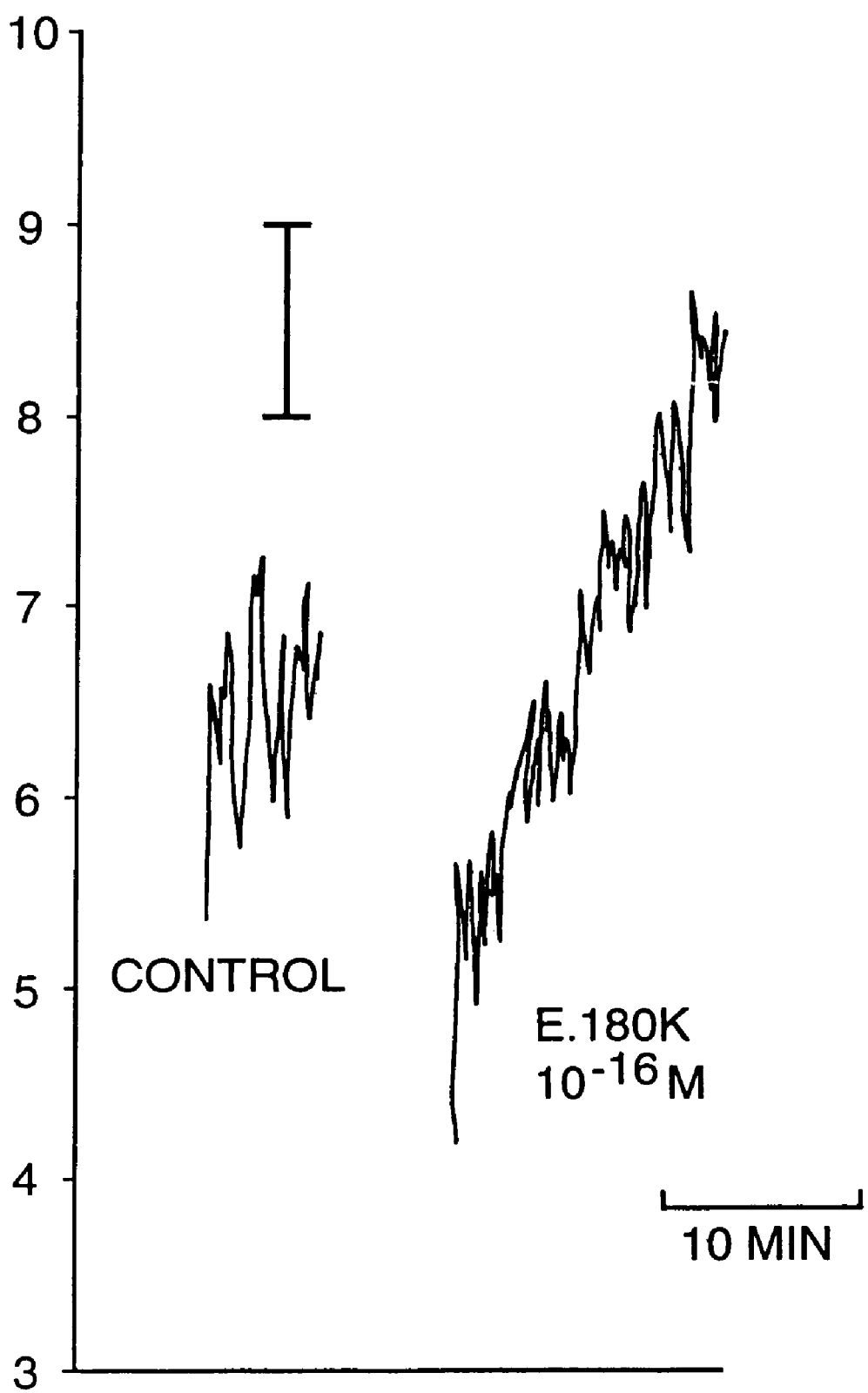
Figure 21:
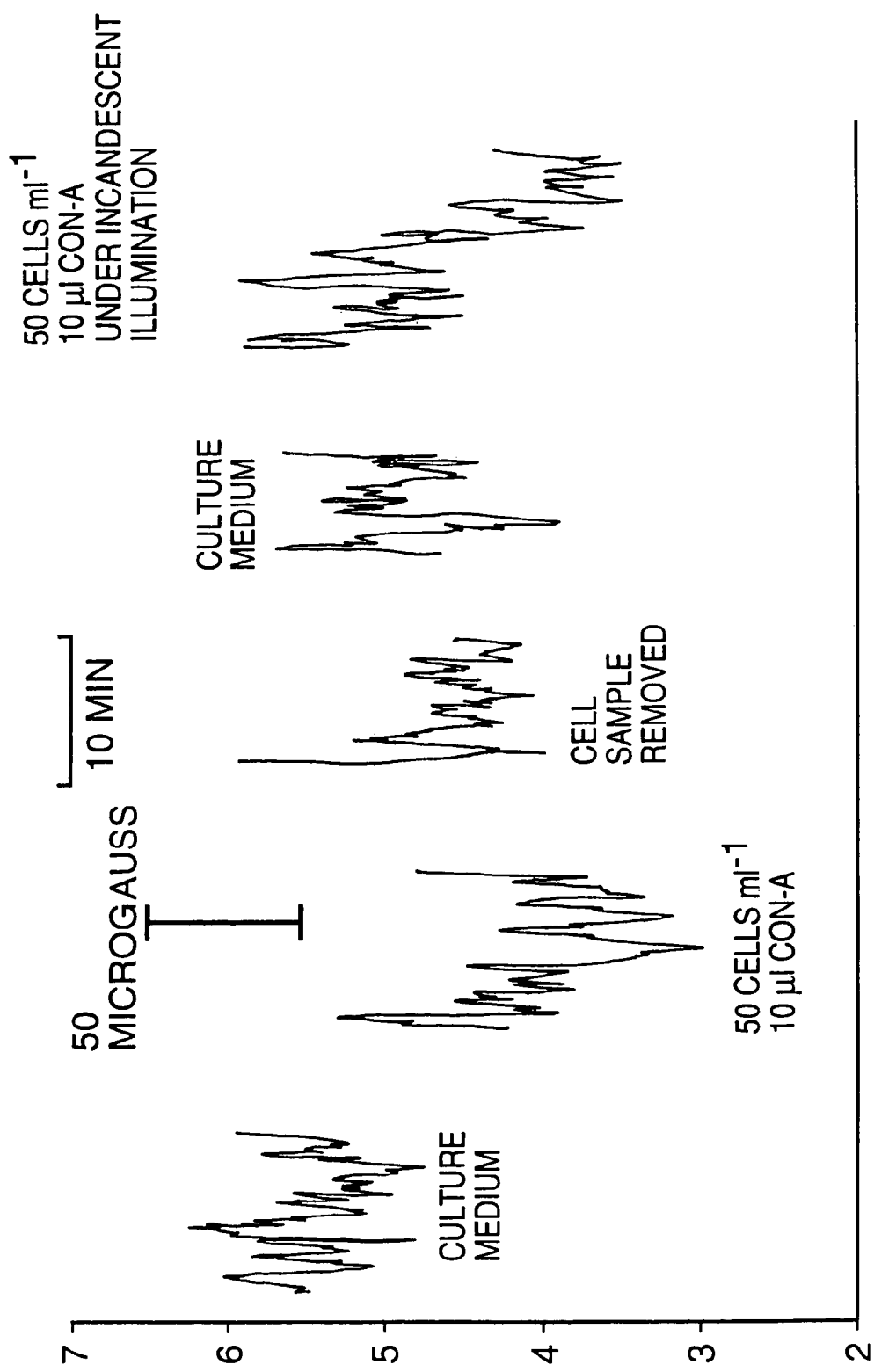
Figure 22:
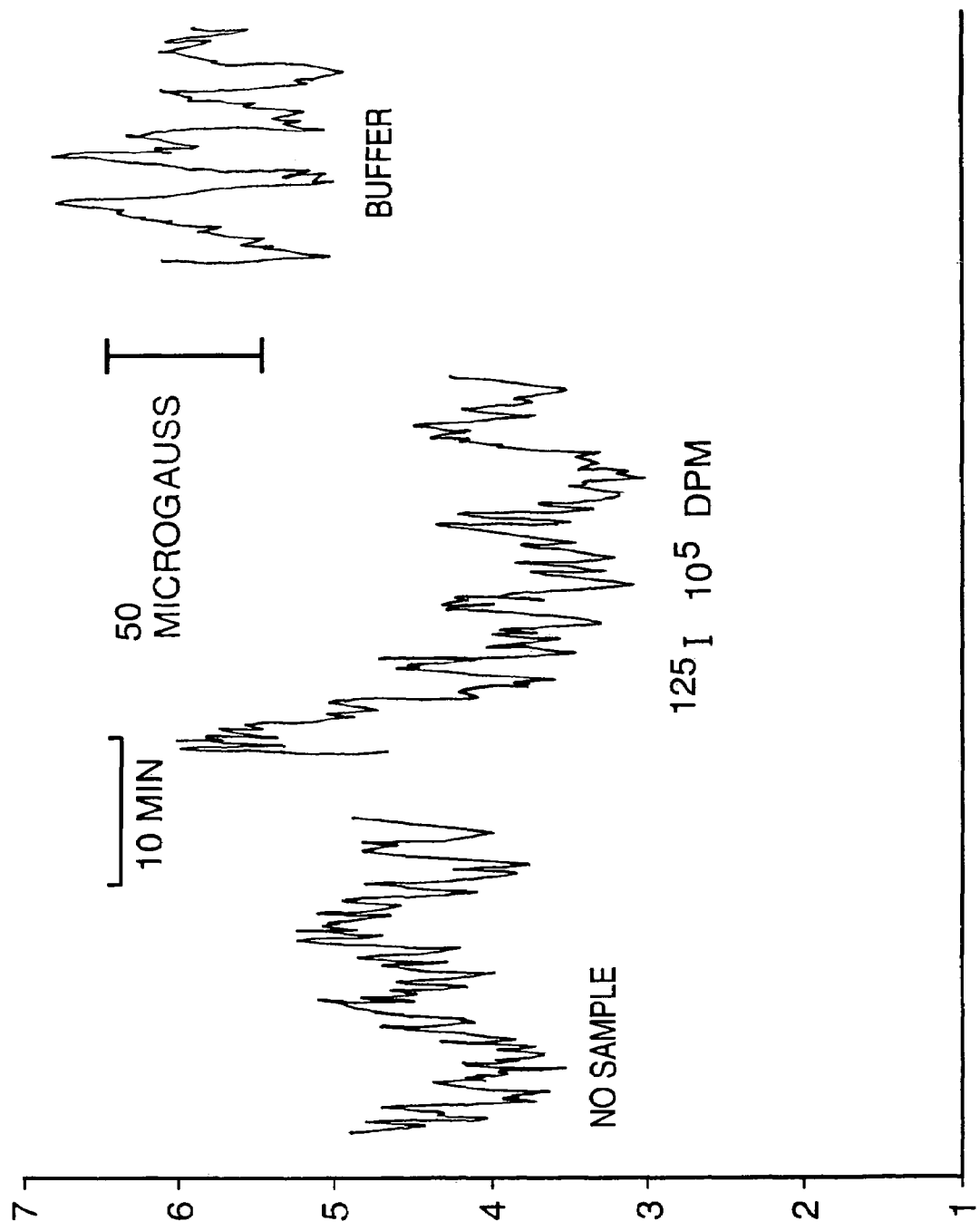
Figure 23:
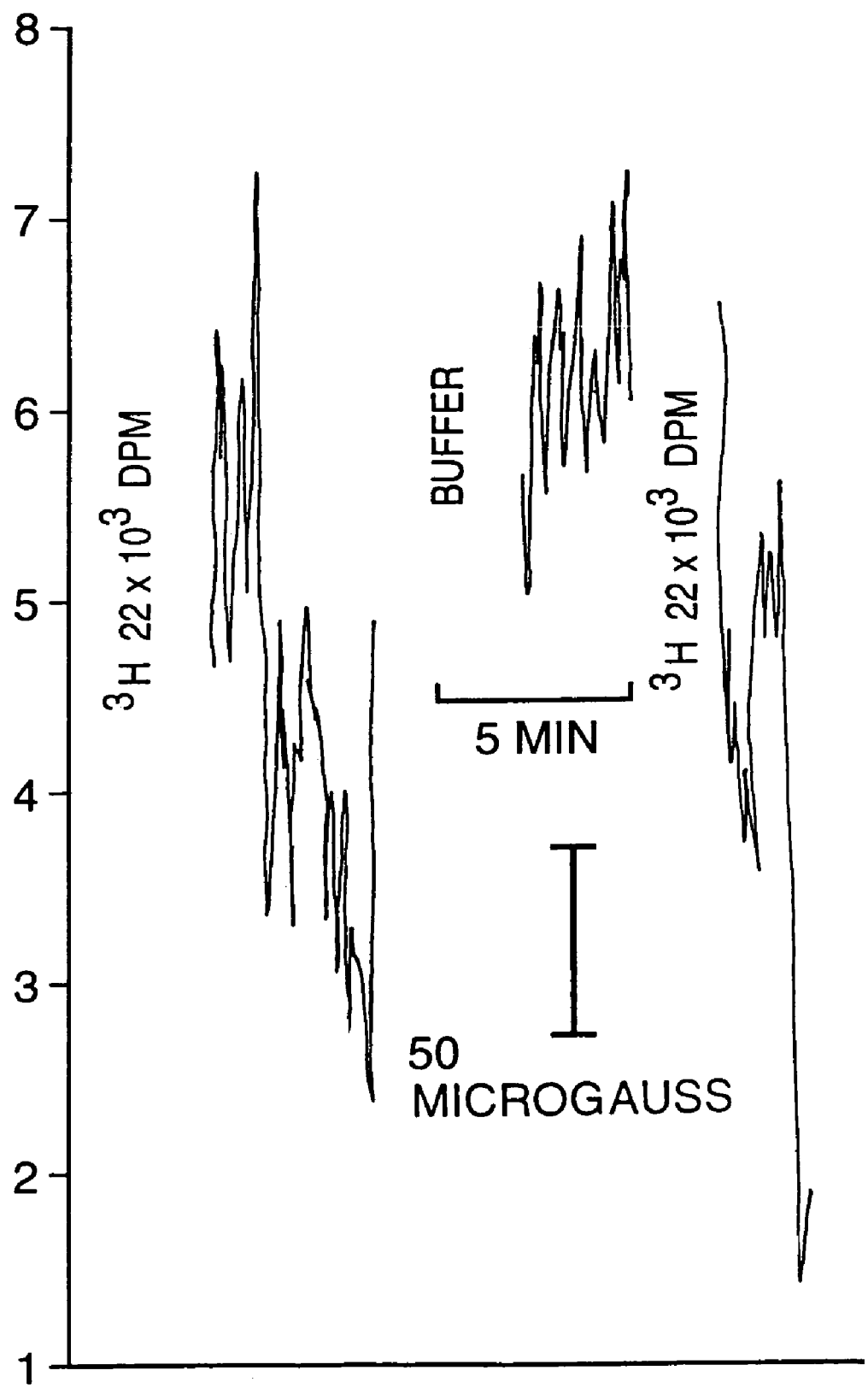

| FIG. 2 | PBT (50) B 10 CHROM Response to HD |
|---|---|
| FIG. 3 | PGT 100 CHROM (700) B. Response to HD |
| FIG. 4 | RLM. Response to AP. No further change in slope with AD |
| FIG. 5 | CHROM. Response to TEST in presence of NADPH |
| FIG. 6 | RLM. Response to ORN in presence of NADPH. |
| FIG. 7 | RLM + NADPH. Two response to HD, short latency in both. |
| FIG. 8 | RLM. Slight response to ORN. Enhanced slope with HD. PU (10) NADPH (10) response seen at end of record. |
| FIG. 9 | RLM + NADPH. Response to AN. |
| FIG. 10 | RLM. No response to ORN (unusual). No response to NADPH. Response to PU. |
| FIG. 11 | CHROM. Response to ORN. |
| FIG. 12 | Phospholipid/Buffer. Addition of PLase generates response. |
| FIG. 13 | CHROM. Response to Regen. |
| FIG. 14 | PL/Buffer. Response to purified bee venom PLase. |
| FIG. 15 | PLN. Response to HD. |
| FIG. 16 | CHROM. No response to fluoxetine (0.2 ml; "(5)FLU", on record) until NADPH added. |
| FIG. 17 | RLM. Response to HOL. "SPD/2" = chart speed reduced to ½ of original. |
| FIG. 18 | RLM + NADPH. Response to AP. Increased slope with PUTR. |
| FIG. 19 | PLN. No response to PUTR until NADPH added. |
| FIG. 20 | Non-active sample (CONTROL is 1500 μL ORN buffer as thin film. E180K (on record) is P450 isoenzyme, $10^{-16}$M (estimated as 0.1% of total protein), thin film. |
| FIG. 21 | Thin film suspension of rat liver whole cells. Same 50 cells each trial. Control responses are from culture medium. |
| FIG. 22 | $^{125}$I (NaI), ca $10^5$ DPM. |
| FIG. 23 | Tritium (uniformly labelled $^3$H-histamine), ca. $22 \times 10^3$ DPM. |

Calibrations: Unless otherwise stated, vertical deflection of one major vertical division represents approximately 5 nanoTesla (50 microgauss) at the magnetosensitive region of the Hall effect magnetometer probe. In FIGS. 20 to 23, all samples were at placements remote from probe-reaction vessel assembly.

TABLE 5

Microwave detection of Sensitivity (FIG. 1c)

A: Microwave field energy OFF.
B. Microwave field ON; 10 pico Watt at 11.3 GHz, applied via the wide bell opening of a tapered waveguide radiator, 60 cm distance from Hall effect detector surface.
C: Microwave field OFF.
Calibrations:

Minor horizontal calibrations 2 cm. Min$^{-1}$. Chart paper was running continuously during measurements. During indicated trace-free periods recorder stylus was lifted form the chart, to delineate separation between differing conditions of microwave radiation. Vertical deflection of one major division represents the equivalent of approximately 5 nanoTesla (50 microgauss) at the magnetosensitive region of the Hall effect magnetometer probe (see: legend "Calibrations" at bottom of Table 4). Recorder time-constant = 2.0 sec.
The pattern of the device response shown in the figure is typical of that seen with imposed microwave fields originating from technical sources (e.g. electronic microwave generators), chemical reactions (including inorganic, organic and biological) and from non-reacting chemical samples in the ground state. A distinct downward slope of 16 minor vertical divisions per 10 min can be seen during microwave irradiation, an upward slope of almost equal magnitude is observed promptly upon termination of microwave field energy. Horizontal and sloped lines have been drawn on the recorded traces to guide observer's eye.
Legend:

A: pre-energization magnetometer baseline fluctuations; B: magnetometer output, showing downward-sloping response to application of microwave field energy; c: magnetometer output, showing sloping response of opposite sign (upward), in response to termination of microwave field energy.

TABLE 6

Statistics for Experiments on hydrazine sulfate (FIG. 27)

All tests are run with a control and a sample. Both of these tests have a 4-minute "ON" time when the sample is in place and a 4-minute "OFF" time when the sample has been removed. All values are given in volts.

A. Means voltage values for control and test runs.

| Average control ON: | 0.000165 |
|---|---|
| Average control OFF: | 0.000055 |
| Average hydrazine ON: | −0.001344 |
| Average hydrazine OFF: | −0.000135 |

First five seconds of signal is average to yield the mean and that mean subtracted form the remaining points to normalize.

B. P(probability) values for differences in voltages between hydrazine sulfate and control

| | P value |
|---|---|
| Control on vs. control off | 0.8412 |
| Hydrazine on vs. hydrazine off: | 0.0037 |
| Control on vs. hydrazine off: | 0.0018 |
| Control off vs. hydrazine on: | 0.0150 |

TABLE 7

Hydrazine: Density Results

| | Total | | Number | | Mean Size | | Number of Runs | |
|---|---|---|---|---|---|---|---|---|
| Date | C | S | C | S | C | S | C | S |
| Instrument 405 | | | | | | | | |
| September 3 | 9276 | 9343 | 53.18 | 51.3 | 178.5 | 183.6 | 11 | 10 |
| September 4 | 9183 | 8853 | 54.08 | 55.42 | 172.0 | 162.4 | 12 | 12 |
| September 5 | 8818 | 8860 | 51.63 | 51.13 | 176.1 | 175.0 | 8 | 8 |
| September 8 | 6776 | 7704 | 54.33 | 53.17 | 127.2 | 146.1 | 6 | 6 |
| September 16 | 7392 | 7518 | 51.8 | 56.8 | 143.3 | 133.8 | 5 | 5 |
| September 17 | 5609 | 5682 | 77.4 | 72.2 | 73.9 | 78.9 | 5 | 5 |
| September 23 | 5572 | 5743 | 71 | 70.67 | 78.8 | 81.9 | 4 | 6 |
| September 25 | 5403 | 5438 | 71.88 | 69.35 | 76.1 | 78.8 | 17 | 17 |
| October 1 | 8999 | 9424 | 53.67 | 51.67 | 168.4 | 183.0 | 3 | 3 |
| October 6 | 10057 | 9832 | 56.5 | 66 | 178.9 | 150.0 | 2 | 3 |
| October 7 | 6733 | 6768 | 52 | 51.08 | 130.3 | 133.4 | 12 | 12 |
| October 8 | 10214 | 10166 | 60.25 | 68 | 172.1 | 150.4 | 4 | 4 |
| October 14 | 10133 | 9272 | 59.33 | 59 | 171.5 | 156.7 | 3 | 3 |
| October 16 | 10286 | 10161 | 57.67 | 58.33 | 178.4 | 174.7 | 3 | 3 |
| October 27 | 10016 | 10041 | 66.25 | 60.42 | 152.2 | 168.6 | 12 | 12 |
| October 29 | 14401 | 14492 | 63.14 | 63.14 | 230.8 | 233.5 | 7 | 7 |
| October 30 | 13819 | 14241 | 63 | 62.25 | 219.7 | 234.0 | 4 | 4 |
| October 31 | 13983 | 14313 | 65.3 | 64.3 | 215.5 | 224.7 | 10 | 10 |
| November 3 | 14587 | 13766 | 63.63 | 63.88 | 232.6 | 217.3 | 8 | 8 |
| November 4 | 14191 | 14206 | 66.38 | 64.5 | 217.4 | 223.2 | 8 | 8 |
| November 5 | 14275 | 14460 | 62 | 61.25 | 233.8 | 238.1 | 6 | 8 |
| November 6 | 14907 | 14461 | 65.13 | 60.38 | 232.4 | 243.1 | 8 | 8 |
| November 7 | 14183 | 14802 | 68.75 | 63.38 | 207.6 | 235.9 | 8 | 8 |
| November 12 | 13565 | 14798 | 58.4 | 65.25 | 233.4 | 230.7 | 9 | 8 |
| November 13 | 14985 | 14260 | 58 | 64 | 261.0 | 225.5 | 5 | 5 |
| November 14 | 13315 | 13396 | 67 | 67 | 199 | 199.9 | 2 | 2 |
| November 17 | 14597 | 14811 | 67.5 | 60.5 | 217.7 | 248.3 | 12 | 12 |
| November 18 | 13980 | 14738 | 66.5 | 70 | 212.5 | 210.5 | 2 | 2 |
| November 19 | 14290 | 14436 | 65.78 | 62.56 | 219.8 | 234.1 | 9 | 9 |
| | | | 21/29 | 18/29 | | 19/29 | | |

TABLE 8

Perchlorate: Density Results

| Date | Total | | Number | | Mean Size | | Number of Runs | |
|---|---|---|---|---|---|---|---|---|
| | C | S | C | S | C | S | C | S |
| Instrument 405 | | | | | | | | |
| November 21 | 14119 | 14578 | 64.5 | 61 | 219.1 | 242.1 | 4 | 4 |
| November 24 | 14112 | 13429 | 69.33 | 62.86 | 208.5 | 215.5 | 6 | 7 |
| November 27 | 14463 | 14363 | 63.27 | 62.73 | 233.4 | 230.8 | 11 | 11 |
| November 28 | 14323 | 15058 | 65.62 | 64.14 | 220.7 | 241.9 | 8 | 7 |
| December 1 | 14439 | 14831 | 64.22 | 62.67 | 226.7 | 238.0 | 9 | 9 |
| December 2 | 14732 | 14783 | 63.5 | 61.83 | 233.6 | 244.2 | 6 | 6 |
| December 8 | 14394 | 14746 | 70.67 | 63.67 | 204.2 | 232.2 | 3 | 3 |
| December 9 | 14615 | 14830 6/8 | 65.29 8/8 | 58.85 | 225.3 | 255.3 7/8 | 7 | 7 |
| Instrument 324 | | | | | | | | |
| November 25 | 4929 | 4734 | 64.67 | 62.8 | 76.59 | 67.38 | 3 | 5 |
| December 4 | 8145 | 8120 | 87.5 | 81.67 | 93.64 | 99.44 | 4 | 6 |
| December 5 | 9216 | 9322 | 81.7 | 78.9 | 113.4 | 118.5 | 10 | 10 |
| December 8 | 7558 | 7455 | 90.14 | 86 | 85.09 | 86.90 | 7 | 7 |
| December 11 | 2778 | 2642 | 85 | 83.5 | 32.75 | 31.69 | 3 | 4 |
| December 12 | 2871 | 2936 4/6 | 84.67 6/6 | 77.5 | 34.96 | 39.22 4/6 | 3 | 2 |

TABLE 9

Preliminary results: success rate in distinguishing between concealed chemical sample (hydrazine sulfate) and control sample (empty bottle) based on a "neural network" computer program.

The process of "training" the computer program consists of feeding the network with several input vectors (recording features) for which the output is already known. The weights and biases of the network are then updated using previous initial estimates of the same, as well as the error between the desired output and the obtained output from the network. The training process is completed when this iterative updating process converges or until the sum-of-squares error value between the obtained and desired output of the network falls below a pre-determined low value. Once the network is trained, it can be tested with new input vectors, to determine whether or not the success rate to identify samples is thereby enhanced.

Features of the signals generated during the presence of the chemical that were used to train the network include:

1. the maximum correlation of the signal under test with the composite control vector.
2. the time at which the best correlation occurs.
3. the maximum correlation of the signal under test with the composite hydrazine vector.
4. the time at which maximum correlation occurs.
5: the 95% confidence limit of the baseline preceding the signal.
6. the confidence limit of the first 2 minutes of response signal, divided by the equivalent baseline confidence limit (feature 5).
7-11: same as 6 for each subsequent 2-minute period.

What we claim is:

1. A method of detecting a chemical substance, which comprises:
    using magnetometer means to generate an electrical signal of strength proportional to near or propagating electromagnetic fields originating in the substance, and
    recording a time course of the changes in electromagnetic field strength as an identification of the substance.

2. The method of claim 1 wherein the substance is concealed.

3. The method of claim 2 wherein the substance is in its ground state.

4. The method of claim 1 wherein the substance is an explosive, radioactive isotope or chemically-active organic matter.

5. The method of claim 1 wherein the substance is remotely located from the location of detection.

\* \* \* \* \*